(12) United States Patent
Perrin et al.

(10) Patent No.: US 11,207,432 B2
(45) Date of Patent: *Dec. 28, 2021

(54) SUBSTITUTED ORGANOFLUOROBORATES AS IMAGING AGENTS

(71) Applicant: THE UNIVERSITY OF BRITISH COLUMBIA, Vancouver (CA)

(72) Inventors: David Perrin, Vancouver (CA); Zhibo Liu, Vancouver (CA)

(73) Assignee: THE UNIVERSITY OF BRITISH COLUMBIA, Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,458

(22) Filed: Jan. 17, 2020

(65) Prior Publication Data
US 2020/0222563 A1 Jul. 16, 2020

Related U.S. Application Data

(63) Continuation of application No. 14/773,743, filed as application No. PCT/CA2014/000200 on Mar. 7, 2014, now Pat. No. 10,556,023.

(60) Provisional application No. 61/775,280, filed on Mar. 8, 2013.

(51) Int. Cl.
| | | |
|---|---|---|
| *A61K 51/00* | (2006.01) | |
| *A61M 36/14* | (2006.01) | |
| *A61K 51/04* | (2006.01) | |
| *C07F 5/02* | (2006.01) | |
| *A61K 51/08* | (2006.01) | |
| *C07B 59/00* | (2006.01) | |
| *C07K 1/13* | (2006.01) | |

(52) U.S. Cl.
CPC .......... *A61K 51/04* (2013.01); *A61K 51/0421* (2013.01); *A61K 51/0453* (2013.01); *A61K 51/0455* (2013.01); *A61K 51/082* (2013.01); *A61K 51/088* (2013.01); *C07B 59/00* (2013.01); *C07F 5/02* (2013.01); *A61K 51/00* (2013.01); *C07F 5/027* (2013.01); *C07K 1/13* (2013.01)

(58) Field of Classification Search
None
See application file for complete search history.

(56) References Cited

U.S. PATENT DOCUMENTS

| | | | |
|---|---|---|---|
| 6,166,226 A | 12/2000 | Buchwald et al. | |
| 7,041,859 B1 | 5/2006 | Kabalka | |
| 8,574,546 B2 | 11/2013 | Perrin et al. | |
| 10,556,023 B2 * | 2/2020 | Perrin | A61K 51/0455 |
| 2006/0128664 A1 | 6/2006 | Holmes-Farley et al. | |

FOREIGN PATENT DOCUMENTS

| | | |
|---|---|---|
| CA | 2267153 | 4/1998 |
| CA | 2710923 | 2/2010 |
| CA | 2810241 | 3/2012 |
| CA | 2931554 | 6/2015 |
| EP | 1027316 | 8/2000 |
| EP | 1089305 | 4/2001 |
| EP | 2226328 | 9/2010 |
| EP | 2555796 | 2/2013 |
| WO | WO 05/077967 A1 | 8/2005 |
| WO | WO 07/032005 A2 | 3/2007 |
| WO | WO 09/012596 A1 | 1/2009 |
| WO | WO-2011/124931 | 10/2011 |
| WO | WO 14/134716 A1 | 9/2014 |

OTHER PUBLICATIONS

EP Office Action dated Mar. 10, 2020 in corresponding European Appln No. 14759809.8 (20 pages).
Onufriev et al., A Novel View of pH Titration in Biomolecules, Biochemistry, vol. 40, No. 12, Mar. 27, 2001 (7 pages).
Bagutski et al. (Tetrahedron 2009, 65, 9956-9960).
Lawrence et al. (J. Am. Chem. Soc. 2004, 126, 15334-15335).
Raushel et al. (J. Org. Chem. 2011, 76, 2762-2769).
Molander et al. (J. Org. Chem. 2008, 73, 3885-3891).
Kirkham et al. (Org. Letters, 2012, 14, 5354-5357).
ESR for EP2964658 dated Oct. 4, 2016.
Bernard-Gauthier, V. et al., "From Unorthodox to Established: The Current Status of $^{18}$F-Trifluoroborate- and $^{18}$F-SIFA-Based Radiopharmaceuticals in PET Nuclear Imaging," Bioconjugate Chemistry, 2016, vol. 27, pp. 267-279.
Harwig, C.W., et al., "Synthesis and characterization of 2,6-difluoro-4-carboxyphenylboronic acid and a biotin derivative thereof as captors of anionic aqueous [$^{18}$F]-fluoride for the preparation of [$^{18}$F/$^{19}$F]-labeled aryltrifluoroborates with high kinetic stability," Tetrahedron Letters, 2008, vol. 49, pp. 3152-3156.
Liu, Z., et al., "An Organotrifluoroborate for Broadly Applicable One-Step 18F-Labeling," Angewandte Chem, Int. Ed., 2014, vol. 53, pp. 11876-11880.
Na Sun et al., "Biorelevant pKa (37°C) predicted from the 2D structure of the molecule and its pKa at 25 °C," Journal of Pharmaceutical and Biomedical Analysis, vol. 56, No. 2, 2011, pp. 173-182.
Smith, M. et al., "March's Advanced Organic Chemistry: Reactions, Mechanisms, and Structure," 7th ed., Jun. 13, 2013, John Wiley & Sons, vol. 116, pp. 334-346.
Office Action for European Application No. 14759809.8 dated Oct. 10, 2018, 17 pages.
Boutourine et al., "Rapid Routes of Synthesis of Chemically Reactive and Highly Radioactive Labeled α- and β-Oligonucleotide Derivatives for in Vivo Studies," Bioconjugate Chemistry, 1:350-356, (1990).
Dumas et al., "Synthesis of Acyltrifluoroborates," Organic Letters, 14:2138-2141, (2012).
Harwig et al., Synthesis and characterization of 2,6-difluoro-4-carboxyphenylboronic acid and a biotin derivative thereof as captors of anionic aqueous [18F]-fluoride for the preparation of [18F/19F]-labeled aryltrifluoroborates with high kinetic stabili.
Lennox et al.,"Organotrifluoroborate Hydrolysis: Boronic Acid Release Mechanism and an Acid-Base Paradox in Cross-Coupling," JACS, 134:7431-7441, (2012).

(Continued)

*Primary Examiner* — Michael G. Hartley
*Assistant Examiner* — Melissa J Perreira
(74) *Attorney, Agent, or Firm* — Cooley LLP

(57) ABSTRACT

Fluoridated organofluoroborates comprising at least one $^{18}$F atom and precursors thereto, for use in PET scanning.

15 Claims, 13 Drawing Sheets

(56) References Cited

OTHER PUBLICATIONS

Li et al. "Hydrolytic stability of nitrogenous-heteroaryltrifluoroborates under aqueous conditions at near neutral pH," Journal of Fluorine Chemishy, 130:377-382, (2009).

Means et al., "Chemical Modifications of Proteins: History and Applications", Bioconjugate Chemistry, 1:2-12, (1990.

Molander et al., "Synthesis of an Acyltrifluoroborate and its Fusion with Azides to Form Amides," J. Org. Chem., 75: 4304-4306, (2010).

Molander et al., "Synthesis of Functionalized Organotriflurorborates via the 1,3-Dipolar Cycloaddition of Azides," Organic Letters, 8:2031-2034, (2006).

Ting et al. "Arylfluoroborates and Alkylfluorosilicates as Potential PET Imaging Agents: High-Yielding Aqueous Biomolecular 18F-Labeling," J. Am. Chem. Soc., 127:13094-13095, (2005).

Ting et al. "Capturing aqueous [18F]-fluoride with an arylboronic ester for PET: Synthesis and aqueous stability of a fluorescent [18F]-labeled aryltrifluoroborate,"Journal of Fluorine Chemistry, 129:349-358, (2008).

Ting et al. "Toward [18F]-Labeled Aryltrifluoroborate Radiotracers: In Vivo Positron Emission Tomography Imaging of Stable Aryltrifluoroborate Clearance in Mice," J. Am. Chem. Soc., 130:12045-12055, (2008).

Ting et al., "Substitutent effects on aryitrifluoroborate solvolysis in water: Implications for Suzuki-Miyaura coupling and the design of stable 18F-labeled aryitrifluoroborates for use in PET imaging", J. Org. Chem., 73:4662-4670, (2008).

WIPO Application No. PCT/CA2014/000200, PCT International Preliminary Report on Patentability dated Sep. 8, 2015.

WIPO Application No. PCT/CA2014/000200, PCT International Search Report dated Nov. 6, 2014.

WIPO Application No. PCT/CA2014/000200, PCT Written Opinion of the International Searching Authority dated Jun. 11, 2014.

* cited by examiner

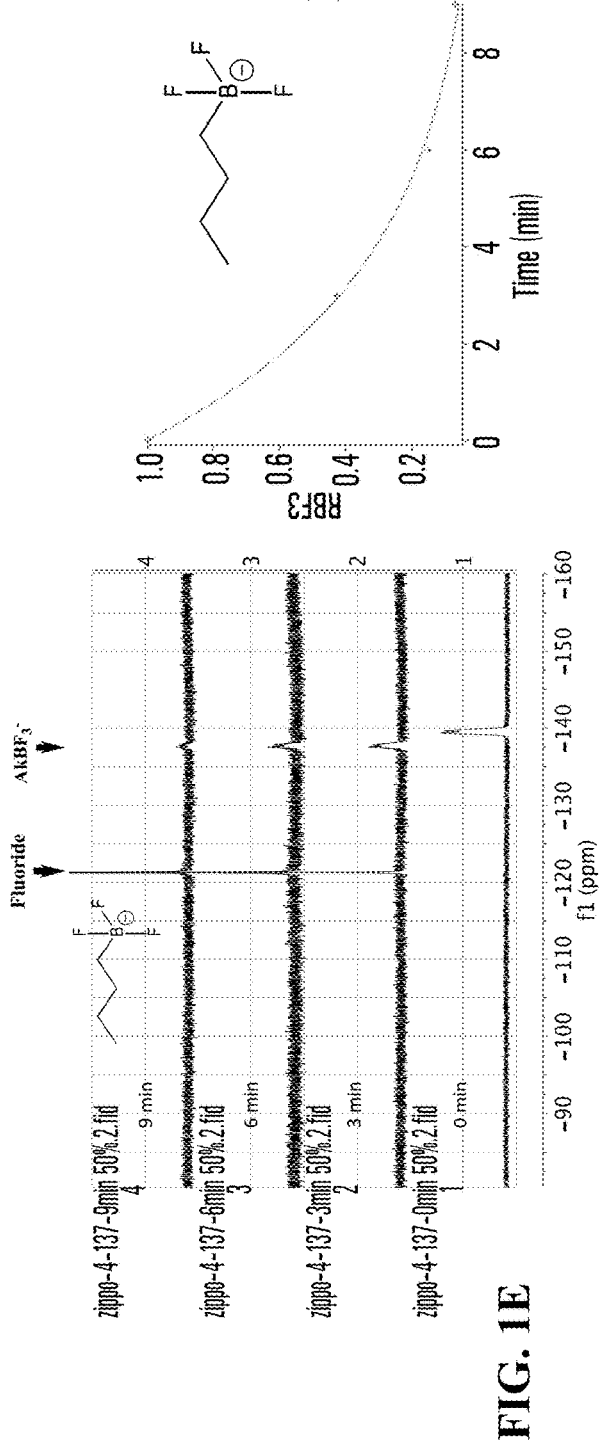
FIG. 1E
FIG. 1F
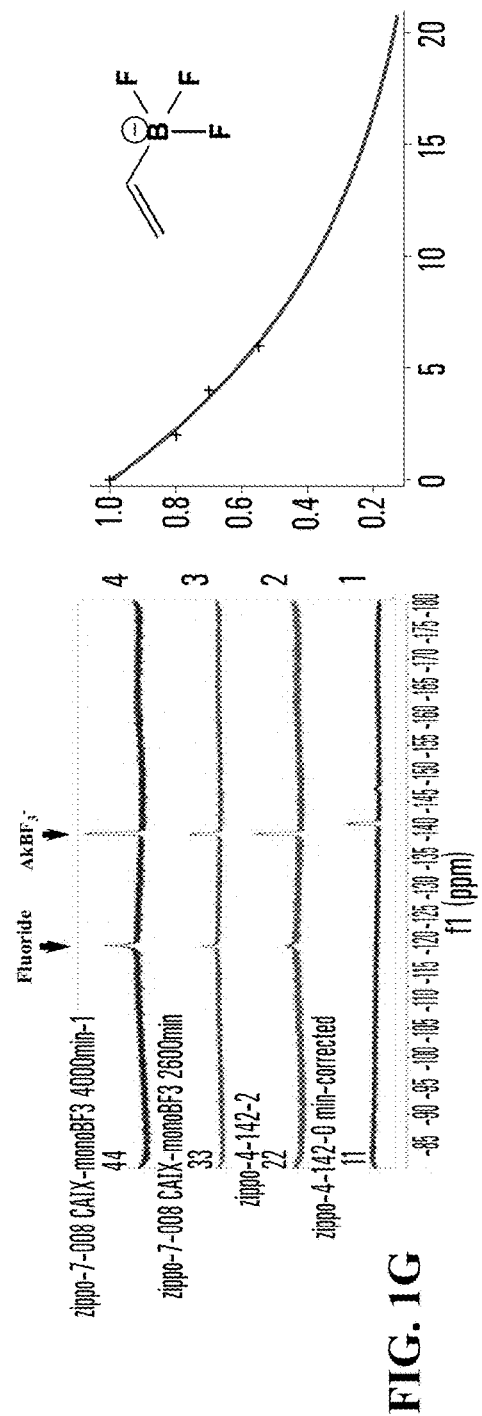
FIG. 1G
FIG. 1H

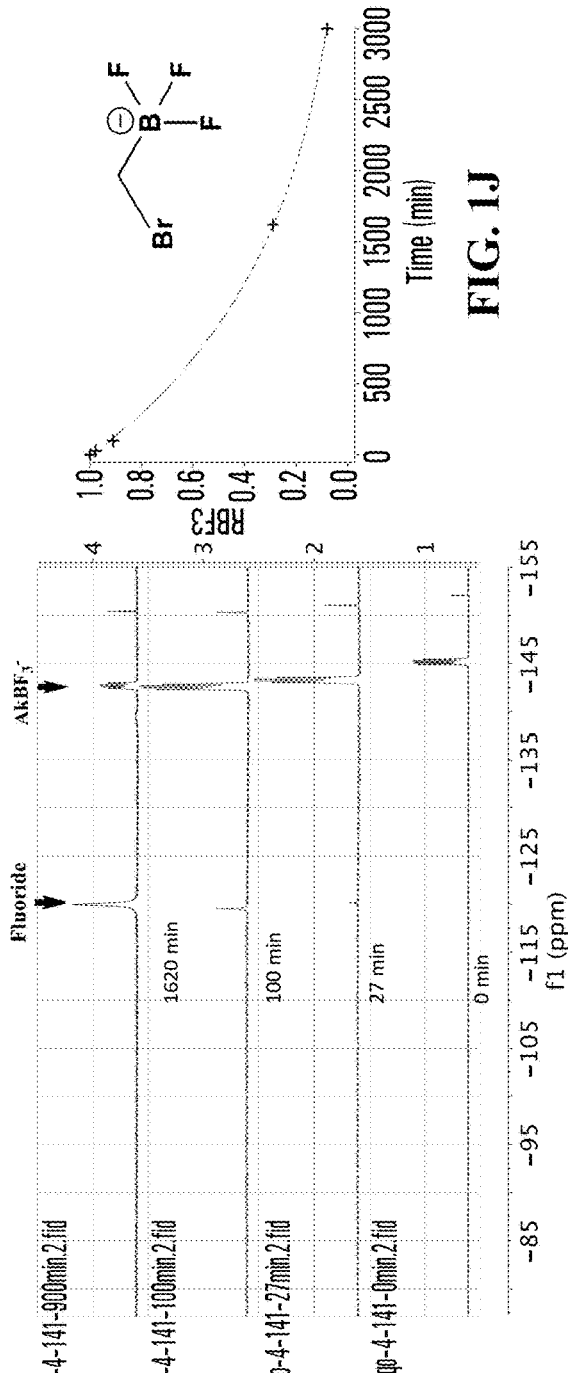
FIG. 1I
FIG. 1J
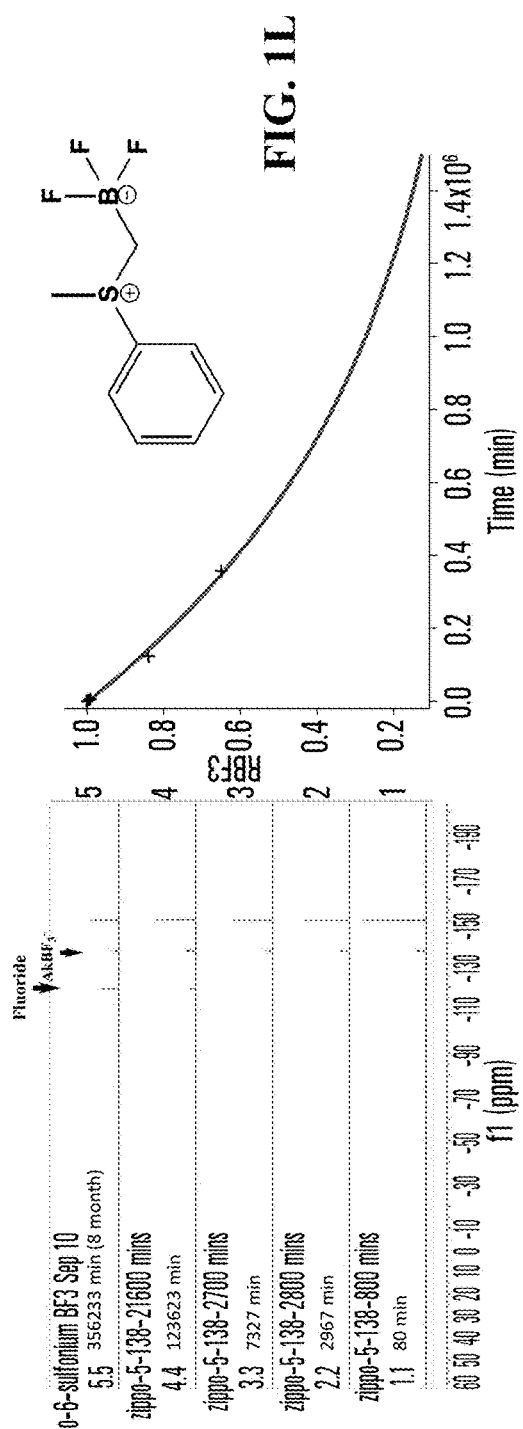
FIG. 1K
FIG. 1L

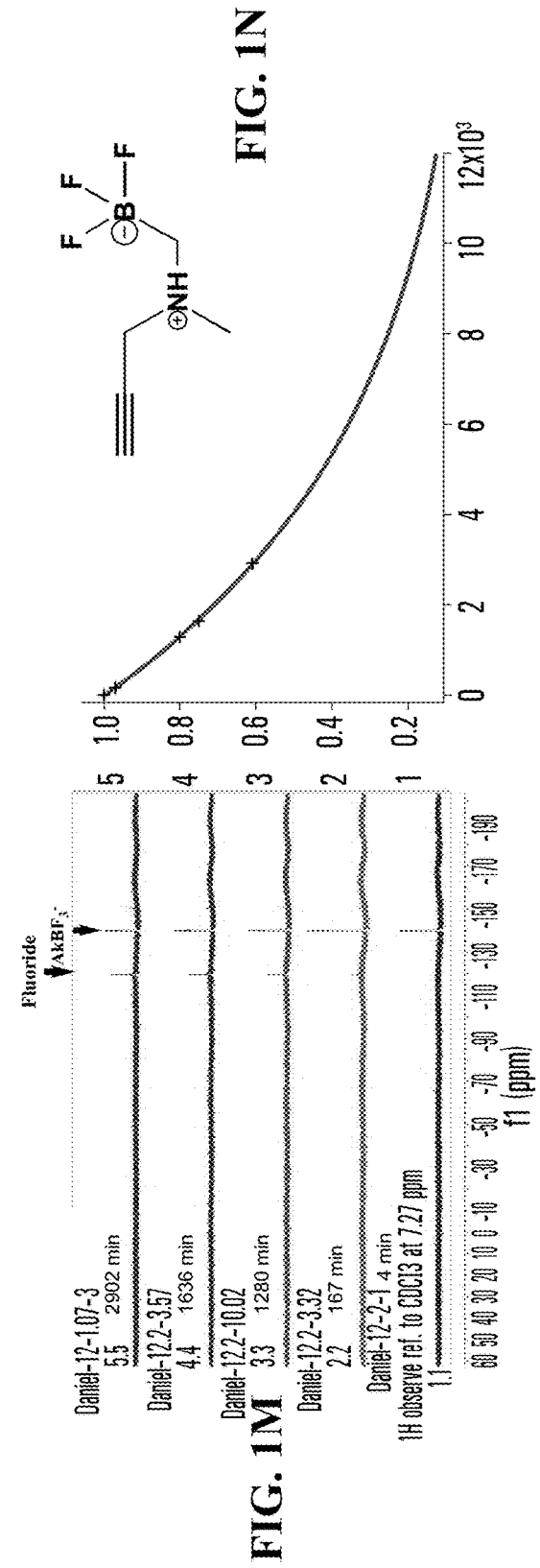
FIG. 1M
FIG. 1N
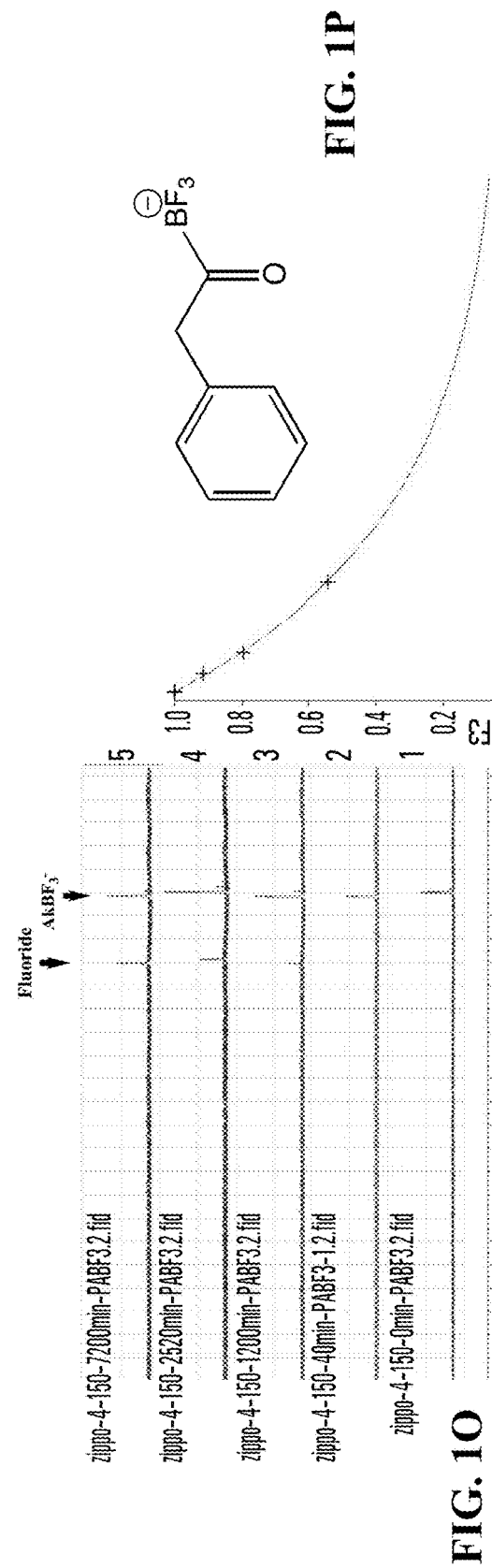
FIG. 1O
FIG. 1P

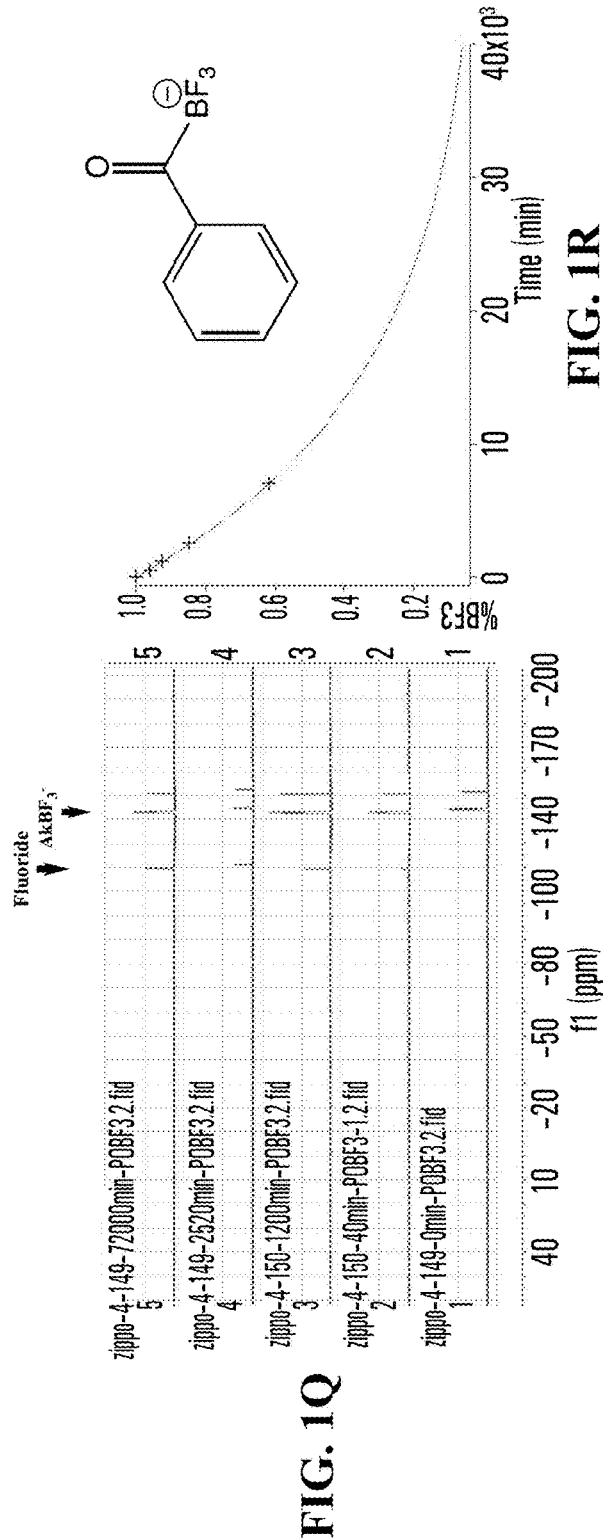
FIG. 1Q
FIG. 1R
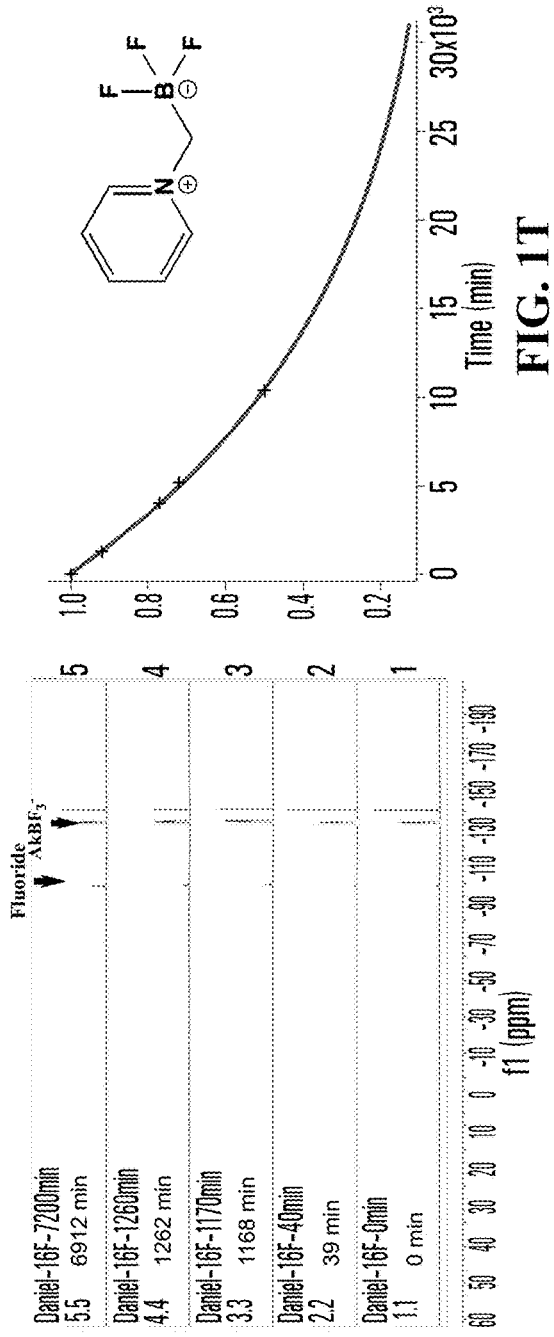
FIG. 1S
FIG. 1T

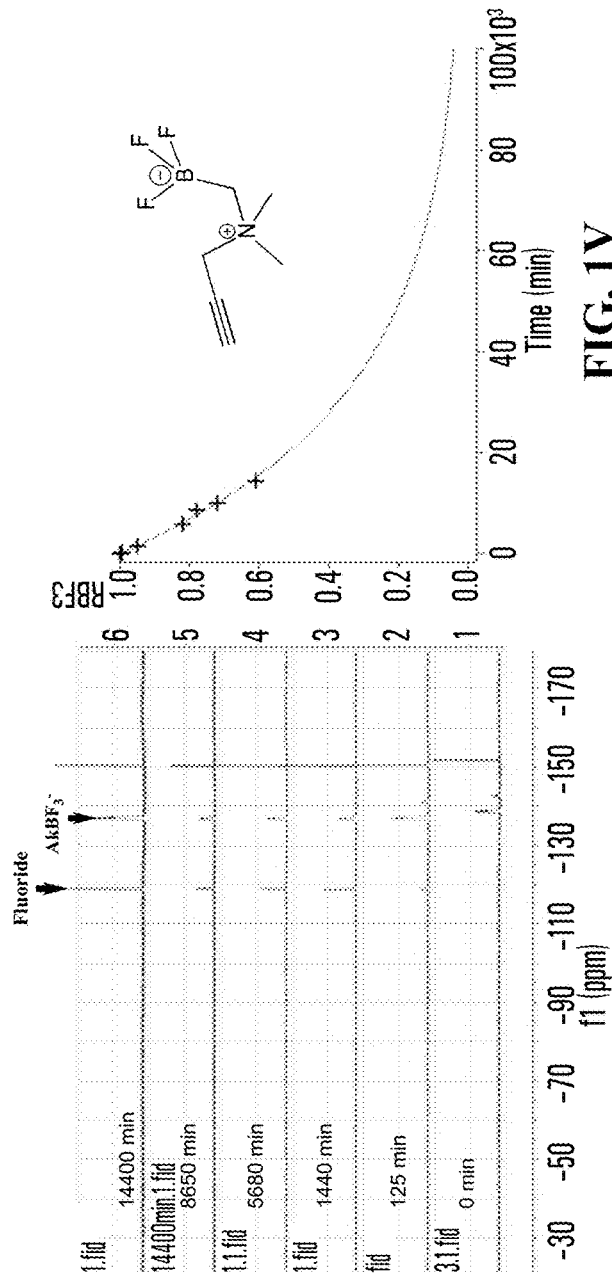
FIG. 1U
FIG. 1V
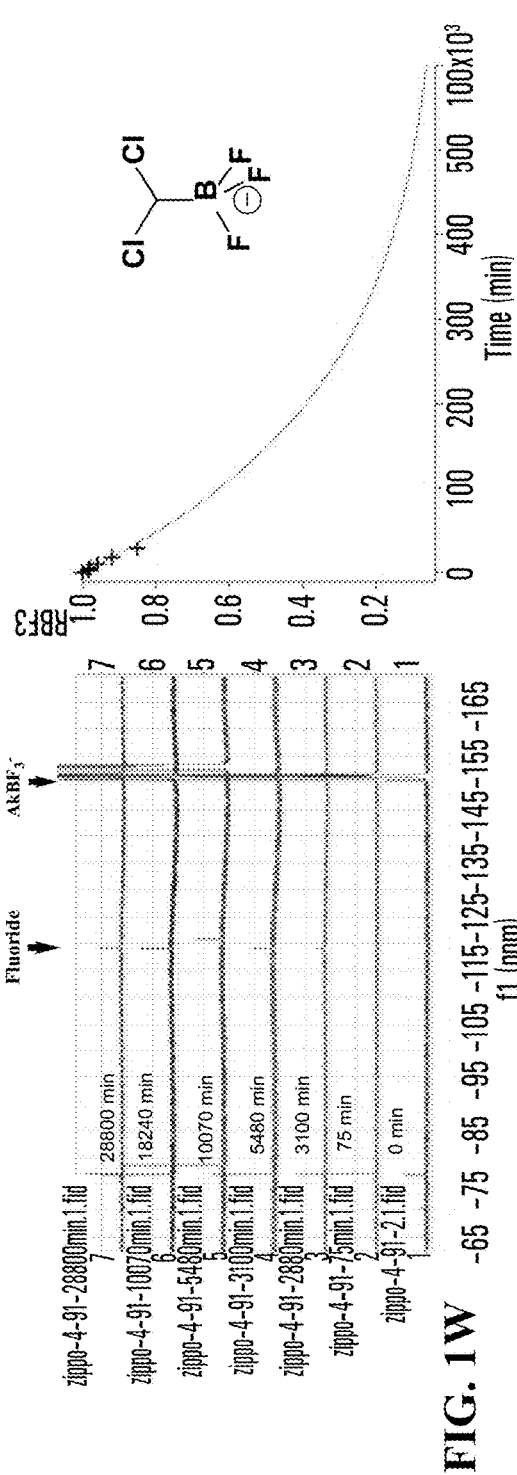
FIG. 1W
FIG. 1X

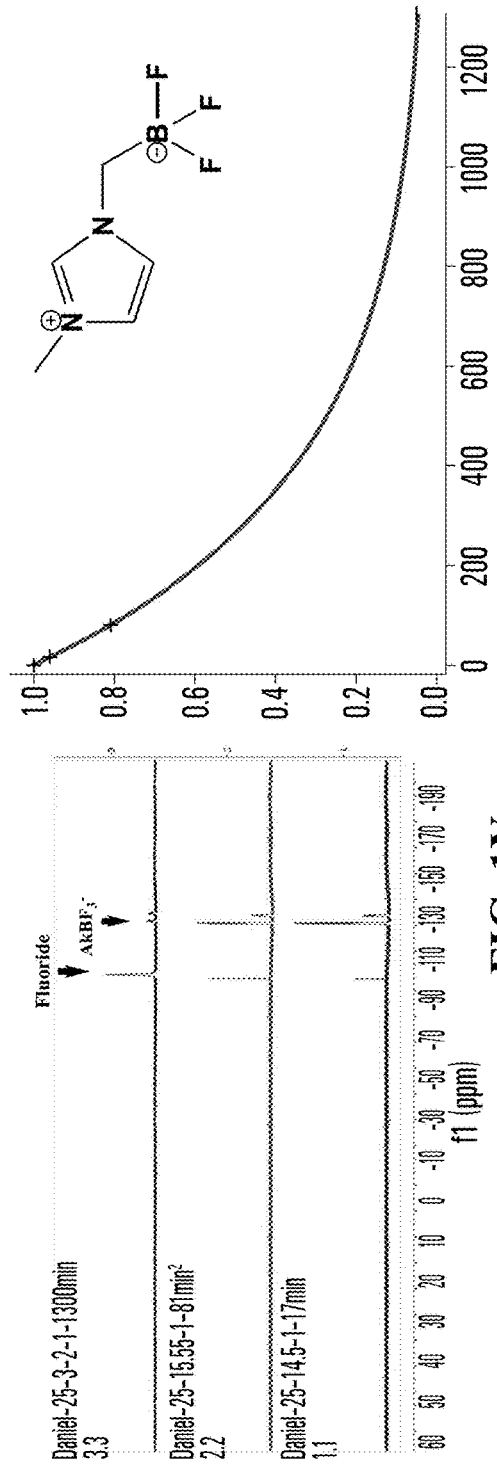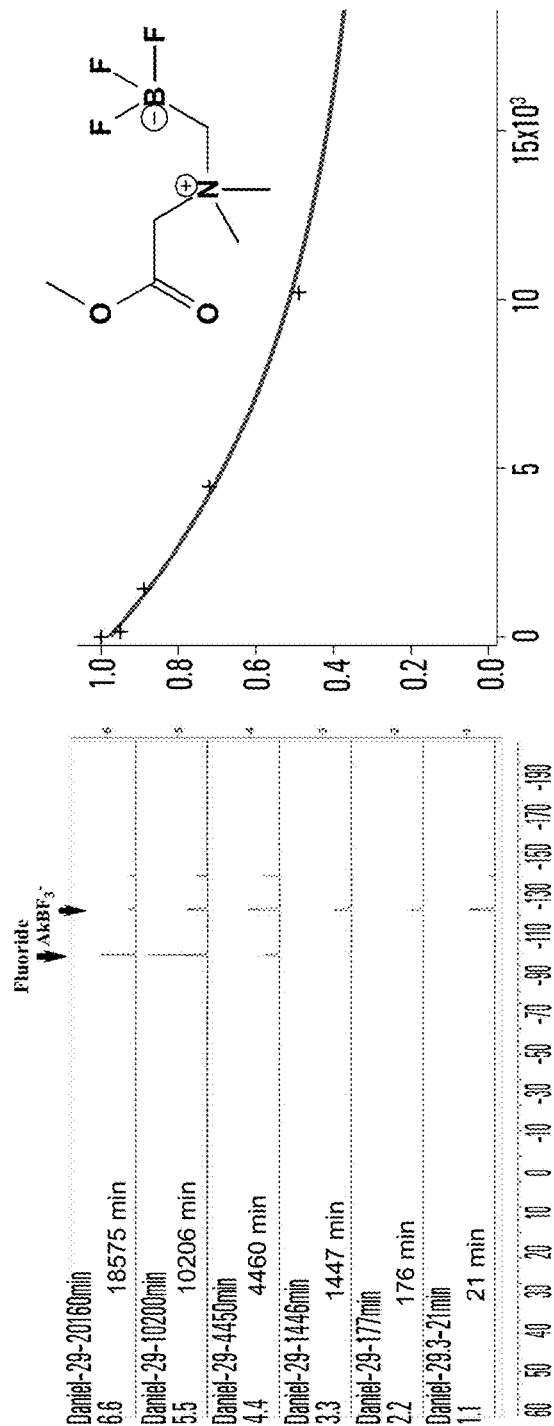
FIG. 1Y
FIG. 1Z
FIG. 1AA
FIG. 1BB

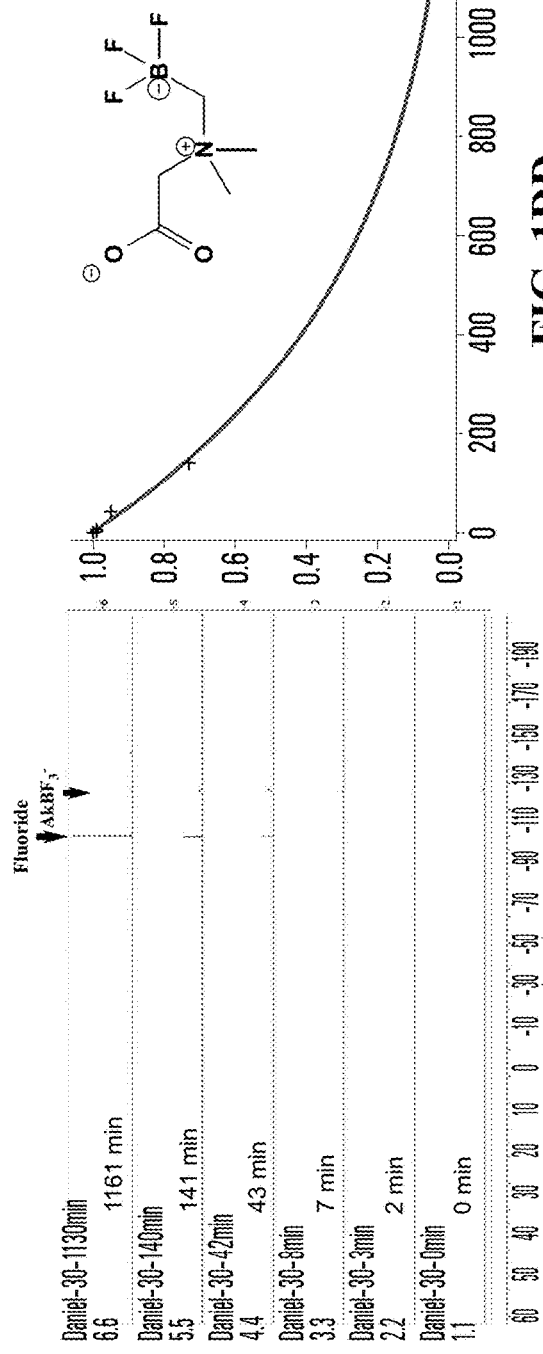
FIG. 1CC
FIG. 1DD
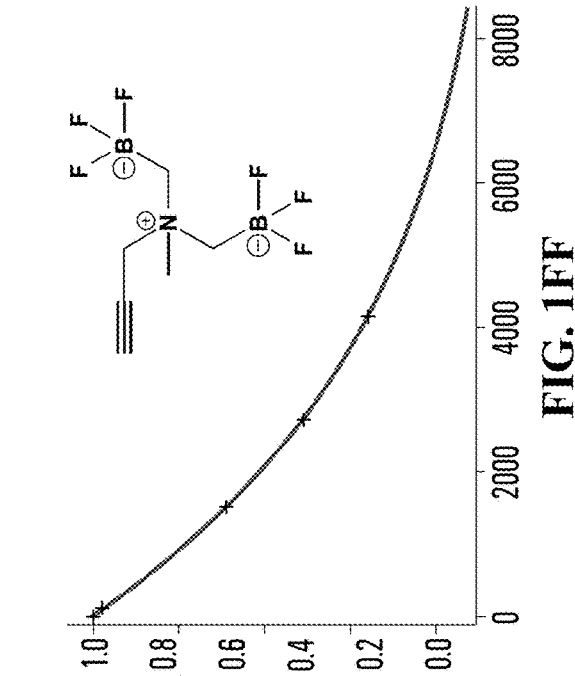
FIG. 1EE
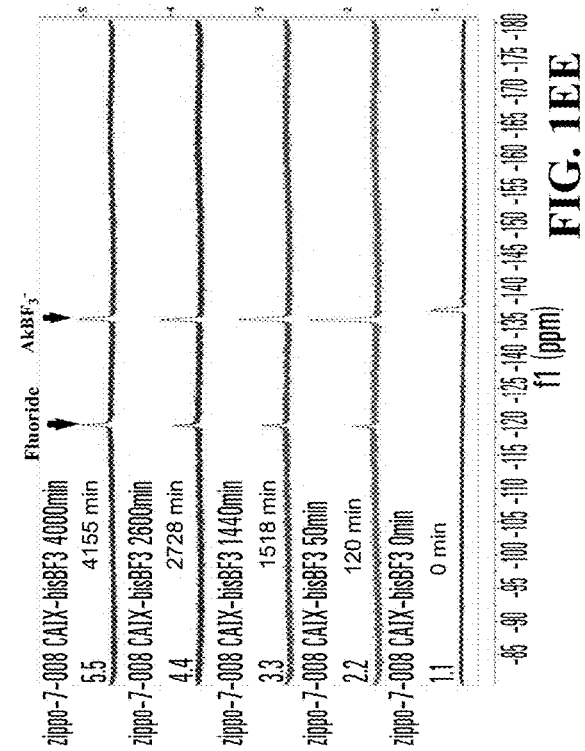
FIG. 1FF

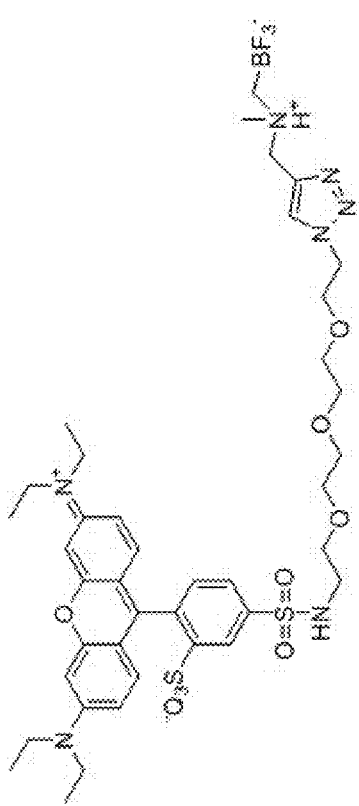
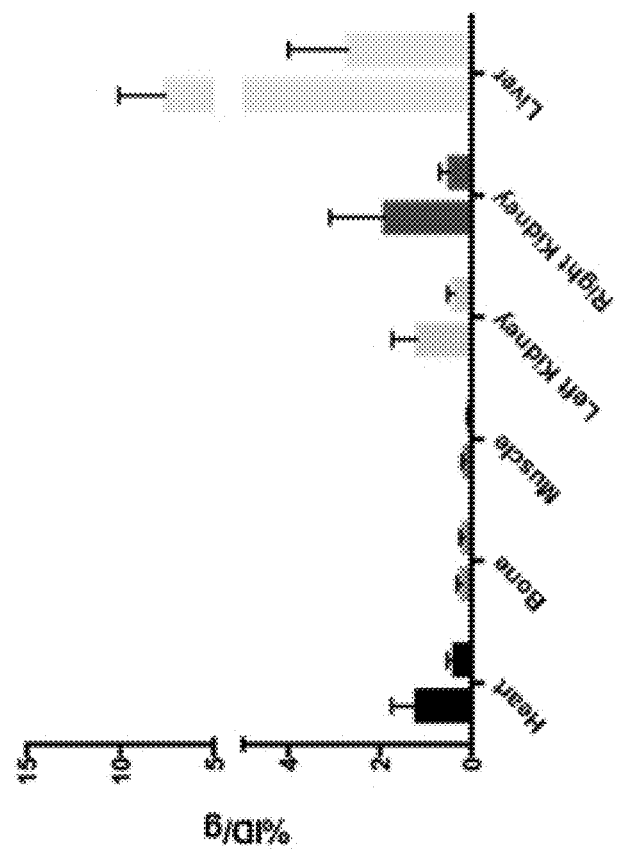
FIG. 6A
FIG. 6B

SUBSTITUTED ORGANOFLUOROBORATES AS IMAGING AGENTS

CROSS REFERENCE TO RELATED APPLICATIONS

This application is a continuation of U.S. application Ser. No. 14/773,743 filed Sep. 8, 2015, which is a national stage entry of International Patent Application No. PCT/CA2014/000200 filed Mar. 7, 2014, which claims the benefit of U.S. Provisional Application No. 61/775,280 filed Mar. 8, 2013, the contents of each of which are incorporated herein by reference.

TECHNICAL FIELD

This invention relates to the field of $^{18}$F radiolabeled reagents for use in positron emission tomography (PET) imaging.

BACKGROUND $^{18}$F is the isotope of choice for many PET cancer imaging applications.

PET imaging agents are often based on a labeled biomolecule. Examples include fluorodeoxyglucose (FDG); Octreotate, an octapeptide that is used to image cancer; and folate, which has been used to image cancer. Since the high energy particle bombardment used to produce $^{18}$F destroys complex organic molecules, $^{18}$F is first made as fluoride ion in a cyclotron and subsequently attached to the biomolecule used as the imaging agent. Also, conditions used to incorporate $^{18}$F are often too harsh for direct labeling of many biomolecules. Therefore, $^{18}$F is usually introduced into a precursor (such as an aryl fluoride) that is then subsequently appended to a larger molecule. Such multi-step procedures result in delays, with consequent loss in specific radioactivity.

Some methodologies for incorporating $^{18}$F into imaging agents have been reported, including a new approach which makes use of boron as an acceptor capable of binding several $^{18}$F atoms, thus increasing the density of positron emitters in the resulting imaging agent (see, for example, PCT publication WO 2005/0077967). In addition, the use of arylboronic acids/esters as $^{18}$F acceptors has been reported. This approach has circumvented the previous practice of generating aryl fluorides in multi-step procedures. $^{18}$F radiolabeled substituted aryl-fluoroborates for use in PET imaging have also been reported (see, for example, WO 2009/012596).

SUMMARY

A consideration in the design of PET imaging agents is the longevity of the agent itself. It is desirable that the imaging agent be sufficiently stable with respect to loss of $^{18}$F ions (termed herein as 'solvolytic de-18F-fluoridation, as quantified by the half-life at physiological pH of the chemical bond that attaches the 18F-atom to the tracer'). For example, in some applications it is desirable for the imaging agent to have a half-life with respect to solvolytic de-18F-fluoridation at physiological pH that is greater than 10 times the rate of 18F decay. In some applications it is desirable for the imaging agent to have a half-life with respect to solvolytic de-18F-fluoridation at physiological pH of around 1000 minutes or more. It is noted that the rate of solvolytic de-18F-fluoridation is a chemical process that involves bond dissociation, not radioactive decay, and therefore the rate of de-18F-fluoridation is equal to that of non-radioactive defluoridation, where the 18F-fluorine is replaced with a nonradioactive 19F-fluorine atom.

The invention described herein is based, in part, on the discovery that some organofluoroborates exhibit enhanced resistance to solvolytic de-18F-fluoridation and can be useful as PET imaging agents or precursors thereof.

An embodiment makes use of a positron emitting compound or salt thereof, wherein the compound may be of the formula I:

(I)

wherein:

B is boron;

A may be a linear or branched $C_1$-$C_{15}$ alkyl group, a linear or branched $C_1$-$C_{15}$ alkenyl, group, a linear or branched $C_1$-$C_{15}$ alkynyl group, or a $C_3$-$C_{18}$ nonaromatic cycloalkyl group, wherein each of the $C_1$-$C_{15}$ alkyl group, the linear or branched $C_1$-$C_{15}$ alkenyl group, the linear or branched $C_1$-$C_{15}$ alkynyl group, and the $C_3$-$C_{18}$ nonaromatic cycloalkyl group is unsubstituted or substituted and optionally includes at least one heteroatom interposed between two carbon atoms of the carbon chain of the group, wherein each of the at least one heteroatom is independently selected from the group consisting of O, S, N and P;

A may be joined to B through a carbon atom;

each $Y^1$ may independently be selected from the group consisting of $R^1$, $^{18}$F and $^{19}$F;

n=1 or 2;

$Y^2$ may be selected from the group consisting of $R^2$, $^{18}$F and $^{19}$F;

$R^1$ may be a noninterfering substituent with regard to fluoridation of B;

$R^2$ may be a noninterfering substituent with regard to fluoridation of B; and at least one of $(Y^1)_n$ and $Y^2$ may be $^{18}$F;

providing that A may be selected such that the $pK_a$, of $H^a$ of the acid of the formula II:

(II)

is less than or equal to about 2.8. When A is substituted at the carbon alpha to the

group with a functional group that has a dissociable proton, the dissociable proton may have a pKa greater than about 9 and contributes to a net positive charge on the functional group. Moieties, A, when selected so that:

i) the $pK_a$ of $H^a$ of the acid of the formula II:

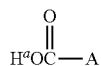

is less than or equal to 2.8; and ii) when A is substituted at the carbon alpha to the

group with a functional group that has a dissociable proton, the dissociable proton has a pKa>9 and contributes to a net positive charge on the functional group, permit the resulting fluoroborate to resist defluoridation. Half-lives with regard to solvolytic de-18F-fluoridation of the resulting organofluoroborates may be at least about 10 times longer or more than the rate of decay of 18F. In other embodiments, half-lives with regard to solvolytic de-18F-fluoridation of the resulting organofluoroborates may be at least about 1000 minutes or more; or at least about 5000 minutes or more; or at least about 10000 minutes or more; or at least about 15000 minutes or more; or at least about 20000 minutes or more; or at least about 25000 minutes or more; or at least about 50000 minutes or more; or at least about 100000 minutes or more; or at least about 125000 minutes or more; or at least about 150000 minutes or more. In some applications where loss of fluorine may be desired (e.g. in comparison of externally bound ligand that loses fluoride to the surrounding bone with internalized ligands that keep the fluoride in a targeted cell) shorter half-lives may be desirable. However, for whole body imaging, longer half-lives are desirable.

In an embodiment, one or more counterions may be present when the compound is charged.

In various embodiments, there is provided a method of making a positron emitting compound or salt thereof, the method comprising contacting an $^{18}F$ source with a compound or salt thereof, wherein the compound may be of the formula I:

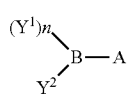

wherein:

B is boron;

A may be a linear or branched $C_1$-$C_{15}$ alkyl group, a linear or branched $C_1$-$C_{15}$ alkenyl, group, a linear or branched $C_1$-$C_{15}$ alkynyl group, or a $C_3$-$C_{18}$ nonaromatic cycloalkyl group, wherein each of the $C_1$-$C_{15}$ alkyl group, the linear or branched $C_1$-$C_{15}$ alkenyl group, the linear or branched $C_1$-$C_{15}$ alkynyl group, and the $C_3$-$C_{18}$ nonaromatic cycloalkyl group is unsubstituted or substituted and optionally includes at least one heteroatom interposed between two carbon atoms of the carbon chain of the group, wherein each of the at least one heteroatom is independently selected from the group consisting of O, S, N and P;

A may be joined to B through a carbon atom;

n=1 or 2;

each $Y^1$ may independently be selected from the group consisting of $R^1$ and a leaving group that can be displaced by 18F-fluoride;

$Y^2$ may be selected from the group consisting of $R^2$ and a leaving group that can be displaced by fluoride 18F-fluoride;

at least one of $(Y^1)_n$ and $Y^2$ may be the leaving group when n is 2;

$R^1$ may be a non-interfering substituent with regard to fluoridation of B; and $R^2$ may be a non-interfering substituent with regard to fluoridation of B; providing that A may be selected such that the $pK_a$ of $H^a$ of the acid of the formula II:

may be less than or equal to 2.8. When A is substituted at the carbon alpha to the

group with a functional group that has a dissociable proton, the dissociable proton may have a pKa greater than about 9 and contributes to a net positive charge on the functional group.

In various embodiments, there is provided a method of performing PET imaging by administering an imaging-effective amount of a positron emitting compound or salt as defined anywhere herein to a subject or object to be subjected to PET.

In various embodiments, there is provided a method of selecting a PET imaging agent or precursor thereof having resistance to solvolytic de-18F-fluoridation at physiological pH, the method comprising:

(i) providing one or more compounds or salt thereof wherein the compound may be of the formula I:

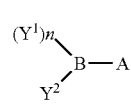

wherein:

B is boron;

A may be a linear or branched $C_1$-$C_{15}$ alkyl group, a linear or branched $C_1$-$C_{15}$ alkenyl, group, a linear or branched $C_1$-$C_{15}$ alkynyl group, or a $C_3$-$C_{18}$ nonaromatic cycloalkyl group, wherein each of the $C_1$-$C_{15}$ alkyl group, the linear or branched $C_1$-$C_{15}$ alkenyl group, the linear or branched $C_1$-$C_{15}$ alkynyl group, and the $C_3$-$C_{18}$ nonaromatic cycloalkyl group is unsubstituted or substituted and optionally includes at least one heteroatom interposed between two carbon atoms of the carbon chain of the group, wherein each of the at least one heteroatom is independently selected from the group consisting of O, S, N and P;

A may be joined to B through a carbon atom;

each $Y^1$ may independently be selected from the group consisting of $R^1$, $^{18}F$ and $^{19}F$;

n=1 or 2;

$Y^2$ may be selected from the group consisting of $R^2$, $^{18}F$ and $^{19}F$;

$R^1$ may be a noninterfering substituent with regard to fluoridation of B;

$R^2$ may be a noninterfering substituent with regard to fluoridation of B; and at least one of $(Y^1)_n$ and $Y^2$ may be $^{18}F$;

providing that A may be selected such that the $pK_a$ of $H^a$ of the acid of the formula II:

(II)

may be less than or equal to about 2.8;

(ii) assessing the half-life of the presence of the fluorine bound to B; and (iii) selecting a compound or compounds having said half-life of about 1000 minutes or more as said imaging agent or precursor thereof. When A is substituted at the carbon alpha to the

group with a functional group that has a dissociable proton, the dissociable proton may have a pKa greater than about 9 and contributes to a net positive charge on the functional group In various embodiments, there is provided a conjugate or salt thereof comprising a peptide conjugated to a positron-emitting compound or salt thereof as described above.

In various embodiments, there is provided a positron emitting compound or salt thereof as described above, or a peptide conjugated to such positron-emitting compound or salt thereof, for use as a PET imaging agent or precursor thereof.

In various embodiments, there is provided a use of a compound of formula I or salt thereof as a precursor in the manufacture of an $^{18}F$ containing PET imaging agent.

In various embodiments, the compound may be of the formula (IV):

(IV)

as defined anywhere herein, provided that when $Q^1$ is $-CR^3R^4R^5$, at least one of $R^3$, $R^4$ and $R^5$ is F, Cl, Br, I, $CX_3$, $-N^+R^{15}R^{16}R^{17}$, $-P^+R^{18}R^{19}R^{20}$, $-S^+R^{21}R^{22}$ or $-NR^{23}R^{24}$.

BRIEF DESCRIPTION OF THE DRAWINGS

FIGS. 1A, 1C, 1E, 1G, 1I, 1K, 1M, 1O, 1Q, 1S, 1U, 1W, 1Y, 1AA, 1CC, and 1EE show $^{19}F$ NMR spectral tracers for fluoridated organotrifluoroborates in 200 mM phosphate buffer pH 7.5, demonstrating the relative amount of dissociation of $^{19}F$ from the compounds at different times.

FIGS. 1B, 1D, 1F, 1H, 1J, 1L, 1N, 1P, 1R, 1T, 1V, 1X, 1Z, 1BB, 1DD, and 1FF show data for solvolytic defluoridation of the fluoridated organoborate salts from the $^{19}F$ NMR measurement plotted as a function of time. This plot can be fitted to a pseudo-first-order rate equation that provides for the calculation of a rate constant $k_{B-F}$ or alternatively referred to as $k_{solvolysis}$.

FIG. 1A shows $^{19}F$ NMR spectral traces for a certain alkynyltrifluoroborate (Compound No. 6 of Table 1).

FIG. 1B shows data for solvolytic defluoridation of Compound No. 6 of Table 1.

FIG. 1C shows $^{19}F$ NMR spectral tracers for a quaternary ammoniummethyltrifluoroborate (Compound 9 of Table 1).

FIG. 1D shows data for solvolytic defluoridation of Compound 9 of Table 1.

FIG. 1E shows $^{19}F$ NMR spectral tracers for butyltrifluoroborate (Compound No. 1 of Table 1).

FIG. 1F shows data for solvolytic defluoridation of Compound No. 1 of Table 1.

FIG. 1G shows $^{19}F$ NMR spectral tracers for vinyltrifluoroborate (Compound No. 2 of Table 1)

FIG. 1H shows data for solvolytic defluoridation of Compound No. 2 of Table 1.

FIG. 1I shows $^{19}F$ NMR spectral tracers for bromomethyltrifluoroborate (Compound No. 4 of Table 1).

FIG. 1J shows data for solvolytic defluoridation of Compound No. 4 of Table 1).

FIG. 1K shows $^{19}F$ NMR spectral tracers for a certain sulfoniumtrifluoroborate (Compound No. 11 of Table 1).

FIG. 1L shows data for solvolytic defluoridation of Compound No. 11 of Table 1.

FIG. 1M shows $^{19}F$ NMR spectral tracers for Compound No. 12 of Table 1.

FIG. 1N shows data for solvolytic defluoridation of Compound No. 12 of Table 1.

FIG. 1O shows $^{19}F$ NMR spectral tracers for phenacyltrifluoroborate (Compound No. 7 of Table 1).

FIG. 1P shows data for solvolytic defluoridation of Compound No. 7 of Table 1.

FIG. 1Q shows $^{19}F$ NMR spectral tracers for benzoytrifluoroborate (Compound No. 8 of Table 1).

FIG. 1R shows data for solvolytic defluoridation of Compound No. 8 of Table 1.

FIG. 1S shows $^{19}F$ NMR spectral tracers for pyridiniummethyltrifluoroborate (Compound No. 13 of Table 1).

FIG. 1T shows data for solvolytic defluoridation of Compound No. 13 of Table 1.

FIG. 1U shows $^{19}F$ NMR spectral tracers for Compound No. 9 of Table 1.

FIG. 1V shows data for solvolytic defluoridation of Compound No. 9 of Table 1.

FIG. 1W shows $^{19}F$ NMR spectral tracers for dichloromethyltrifluoroborate (Compound No. 10 of Table 1).

FIG. 1X shows data for solvolytic defluoridation of Compound No. 10 of Table 1).

FIG. 1Y shows $^{19}F$ NMR spectral tracers for Compound No. 14 of Table 1.

FIG. 1Z shows data for solvolytic defluoridation of Compound No. 14 of Table 1).

FIG. 1AA shows $^{19}F$ NMR spectral tracers for Compound No. 15 of Table 1.

FIG. 1BB shows data for solvolytic defluoridation of Compound No. 15 of Table 1.

FIG. 1CC shows $^{19}F$ NMR spectral tracers for Compound No. 16 of Table 1.

FIG. 1DD shows data for solvolytic defluoridation of Compound No. 16 of Table 1.

FIG. 1EE shows $^{19}F$ NMR spectral tracers for Compound No. 17 of Table 1.

FIG. 1FF shows data for solvolytic defluoridation of Compound No. 17 of Table 1.

FIG. 6A shows a histogram indicated the uptake value of different organs for Compound 19 at 60 min post injection.

FIG. 6B shows a PET/CT image of a mouse injected with Compound 19 at 60 min post injection.

DETAILED DESCRIPTION

Figure 1A:
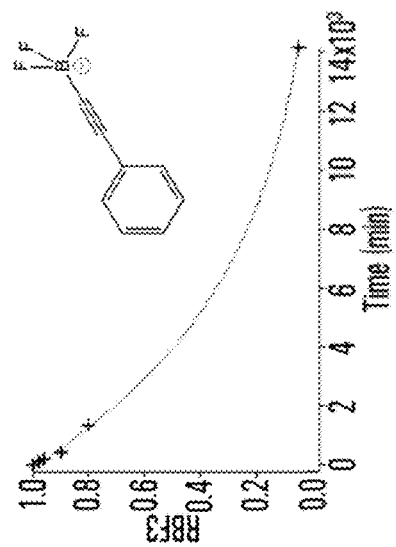
Figure 1C:
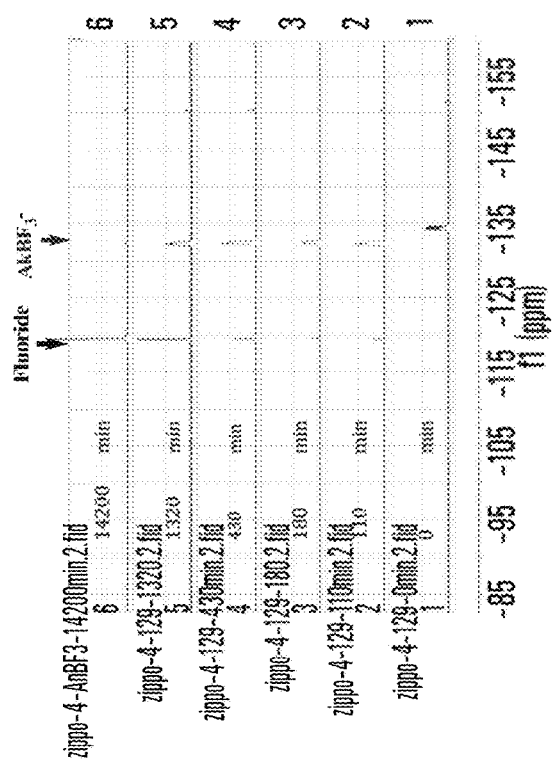

Any terms not directly defined herein shall be understood to have the meanings commonly associated with them as understood within the art of the invention. Certain terms are discussed below, or elsewhere in the specification, to provide additional guidance to the practitioner in describing the devices, methods and embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it may be explicitly stated. Use of examples in the specification, including examples of terms, may be for illustrative purposes only and does not limit the scope and meaning of the embodiments of the invention herein.

"Fluoridation" or "fluorination" are used synonymously herein to refer generally to a chemical reaction by which fluorine is introduced into a compound.

As used herein, the symbol 'pKa' is normally understood to a person skilled in the art and refers to the logarithmic constant, pKa, where pKa=-$\log_{10}$Ka. The symbol 'Ka' refers to an acid dissociation constant, which is the equilibrium constant for the proton-transfer reaction between a weak acid, HA, and water, $H_2O$. The acid dissociation constant, Ka, for a monoprotic acid, HA, is given by the expression Ka=[$A^-$][$H_3O^+$]/[HA].

As used herein, the phrase '$C_x$-$C_y$ alkyl' group may be used as it is normally understood to a person of skill in the art and often refers to a chemical entity that has a carbon skeleton or main carbon chain comprising a number from x to y (with all individual integers within the range included, including integers x and y) of carbon atoms. For example a '$C_1$-$C_{15}$ alkyl' group may be a chemical entity that has 1, 2, 3, 4, 5, 6, 7, 8, 9, 10, 11, 12, 13, 14 or 15 carbon atom(s) in its carbon skeleton or main chain.

As used herein, the term 'linear' may be used as it is normally understood to a person of skill in the art and often refers to a chemical entity that comprises a skeleton or main chain that does not split off into more that one contiguous chain. Non-limiting examples of linear alkyls include methyl, ethyl, n-propyl, and n-butyl.

As used herein, the term 'branched' may be used as it is normally understood to a person of skill in the art and often refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

A linear or branched $C_1$-$C_{15}$ alkyl group may include a linear or branched saturated $C_1$-$C_{15}$ alkyl group, a linear or branched $C_2$-$C_{15}$ alkenyl group and a linear or branched $C_2$-$C_{15}$ alkynyl group. As used herein, the term 'saturated' when referring to a chemical entity may be used as it is normally understood to a person of skill in the art and often refers to a chemical entity that comprises only single bonds. Non-limiting examples of saturated $C_1$-$C_{15}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, 1-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl and t-decyl. Non-limiting examples of $C_2$-$C_{15}$ alkenyl group may include vinyl, allyl, isopropenyl, 1-propene-2-yl, 1-butene-1-yl, 1-butene-2-yl, 1-butene-3-yl, 2-butene-1-yl, 2-butene-2-yl, octenyl and decenyl. Non-limiting examples of $C_2$-$C_{15}$ alkynyl group may include ethynyl, propynyl, butynyl, pentynyl, hexynyl, heptynyl, octynyl, nonynyl and decynyl. The saturated $C_1$-$C_{15}$ alkyl group, $C_2$-$C_{15}$ alkenyl group or $C_2$-$C_{15}$ alkynyl group may be, for example, and without limitation, interrupted by one or more heteroatoms which may independently be nitrogen, sulfur, oxygen or phosphorus.

As used herein, the term '$C_x$-$C_y$ cycloalkyl' group may be used as it is normally understood to a person of skill in the art and often refers to a compound or a chemical entity in which at least a portion of the carbon skeleton or main chain of the chemical entity may be bonded in such a way so as to form a 'loop', circle or ring of atoms that are bonded together. The atoms do not have to all be directly bonded to each other, but rather may be directly bonded to as few as two other atoms in the 'loop'. As used herein, $C_3$-$C_{18}$ cycloalkyl group may include a non-aromatic $C_3$-$C_{18}$ cycloalkyl group and an aromatic $C_3$-$C_{18}$ cycloalkyl group.

A $C_3$-$C_{18}$ cycloalkyl group may include, for example, and without limitation, a saturated $C_3$-$C_{18}$ cycloalkyl group, a $C_3$-$C_{18}$ cycloalkenyl group, a $C_3$-$C_{18}$ cycloalkynyl group, a $C_3$-$C_{18}$ aryl group, a $C_3$-$C_{18}$ non-aromatic heterocyclic group containing one or more heteroatoms which may independently be nitrogen, sulfur, phosphorus or oxygen, and a $C_3$-$C_{18}$ aromatic heterocyclic group containing one or more heteroatoms which may independently be nitrogen, sulfur, phosphorus or oxygen. Non-limiting examples of the saturated $C_3$-$C_{18}$ cycloalkyl group may include cyclopropanyl, cyclobutanyl, cyclopentanyl, cyclohexanyl, cycloheptanyl, cyclooctanyl, cyclononanyl and cyclodecanyl. Non-limiting examples of the $C_3$-$C_{18}$ cycloalkenyl group may include cyclopropenyl, cyclobutenyl, cyclopentenyl, cyclohexenyl, cycloheptenyl, cyclooctenyl, cyclononanenyl and cyclodecanenyl. Non-limiting examples of the $C_3$-$C_{18}$ aryl group may include phenyl (Ph), pentalenyl, indenyl, naphthyl, and azulenyl.

Non-limiting examples of the $C_3$-$C_{18}$ non-aromatic heterocyclic group may include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl and succinimidyl, oxiranyl, tetrahydropyranyl, oxetanyl, dioxanyl, thietanyl, thiepinyl, morpholinyl, and oxathiolanyl. Non-limiting examples of the $C_3$-$C_{18}$ aromatic heterocyclic group may include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, and isoxazolyl.

As used herein, the term 'substituted' may be used as it is normally understood to a person of skill in the art and often refers to a chemical entity that has one chemical group replaced with a different chemical group that contains one or more heteroatoms. Unless otherwise specified, a substituted alkyl may be an alkyl in which one or more hydrogen atom(s) may be/are replaced with one or more atom(s) that may be/are not hydrogen(s). For example, chloromethyl may be a non-limiting example of a substituted alkyl, more particularly an example of a substituted methyl. Aminoethyl may be another non-limiting example of a substituted alkyl, more particularly it may be a substituted ethyl.

As used herein, the term 'unsubstituted' may be used as it may be normally understood to a person of skill in the art and often refers to a chemical entity that may be a hydrocarbon and/or does not contain a heteroatom. Non-limiting examples of unsubstituted alkyls include methyl, ethyl, tert-butyl, and pentyl.

"Intercepted", as used herein with respect to the positioning heteroatoms, pertains to a carbon chain in which a heteroatom is interposed between two carbon atoms of the carbon chain.

In an embodiment, the compound may be of the formula I:

wherein each of B, A, $Y^1$, n, $Y^2$, $R^1$, and $R^2$ may be as defined anywhere herein.

In further embodiments, A may be selected such that the pKa of $H^a$ of the acid of the formula II:

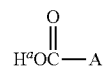

may be less than or equal to 5.0, less than or equal to 4.5, less than or equal to 4.0, less than or equal to 3.5, less than or equal to 3.0, less than or equal to 2.9, less than or equal to 2.8, less than or equal to 2.7, less than or equal to 2.6, less than or equal to 2.5, less than or equal to 2.4, less than or equal to 2.3, less than or equal to 2.2, less than or equal to 2.1, less than or equal to 2.0, less than or equal to 1.9, less than or equal to 1.8, less than or equal to 1.7, less than or equal to 1.96, less than or equal to 1.5, less than or equal to 1.4, less than or equal to 1.3, less than or equal to 1.2, less than or equal to 1.1, less than or equal to 1.0, less than or equal to 0.9, less than or equal to 0.8, less than or equal to 0.6, less than or equal to 0.4, or less than or equal to 0.2. When A is substituted at the carbon alpha to the

group with a functional group that has a dissociable proton, the dissociable proton has a pKa>9 and contributes to a net positive charge on the functional group.

In further embodiments, A may be selected such that the pKa of $H^a$ of the acid of the formula II:

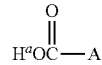

may be from 0.2 to 0.4, 0.2 to 0.6, 0.2 to 0.8, 0.2 to 1.0, 0.2 to 1.2, 0.2 to 1.4, 0.2 to 1.8, 0.2 to 2.0, 0.2 to 2.2, 0.2 to 2.4, 0.2 to 2.6, 0.2 to 2.8, 0.2 to 2.9, 0.4 to 2.4, 0.6 to 2.4, 0.8 to 2.4, 1.0 to 2.4, 1.2 to 2.4, 1.4 to 2.4, 1.6 to 2.4, 1.8 to 2.4, 2.0 to 2.4, or 2.2 to 2.4. When A is substituted at the carbon alpha to the

group with a functional group that has a dissociable proton, the dissociable proton has a pKa>9 and contributes to a net positive charge on the functional group.

In various embodiments, the positron emitting compound or salt may have a solvolytic de-18F-fluoridation half-life at physiological pH of about 1000 minutes or more, about 5000 minutes or more, about 10000 minutes or more, about 15000 minutes or more, about 20000 minutes or more, about 25000 minutes or more, about 50000 minutes or more, about 100000 minutes or more, about 125000 minutes or more, about 150000 minutes or more, or about 200000 minutes or more. In various embodiments, the positron emitting compound or salt may have a solvolytic de-18F-fluoridation half-life at physiological pH from about 1000 minutes to about 200000 minutes, from about 5000 minutes to about 200000 minutes, from about 10000 minutes to about 200000 minutes, from about 15000 minutes to about 200000 minutes, from about 20000 minutes to about 200000 minutes, from about 25000 minutes to about 200000 minutes, from about 50000 minutes to about 200000 minutes, from about 100000 minutes to about 200000 minutes, from about 125000 minutes to about 200000 minutes, or from about 150000 minutes to about 200000 minutes.

In various embodiments, the compound may be of the formula (I), wherein A may be substituted with one or more substituents selected from the group consisting of F, Cl, Br, I, $N^+(C_{1-15}alkyl)_3$, $—N^+(C_{2-15}alkenyl)_3$, $—N^+(C_{2-15}alkynyl)_3$, $N^+H(C_{1-15}alkyl)_2$, $—N^+H(C_{2-15}alkenyl)_2$, $—N^+H(C_{2-15}alkynyl)_2$, $P^+(C_{1-15}alkyl)_3$, $P^+(C_{2-15}alkenyl)_3$, $P^+(C_{2-15}alkynyl)_3$, $S^+(C_{1-15}alkyl)_2$, $S^+(C_{2-15}alkenyl)_2$, $S^+(C_{2-15}alkynyl)_2$, oxo (i.e., =O), OH, $—OC_{1-15}alkyl$, unsubstituted or substituted aromatic $C_3$-$C_{18}$ cycloalkyl, unsubstituted or substituted non-aromatic $C_3$-$C_{15}$ heterocyclic group, unsubstituted or substituted aromatic $C_3$-$C_{18}$ heterocyclic group, =NH, $—C_1$-$C_{15}alkyl$, non-aromatic $C_3$-$C_{18}$ cycloalkyl, $—N(C_{1-15}alkyl)_2$, $—N(C_{2-15}alkenyl)_2$, $—N(C_{2-15}alkynyl)_2$, $—COOH$, $—NH_2$, $—SH$, a biomolecule, and a linking group optionally joined to a biomolecule. In various embodiments, A may be substituted with one or more substituents selected from the group consisting of F, Cl, Br, I, $—N^+(C_{1-15}alkyl)_3$, $—N^+(C_{2-15}alkenyl)_3$, $—N^+(C_{2-15}alkynyl)_3$, $—N^-H(C_{1-15}alkyl)_2$, $—N^+H(C_{2-15}alkenyl)_2$, $—N^+H(C_{2-15}alkynyl)_2$, $P^+(C_{1-15}alkyl)_3$, $P^+(C_{2-15}alkenyl)_3$, $P^+(C_{2-15}alkynyl)_3$, oxo (i.e., =O), OH, unsubstituted or substituted aromatic $C_3$-$C_{18}$ cycloalkyl, unsubstituted or substituted non-aromatic $C_3$-$C_{18}$ heterocyclic group, unsubstituted or substituted aromatic $C_3$-$C_{18}$ heterocyclic group, =NH, $—C_1$-$C_{15}alkyl$, non-aromatic $C_3$-$C_{18}$ cycloalkyl, $—N(C_{1-15}alkyl)_2$, $—N(C_{2-15}alkenyl)_2$, $—N(C_{2-15}alkynyl)_2$, $—COOH$, $—NH_2$, $—SH$, a biomolecule, and a linking group optionally joined to a biomolecule. In various embodiments, A may be substituted with one or more substituents selected from the group consisting of F, Cl, Br, I, $—N^+(C_{1-15}alkyl)_3$, $—N^+(C_{2-15}alkenyl)_3$, $—N^+(C_{2-15}alkynyl)_3$, $—N^+H(C_{1-15}alkyl)_2$, $—N^+H(C_{2-15}alkenyl)_2$, $—N^+H(C_{2-15}alkynyl)_2$, $P^+(C_{1-15}alkyl)_3$, $P^+(C_{2-15}alkenyl)_3$, $P^+(C_{2-15}alkynyl)_3$, oxo (i.e., =O), OH, unsubstituted or substituted aromatic $C_3$-$C_{18}$ cycloalkyl, unsubstituted or substituted non-aromatic $C_3$-$C_{18}$ heterocyclic group, unsubstituted or substituted aromatic $C_3$-$C_{18}$ heterocyclic group, $—C_1$-$C_{15}alkyl$, non-aromatic $C_3$-$C_{18}$ cycloalkyl, $—N(C_{1-15}alkyl)_2$, $—N(C_{2-15}alkenyl)_2$, $—N(C_{2-15}alkynyl)_2$, $—COOH$, $—NH_2$, $—SH$, a biomolecule, and a linking group optionally joined to a biomolecule. In various embodiments, A may be substituted with at least one substituent that may be a biomolecule or a linking group optionally joined to a biomolecule.

In various embodiments, the compound may be of the formula (IV):

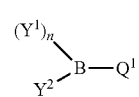
(IV)

wherein $Q^1$ may be $—CR^3R^4R^5$, $—C\equiv CR^8$,

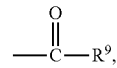

or $—R^{10}C=CR^{11}R^{12}$; and each of $R^3$, $R^4$, $R^5$, $R^8$, $R^9$, $R^{10}$, $R^{11}$, and $R^{12}$ may be as defined anywhere herein. In various embodiments, $Q^1$ may be $—CR^3R^4R^5$, or $—R^{10}C=CR^{11}R^{12}$; and each of $R^3$, $R^4$, $R^5$, $R^8$, $R^{10}$, $R^{11}$, and $R^{12}$ may be as defined anywhere herein. In various embodiments, $Q^1$ may be $—CR^3R^4R^5$,

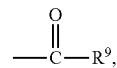

or $—R^{10}C=CR^{11}R^{12}$; and each of $R^3$, $R^4$, $R^5$, $R^9$, $R^{10}$, $R^{11}$, and $R^{12}$ may be as defined anywhere herein. In various embodiments, $Q^1$ may be $—C\equiv CR^8$,

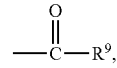

or $—R^{10}C=CR^{11}R^{12}$; and each of $R^8$, $R^9$, $R^{10}$, $R^{11}$, and $R^{12}$ may be as defined anywhere herein. In various embodiments, $Q^1$ may be $—CR^3R^4R^5$ or

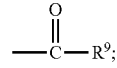

and each of $R^3$, $R^4$, $R^5$, and $R^9$ may be as defined anywhere herein. In various embodiments, $Q^1$ may be $—CR^3R^4R^5$ or $—R^{10}C\equiv CR^{11}R^{12}$; and each of $R^3$, $R^4$, $R^5$, $R^{10}$, $R^{11}$, and $R^{12}$ may be as defined anywhere herein. In an embodiment, $Q^1$ may be $—C\equiv CR^8$ or

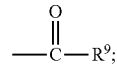

and each of $R^8$ and $R^9$ may be as defined anywhere herein. In an embodiment, $Q^1$ may be $—C\equiv CR^8$ or $—R^{10}C=CR^{11}R^{12}$; and each of $R^8$, $R^{10}$, $R^{11}$, and $R^{12}$ may be as defined anywhere herein. In various embodiments, $Q^1$ may be

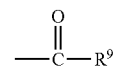

or $—R^{10}C=CR^{11}R^{12}$; and each of $R^9$, $R^{10}$, $R^{11}$, and $R^{12}$ may be as defined anywhere herein. In an embodiment, $Q^1$ may be

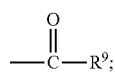

and $R^9$ may be as defined anywhere herein. In an embodiment, $Q^1$ may be —$R^{10}C$=$CR^{11}R^{12}$; and each of $R^{10}$, $R^{11}$, and $R^{12}$ may be as defined anywhere herein. In various embodiments, $Q^1$ may be —$CR^3R^4R^5$, —C≡$CR^8$, or

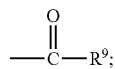

and each of $R^3$, $R^4$, $R^5$, $R^8$, and $R^9$ may be as defined anywhere herein. In an embodiment, $Q^1$ may be —$CR^3R^4R^5$ or —C≡$CR^8$; and each of $R^3$, $R^4$, $R^5$, and $R^8$ may be as defined anywhere herein. In an embodiment, $Q^1$ may be —C≡$CR^8$; and $R^8$ may be as defined anywhere herein. In various embodiments, $Q^1$ may be —$CR^3R^4R^5$; and each of $R^3$, $R^4$, and $R^5$ may be as defined anywhere herein.

In various embodiments, the compound may be of the formula (IV):

(IV)

wherein $Q^1$ may be —$CR^3R^4R^5$; and each of $R^3$, $R^4$, and $R^5$ may be as defined anywhere herein. Each of $R^3$, $R^4$, and $R^5$ may independently be H, D, F, Cl, Br, I, $CX_3$, —$N^+R^{15}R^{16}R^{17}$, —$P^+R^{18}R^{19}R^{20}$, —$S^+R^{21}R^{22}$, —$NR^{23}R^{24}$, $NHR^{23}$, $NHR^{23}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{15}$, $R^{16}$, $R^{17}$, $R^{18}$, $R^{19}$, $R^{20}$, $R^{21}$, $R^{22}$, $R^{23}$ and $R^{24}$ may be as defined anywhere herein; at least one of $R^3$, $R^4$ and $R^5$ may be F, Cl, Br, I, $CX_3$, —$N^+R^{15}R^{16}R^{17}$, —$P^+R^{18}R^{19}R^{20}$, —$S^+R^{21}R^{22}$ or —$NR^{23}R^{24}$; $NHR^{23}$; and at least one of $R^3$, $R^4$, $R^5$, $R^{15}$, $R^{16}$, $R^{17}$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be —$N^+R^{15}R^{16}R^{17}$, —$P^+R^{18}R^{19}R^{20}$, —$S^+R^{21}R^{22}$, or —$NR^{23}R^{24}$, and at least one of $R^3$, $R^4$, $R^5$, $R^{15}$, $R^{16}$, $R^{17}$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be —$N^+R^{15}R^{16}R^{17}$, —$P^+R^{18}R^{19}R^{20}$, —$S^+R^{21}R^{22}$, or —$NR^{23}R^{24}$; and at least one of $R^3$, $R^4$, $R^5$, $R^{15}$, $R^{16}$, $R^{17}$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, F, Cl, Br, I, $CX_3$, —$N^+R^{15}R^{16}R^{17}$, —$P^+R^{18}R^{19}R^{20}$, —$S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{15}$, $R^{16}$, $R^{17}$, $R^{18}$, $R^{19}$, $R^{20}$, $R^{21}$ and $R^{22}$ may be as defined anywhere herein; at least one of $R^3$, $R^4$ and $R^5$ may be F, Cl, Br, I, $CX_3$, —$N^+R^{15}R^{16}R^{17}$, —$P^+R^{18}R^{19}R^{20}$, or —$S^+R^{21}R^{22}$; and at least one of $R^3$, $R^4$, $R^5$, $R^{15}$, $R^{16}$, $R^{17}$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be —$N^+R^{15}R^{16}R^{17}$, —$P^+R^{18}R^{19}R^{20}$, or —$S^+R^{21}R^{22}$; and at least one of $R^3$, $R^4$, $R^5$, $R^{15}$, $R^{16}$, $R^{17}$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be —$N^+R^{15}R^{16}R^{17}$, —$P^+R^{18}R^{19}R^{20}$, or —$S^+R^{21}R^{22}$; and at least one of $R^3$, $R^4$, $R^5$, $R^{15}$, $R^{16}$, $R^{17}$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, F, Cl, Br, I, $CX_3$, —$N^+R^{15}R^{16}R^{17}$, —$P^+R^{18}R^{19}R^{20}$, —$NR^{23}R^{24}$, $NHR^{23}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{15}$, $R^{16}$, $R^{17}$, $R^{18}$, $R^{19}$, $R^{20}$, $R^{23}$ and $R^{24}$ may be as defined anywhere herein; at least one of $R^3$, $R^4$ and $R^5$ may be F, Cl, Br, I, $CX_3$, —$N^+R^{15}R^{16}R^{17}$, —$P^+R^{18}R^{19}R^{20}$, or —$NR^{23}R^{24}$; and at least one of $R^3$, $R^4$, $R^5$, $R^{15}$, $R^{16}$, $R^{17}$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be $-N^+R^{15}R^{16}R^{17}$, $-P^+R^{18}R^{19}R^{20}$, or $-NR^{23}R^{24}$; and at least one of $R^3$, $R^4$, $R^5$, $R^{15}$, $R^{16}$, $R^{17}$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be $-N^+R^{15}R^{16}R^{17}$, $-P^+R^{18}R^{19}R^{20}$, or $-NR^{23}R^{24}$; and at least one of $R^3$, $R^4$, $R^5$, $R^{15}$, $R^{16}$, $R^{17}$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, F, Cl, Br, I, $CX_3$, $-N^+R^{15}R^{16}R^{17}$, $-S^+R^{21}R^{22}$, $-NR^{23}R^{24}$, $NHR^{23}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{15}$, $R^{16}$, $R^{17}$, $R^{21}$, $R^{22}$, $R^{23}$ and $R^{24}$ may be as defined anywhere herein; at least one of $R^3$, $R^4$ and $R^5$ may be F, Cl, Br, I, $CX_3$, $-N^+R^{15}R^{16}R^{17}$, $-S^+R^{21}R^{22}$ or $-NR^{23}R^{24}$; and at least one of $R^3$, $R^4$, $R^5$, $R^{15}$, $R^{16}$, $R^{17}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be $-N^+R^{15}R^{16}R^{17}$, $-S^+R^{21}R^{22}$ or $-NR^{23}R^{24}$; and at least one of $R^3$, $R^4$, $R^5$, $R^{15}$, $R^{16}$, $R^{17}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be $-N^+R^{15}R^{16}R^{17}$, $-S^+R^{21}R^{22}$ or $-NR^{23}R^{24}$; and at least one of $R^3$, $R^4$, $R^5$, $R^{15}$, $R^{16}$, $R^{17}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, F, Cl, Br, I, $CX_3$, $-P^+R^{18}R^{19}R^{20}$, $-S^+R^{21}R^{22}$, $-NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{18}$, $R^{19}$, $R^{20}$, $R^{21}$, $R^{22}$, $R^{23}$ and $R^{24}$ may be as defined anywhere herein; at least one of $R^3$, $R^4$ and $R^5$ may be F, Cl, Br, I, $CX_3$, $-P^+R^{18}R^{19}R^{20}$, $-S^+R^{21}R^{22}$ or $-NR^{23}R^{24}$; and at least one of $R^3$, $R^4$, $R^5$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be $-P^+R^{18}R^{19}R^{20}$, $-S^+R^{21}R^{22}$ or $-NR^{23}R^{24}$; and at least one of $R^3$, $R^4$, $R^5$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be $-P^+R^{18}R^{19}R^{20}$, $-S^+R^{21}R^{22}$ or $-NR^{23}R^{24}$; and at least on of $R^3$, $R^4$, $R^5$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, $-N^+R^{15}R^{16}R^{17}$, $-P^+R^{18}R^{19}R^{20}$, $-S^+R^{21}R^{22}$, $-NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each of $R^{15}$, $R^{16}$, $R^{17}$, $R^{18}$, $R^{19}$, $R^{20}$, $R^{21}$, $R^{22}$, $R^{23}$ and $R^{24}$ may be as defined anywhere herein; at least one of $R^3$, $R^4$ and $R^5$ may be $-N^+R^{15}R^{16}R^{17}$, $-P^+R^{18}R^{19}R^{20}$, $-S^+R^{21}R^{22}$ or $-NR^{23}R^{24}$; and at least one of $R^3$, $R^4$, $R^5$, $R^{15}$, $R^{16}$, $R^{17}$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be $-N^+R^{15}R^{16}R^{17}$, $-P^+R^{18}R^{19}R^{20}$, $-S^+R^{21}R^{22}$ or $-NR^{23}R^{24}$; and at least one of $R^3$, $R^4$, $R^5$, $R^{15}$, $R^6$, $R^{17}$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, F, Cl, Br, I, $CX_3$, $-N^+R^{15}R^{16}R^{17}$, $-P^+R^{18}R^{19}R^{20}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{15}$, $R^{16}$, $R^{17}$, $R^{18}$, $R^{19}$, and $R^{20}$ may be as defined anywhere herein; at least one of $R^3$, $R^4$ and $R^5$ may be F, Cl, Br, I, $CX_3$, $-N^+R^{15}R^{16}R^{17}$, or $-P^+R^{18}R^{19}R^{20}$; and at least on of $R^3$, $R^4$, $R^5$, $R^{15}$, $R^{16}$, $R^{17}$, $R^{18}$, $R^{19}$, and $R^{20}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be $-N^+R^{15}R^{16}R^{17}$, or $-P^+R^{18}R^{19}R^{20}$; and at least one of $R^3$, $R^4$, $R^5$, $R^{15}$, $R^{16}$, $R^{17}$, $R^{18}$, $R^{19}$, and $R^{20}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be $-N^+R^{15}R^{16}R^{17}$, or $-P^+R^{18}R^{19}R^{20}$; and at least one of $R^3$, $R^4$, $R^5$, $R^{15}$, $R^{16}$, $R^{17}$, $R^{18}$, $R^{19}$, and $R^{20}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, F, Cl, Br, I, $CX_3$, $-N^+R^{15}R^{16}R^{17}$, $-S^-R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{15}$, $R^{16}$, $R^{17}$, $R^{21}$ and $R^{22}$ may be as defined anywhere herein; at least one of $R^3$, $R^4$ and $R^5$ may be F, Cl, Br, I, $CX_3$, $-N^+R^{15}R^{16}R^{17}$, or $-S^+R^{21}R^{22}$; and at least one of $R^3$, $R^4$, $R^5$, $R^{15}$, $R^{16}$, $R^{17}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be $-N^+R^{15}R^{16}R^{17}$, or $-S^+R^{21}R^{22}$; and at least one of $R^3$, $R^4$, $R^5$, $R^{15}$, $R^{16}$, $R^{17}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be $-N^+R^{15}R^{16}R^{17}$, or $-S^+R^{21}R^{22}$; and at least one of $R^3$, $R^4$, $R^5$, $R^{15}$, $R^{16}$, $R^{17}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, F, Cl, Br, I, $CX_3$, $-N^+R^{15}R^{16}R^{17}$; $-NR^{23}R^{24}$, $NHR^{23}$, a biomolecule, a linking group optionally joined to, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{15}$, $R^{16}$, $R^{17}$, $R^{23}$ and $R^{24}$ may be as defined anywhere herein; at least one of $R^3$, $R^4$ and $R^5$ may be F, Cl, Br, I, $CX_3$, $-N^+R^{15}R^{16}R^{17}$, or $-NR^{23}R^{24}$; and at least one of $R^3$, $R^4$, $R^5$, $R^{15}$, $R^{16}$, $R^{17}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be $-N^+R^{15}R^{16}R^{17}$, $-NR^{23}R^{24}$, or $NHR^{23}$; and at least one of $R^3$, $R^4$, $R^5$, $R^{15}$, $R^{16}$, $R^{17}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be $-N^+R^{15}R^{16}R^{17}$, or $-NR^{23}R^{24}$; and at least one of $R^3$, $R^4$, $R^5$, $R^{15}$, $R^{16}$, $R^{17}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, F, Cl, Br, I, $CX_3$, $-P^+R^{18}R^{19}R^{20}$, $-S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{15}$ cycloalkyl group may be joined to the carbon atom of $-CR^3R^4R^5$ through a carbon atom; each X may be the same or different and may be F, Cl, Br, or I; each of $R^{18}$, $R^{19}$, $R^{20}$, $R^{21}$ and $R^{22}$ may be as defined anywhere herein; at least one of $R^3$, $R^4$ and $R^5$ may be F, Cl, Br, I, $CX_3$, $-P^+R^{18}R^{19}R^{20}$, or $-S^-R^{21}R^{22}$; and at least one of $R^3$, $R^4$, $R^5$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be $-P^+R^{18}R^{19}R^{20}$, or $-S^+R^{21}R^{22}$; and at least one of $R^3$, $R^4$, $R^5$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be $-P^+R^{18}R^{19}R^{20}$, or $-S^+R^{21}R^{22}$; and at least one of $R^3$, $R^4$, $R^5$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule.

In various embodiments, each of $R^3$, $R^4$, and $R^5$ may independently be H, D, F, Cl, Br, I, $CX_3$, $-P^+R^{18}R^{19}R^{20}$, $-NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{18}$, $R^{19}$, $R^{20}$, $R^{23}$ and $R^{24}$ may be as defined anywhere herein; at least one of $R^3$, $R^4$ and $R^5$ may be F, Cl, Br, I, $CX_3$, —$P^+R^{18}R^{19}R^{20}$, or —$NR^{23}R^{24}$ and at least one of $R^3$, $R^4$, $R^5$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be —$P^+R^{18}R^{19}R^{20}$, or $NR^{23}R^{24}$ and at least one of $R^3$, $R^4$, $R^5$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be —$P^+R^{18}R^{19}R^{20}$, or —$NR^{23}R^{24}$; and at least one of $R^3$, $R^4$, $R^5$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule.

In various embodiments, each of $R^3$, $R^4$, and $R^5$ may independently be H, D, F, Cl, Br, I, $CX_3$, —$S^+R^{21}R^{22}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{21}$, $R^{22}$, $R^{23}$ and $R^{24}$ may be as defined anywhere herein; at least one of $R^3$, $R^4$ and $R^5$ may be F, Cl, Br, I, $CX_3$, —$S^+R^{21}R^{22}$ or —$NR^{23}R^{24}$; and at least one of $R^3$, $R^4$, $R^5$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be —$S^+R^{21}R^{22}$ or —$NR^{23}R^{24}$; and at least one of $R^3$, $R^4$, $R^5$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be —$S^+R^{21}R^{22}$ or —$NR^{23}R^{24}$; and at least one of $R^3$, $R^4$, $R^5$, $R^{21}$, $R^{22}$, $R^{23}$, and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, —$N^+R^{15}R^{16}R^{17}$, —$P^+R^{18}R^{19}R^{20}$, —$S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$, $R^{17}$, $R^{18}$, $R^{19}$, $R^{20}$, $R^{21}$ and $R^{22}$ may be as defined anywhere herein; at least one of $R^3$, $R^4$ and $R^5$ may be —$N^+R^{15}R^{16}R^{17}$, —$P^+R^{18}R^{19}R^{20}$, or —$S^+R^{21}R^{22}$; and at least one of $R^3$, $R^4$, $R^5$, $R^{15}$, $R^{16}$, $R^{17}$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$, —$P^+R^{18}R^{19}R^{20}$, or —$S^+R^{21}R^{22}$; and at least one of $R^3$, $R^4$, $R^5$, $R^{15}$, $R^{16}$, $R^{17}$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, —$N^+R^{15}R^{16}R^{17}$, —$P^+R^{18}R^{19}R^{20}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$, $R^{17}$, $R^{18}$, $R^{19}$, $R^{20}$, $R^{23}$ and $R^{24}$ may be as defined anywhere herein; at least one of $R^3$, $R^4$ and $R^5$ may be —$N^+R^{15}R^{16}R^{17}$, —$P^+R^{18}R^{19}R^{20}$, or —$NR^{23}R^{24}$; and at least one of $R^3$, $R^4$, $R^5$, $R^{15}$, $R^{16}$, $R^{17}$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$, —$P^+R^{18}R^{19}R^{20}$, or —$NR^{23}R^{24}$ and at least one of $R^3$, $R^4$, $R^5$, $R^{15}$, $R^{16}$, $R^{17}$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, —$N^+R^{15}R^{16}R^{17}$, —$S^+R^{21}R^{22}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$, $R^{17}$, $R^{21}$, $R^{22}$, $R^{23}$ and $R^{24}$ may be as defined anywhere herein; at least one of $R^3$, $R^4$ and $R^5$ may be —$N^+R^{15}R^{16}R^{17}$, —$S^-R^{21}R^{22}$ or —$NR^{23}R^{24}$; and at least one of $R^3$, $R^4$, $R^5$, $R^{15}$, $R^{16}$, $R^{17}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$, —$S^+R^{21}R^{22}$ or —$NR^{23}R^{24}$ and at least one of $R^3$, $R^4$, $R^5$, $R^{15}$, $R^{16}$, $R^{17}$, $R^{21}$, $R^{22}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, $-P^+R^{18}R^{19}R^{20}$, $-S^+R^{21}R^{22}$, $-NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each of $R^{18}$, $R^{19}$, $R^{20}$, $R^{21}$, $R^{22}$, $R^{23}$ and $R^{24}$ may be as defined anywhere herein; at least one of $R^3$, $R^4$ and $R^5$ may be $-P^+R^{18}R^{19}R^{20}$, $-S^+R^{21}R^{22}$ or $-NR^{23}R^{24}$; and at least one of $R^3$, $R^4$, $R^5$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, one of $R^3$, $R^4$ and $R^5$ may be $-P^+R^{18}R^{19}R^{20}$, $-S^+R^{21}R^{22}$ or $-NR^{23}R^{24}$ and at least one of $R^3$, $R^4$, $R^5$, $R^{18}$, $R^{19}$, $R^{20}$, $R^{21}$, $R^{22}$, $R^{23}$, and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, F, Cl, Br, I, $CX_3$, $-P^+R^{18}R^{19}R^{20}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{18}$, $R^{19}$, and $R^{20}$ may be as defined anywhere herein; at least one of $R^3$, $R^4$ and $R^5$ may be F, Cl, Br, I, $CX_3$, or $-P^+R^{18}R^{19}R^{20}$; and at least one of $R^3$, $R^4$, $R^5$, $R^{18}$, $R^{19}$, and $R^{20}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be $-P^+R^{18}R^{19}R^{20}$; and at least one of $R^3$, $R^4$, $R^5$, $R^{18}$, $R^{19}$, and $R^{20}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be $-P^+R^{18}$, $R^{19}R^{20}$; and at least one of $R^3$, $R^4$, $R^5$, $R^{18}$, $R^{19}$, and $R^{20}$ may be a biomolecule, a linking group optionally joined to a biomolecule, or a group that may be substituted with at least one substituent that may be a biomolecule.

In various embodiments, each of $R^3$, $R^4$, and $R^5$ may independently be H, D, F, Cl, Br, I, $CX_3$, $-S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{21}$ and $R^{22}$ may be as defined anywhere herein; at least one of $R^3$, $R^4$ and $R^5$ may be F, Cl, Br, I, $CX_3$, or $-S^+R^{21}R^{22}$; and at least one of $R^3$, $R^4$, $R^5$, $R^{21}$, and $R^{22}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be $-S^-R^{21}R^{22}$; and at least one of $R^3$, $R^4$, $R^5$, $R^{21}$, and $R^{22}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be $-S^+R^{21}R^{22}$; and at least one of $R^3$, $R^4$, $R^5$, $R^{21}$, and $R^{22}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, F, Cl, Br, I, $CX_3$, $-NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each X may be the same or different and may be F, Cl, Br, or I; each of $R^{23}$ and $R^{24}$ may be as defined anywhere herein; at least one of $R^3$, $R^4$ and $R^5$ may be F, Cl, Br, I, $CX_3$, or $-NR^{23}R^{24}$; and at least one of $R^3$, $R^4$, $R^5$, $R^{23}$, and $R^{24}$ may be a biomolecule, a linking group optionally joined to a biomolecule, or a group that may be substituted with at least one substituent that may be a biomolecule. In various embodiments, at least two of $R^3$, $R^4$ and $R^5$ may independently be F, Cl, Br, I, or $CX_3$, or at least one of $R^3$, $R^4$ and $R^5$ may be $-NR^{23}R^{24}$; and at least one of $R^3$, $R^4$, $R^5$, $R^{23}$, and $R^{24}$ may be a biomolecule, a linking group optionally joined to a biomolecule, or a group that may be substituted with at least one substituent that may be a biomolecule. In various embodiments, two of $R^3$, $R^4$ and $R^5$ may independently be F, Cl, Br, I, or $CX_3$, or one of $R^3$, $R^4$ and $R^5$ may be $-NR^{23}R^{24}$; and at least one of $R^3$, $R^4$, $R^5$, $R^{23}$, and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, $-N^+R^{15}R^{16}R^{17}$, $-P^+R^{18}R^{19}R^{20}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each of $R^{15}$, $R^{16}$, $R^{17}$, $R^{18}$, $R^{19}$, and $R^{20}$ may be as defined anywhere herein; at least one of $R^3$, $R^4$ and $R^5$ may be $-N^+R^{15}R^{16}R^{17}$ or $-P^+R^{18}R^{19}R^{20}$; and at least one of $R^3$, $R^4$, $R^5$, $R^{15}$, $R^{16}$, $R^{17}$, $R^{18}$, $R^{19}$, and $R^{20}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$ or —$P^+R^{18}R^{19}R^{20}$ and at least one of $R^3$, $R^4$, $R^5$, $R^{15}$, $R^{16}$, $R^{17}$, $R^{18}$, $R^{19}$, and $R^{20}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, —$N^+R^{15}R^{16}R^{17}$, —$S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$, $R^{17}$, $R^{21}$ and $R^{22}$ may be as defined anywhere herein; at least one of $R^3$, $R^4$ and $R^5$ may be —$N^+R^{15}R^{16}R^{17}$ or —$S^+R^{21}R^{22}$; and at least one of $R^3$, $R^4$, $R^5$, $R^{15}$, $R^{16}$, $R^{17}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$ or —$S^+R^{21}R^{22}$ and at least one of $R^3$, $R^4$, $R^5$, $R^{15}$, $R^{16}$, $R^{17}$, $R^{21}$, and $R^{22}$ may be a biomolecule, a linking group optionally joined to a biomolecule, or a group that may be substituted with at least one substituent that may be a biomolecule, or forms a group that is substituted with at least one substituent that is a biomolecule.

In various embodiments, each of $R^3$, $R^4$, and $R^5$ may independently be H, D, —$N^+R^{15}R^{16}R^{17}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$, $R^{17}$, $R^{23}$ and $R^{24}$ may be as defined anywhere herein; at least one of $R^3$, $R^4$ and $R^5$ may be —$N^+R^{15}R^{16}R^{17}$ or —$NR^{23}R^{24}$; and at least one of $R^3$, $R^4$, $R^5$, $R^{15}$, $R^{16}$, $R^{17}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule. In various embodiments, one of $R^3$, $R^4$ and $R^5$ may be —$N^+R^{15}R^{16}R^{17}$ or —$NR^{23}R^{24}$; and at least one of $R^3$, $R^4$, $R^5$, $R^{15}$, $R^{16}$, $R^{17}$, $R^{23}$, and $R^{24}$ may be a biomolecule, a linking group optionally joined to a biomolecule, or a group that may be substituted with at least one substituent that may be a biomolecule, or forms a group that is substituted with at least one substituent that is a biomolecule.

In an embodiment, each of $R^3$, $R^4$, and $R^5$ may independently be H, D, —$P^+R^{18}R^{19}R^{20}$, —$S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{18}$, $R^{19}$, $R^{20}$, $R^{21}$ and $R^{22}$ may be as defined anywhere herein; at least one of $R^3$, $R^4$ and $R^5$ may be —$P^+R^{18}R^{19}R^{20}$ or —$S^+R^{21}R^{22}$; and at least one of $R^3$, $R^4$, $R^5$, $R^{18}$, $R^{19}$, $R^{20}$, $R^{21}$, and $R^{22}$ may be a biomolecule, a linking group optionally joined to a biomolecule, or a group that may be substituted with at least one substituent that may be a biomolecule. In various embodiments, one of $R^3$, $R^4$ and $R^5$ may be —$P^+R^{18}R^{19}R^{20}$ or —$S^+R^{21}R^{22}$; and at least one of $R^3$, $R^4$, $R^5$, $R^{18}$, $R^{19}$, $R^{20}$, $R^{21}$ and $R^{22}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, —$P^+R^{18}R^{19}R^{20}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{18}$, $R^{19}$, $R^{20}$, $R^{23}$, and $R^{24}$ may be as defined anywhere herein; at least one of $R^3$, $R^4$ and $R^5$ may be —$P^+R^{18}R^{19}R^{20}$ or —$NR^{23}R^{24}$; and at least one of $R^3$, $R^4$, $R^5$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule. In various embodiments, one of $R^3$, $R^4$ and $R^5$ may be —$P^+R^{18}R^{19}R^{20}$ or —$NR^{23}R^{24}$; and at least one of $R^3$, $R^4$, $R^5$, $R^{18}$, $R^{19}$, $R^{20}$, $R^{23}$, and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, —$S^+R^{21}R^{22}$, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{21}$, $R^{22}$, $R^{23}$ and $R^{24}$ may be as defined anywhere herein; at least one of $R^3$, $R^4$ and $R^5$ may be —$S^+R^{21}R^{22}$ or —$NR^{23}R^{24}$; and at least one of $R^3$, $R^4$, $R^5$, $R^{21}$, $R^{22}$, $R^{23}$, and $R^{24}$ may be a biomolecule, a linking group optionally joined to a biomolecule, or a group that may be substituted with at least one substituent that may be a biomolecule. In various embodiments, one of $R^3$, $R^4$ and $R^5$ may be —$S^+R^{21}R^{22}$ or —$NR^{23}R^{24}$ and at least one of $R^3$, $R^4$, $R^5$, $R^{21}$, $R^{22}$, $R^{23}$ and $R^{24}$ may be a biomolecule, a linking group optionally joined to a biomolecule, or a group that may be substituted with at least one substituent that may be a biomolecule.

In an embodiment, each of $R^3$, $R^4$, and $R^5$ may independently be H, D, F, Cl, Br, I, $CX_3$, —$N^+R^{15}R^{16}R^{17}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; each of $R^{15}$, $R^{16}$ and $R^{17}$ may be as defined anywhere herein; at least one of $R^3$, $R^4$ and $R^5$ may be F, Cl, Br, I, $CX_3$, or —$N^+R^{15}R^{16}R^{17}$; and at least one of $R^3$, $R^4$, $R^5$, $R^{15}$, $R^{16}$ and $R^{17}$ may be a biomolecule, a linking group optionally joined to a biomolecule, or a group that may be substituted with at least one substituent that may be a biomolecule, or forms a group that is substituted with at least one substituent that is a biomolecule. In various embodiments, at least two of $R^3$, $R^4$ and $R^5$ may independently be F, Cl, Br, I, or $CX_3$, or at least one of $R^3$, $R^4$ and $R^5$ may be —$N^+R^{15}R^{16}R^{17}$; and at least one of $R^3$, $R^4$, $R^5$, $R^{15}$, $R^{16}$ and $R^{17}$ may be a biomolecule, a linking group optionally joined to a biomolecule, or a group that may be substituted with at least one substituent that may be a biomolecule, or forms a group that is substituted with at least one substituent that is a biomolecule. In various embodiments, two of $R^3$, $R^4$ and $R^5$ may independently be F, Cl, Br, I, or $CX_3$, or one of $R^3$, $R^4$ and $R^5$ may be —$N^+R^{15}R^{16}R^{17}$; and at least one of $R^3$, $R^4$, $R^5$, $R^{15}$, $R^{16}$ and $R^{17}$ may be a biomolecule, a linking group optionally joined to a biomolecule, or a group that may be substituted with at least one substituent that may be a biomolecule, or forms a group that is substituted with at least one substituent that is a biomolecule.

In various embodiments, the compound may be of the formula (IV):

wherein $Q^1$ may be —$CR^3R^4R^5$; and each of $R^3$, $R^4$, and $R^5$ may independently be H, D, F, Cl, Br, I, $CX_3$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; at least one of $R^3$, $R^4$ and $R^5$ may be F, Cl, Br, I, or $CX_3$; and at least one of $R^3$, $R^4$ and $R^5$ may be a biomolecule, a linking group optionally joined to a biomolecule, or a group that may be substituted with at least one substituent that may be a biomolecule. In various embodiments, each of $R^3$, $R^4$, and $R^5$ may independently be F, Cl, Br, I, $CX_3$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each X may be the same or different and may be F, Cl, Br, or I; two of $R^3$, $R^4$ and $R^5$ may be F, Cl, Br, I, or $CX_3$; and one of $R^3$, $R^4$ and $R^5$ may be a biomolecule, a linking group optionally joined to a biomolecule, or a group that may be substituted with at least one substituent that may be a biomolecule. In various embodiments, two of $R^3$, $R^4$, and $R^5$ may independently be F, Cl, Br, I, or $CX_3$, and one of $R^3$, $R^4$ and $R^5$ may be a biomolecule or a linking group optionally joined to a biomolecule. In various embodiments, two of $R^3$, $R^4$, and $R^5$ may independently be F, Cl, Br, I, or $CX_3$, and one of $R^3$, $R^4$ and $R^5$ may be a biomolecule. In various embodiments, two of $R^3$, $R^4$, and $R^5$ may independently be F, Cl, Br, $CX_3$, and one of $R^3$, $R^4$ and $R^5$ may be a biomolecule or a linking group optionally joined to a biomolecule. In various embodiments, two of $R^3$, $R^4$, and $R^5$ may independently be F, Cl, Br, $CX_3$, and one of $R^3$, $R^4$ and $R^5$ may be a biomolecule. In an embodiment, two of $R^3$, $R^4$, and $R^5$ may independently be F, Br, I, or $CX_3$, and one of $R^3$, $R^4$ and $R^5$ may be a biomolecule or a linking group optionally joined to a biomolecule. In an embodiment, two of $R^3$, $R^4$, and $R^5$ may independently be F, Br, I, or $CX_3$, and one of $R^3$, $R^4$ and $R^5$ may be a biomolecule. In various embodiments, two of $R^3$, $R^4$, and $R^5$ may independently be F, Br, I, or $CX_3$, and one of $R^3$, $R^4$ and $R^5$ may be a biomolecule or a linking group optionally joined to a biomolecule. In an embodiment, two of $R^3$, $R^4$, and $R^5$ may independently be F, Br, I, or $CX_3$, and one of $R^3$, $R^4$ and $R^5$ may be a biomolecule. In an embodiment, two of $R^3$, $R^4$, and $R^5$ may independently be Cl, Br, I, or $CX_3$, and one of $R^3$, $R^4$ and $R^5$ may be a biomolecule or a linking group optionally joined to a biomolecule. In various embodiments, two of $R^3$, $R^4$, and $R^5$ may independently be Cl, Br, I, or $CX_3$, and one of $R^3$, $R^4$ and $R^5$ may be a biomolecule. In an embodiment, two of $R^3$, $R^4$, and $R^5$ may independently be F, Cl, or I, and one of $R^3$, $R^4$ and $R^5$ may be a biomolecule or a linking group optionally joined to a biomolecule. In an embodiment, two of $R^3$, $R^4$, and $R^5$ may independently be F, Cl, or I, and one of $R^3$, $R^4$ and $R^5$ may be a biomolecule. In an embodiment, two of $R^3$, $R^4$, and $R^5$ may independently be F, Cl, or $CX_3$, and one of $R^3$, $R^4$ and $R^5$ may be a biomolecule or a linking group optionally joined to a biomolecule. In an embodiment, two of $R^3$, $R^4$, and $R^5$ may independently be F, Cl, or $CX_3$, and one of $R^3$, $R^4$ and $R^5$ may be a biomolecule. In various embodiments, two of $R^3$, $R^4$, and $R^5$ may independently be F, Br, or I, and one of $R^3$, $R^4$ and $R^5$ may be a biomolecule or a linking group optionally joined to a biomolecule. In an embodiment, two of $R^3$, $R^4$, and $R^5$ may independently be F, Br, or I, and one of $R^3$, $R^4$ and $R^5$ may be a biomolecule. In various embodiments, two of $R^3$, $R^4$, and $R^5$ may independently be F, Br, or $CX_3$, and one of $R^3$, $R^4$ and $R^5$ may be a biomolecule or a linking group optionally joined to a biomolecule. In an embodiment, two of $R^3$, $R^4$, and $R^5$ may independently be F, Br, or $CX_3$, and one of $R^3$, $R^4$ and $R^5$ may be a biomolecule. In various embodiments, two of $R^3$, $R^4$, and $R^5$ may independently be F, I, or $CX_3$, and one of $R^3$, $R^4$ and $R^5$ may be a biomolecule or a linking group optionally joined to a biomolecule. In an embodiment, two of $R^3$, $R^4$, and $R^5$ may independently be F, I, or $CX_3$, and one of $R^3$, $R^4$ and $R^5$ may be a biomolecule. In various embodiments, two of $R^3$, $R^4$, and $R^5$ may independently be Cl, Br, or I, and one of $R^3$, $R^4$ and $R^5$ may be a biomolecule or a linking group optionally joined to a biomolecule. In an embodiment, two of $R^3$, $R^4$, and $R^5$ may independently be Cl, Br, or I, and one of $R^3$, $R^4$ and $R^5$ may be a biomolecule. In an embodiment, two of $R^3$, $R^4$, and $R^5$ may independently be Cl, Br, or $CX_3$, and one of $R^3$, $R^4$ and $R^5$ may be a biomolecule or a linking group optionally joined to a biomolecule. In an embodiment, two of $R^3$, $R^4$, and $R^5$ may independently be Cl, Br, or $CX_3$, and one of $R^3$, $R^4$ and $R^5$ may be a biomolecule. In an embodiment, two of $R^3$, $R^4$, and $R^5$ may independently be Cl, I, or $CX_3$, and one of $R^3$, $R^4$ and $R^5$ may be a biomolecule or a linking group optionally joined to a biomolecule. In an embodiment, two of $R^3$, $R^4$, and $R^5$ may independently be Cl, I, or $CX_3$, and one of $R^3$, $R^4$ and $R^5$ may be a biomolecule. In an embodiment, two of $R^3$, $R^4$, and $R^5$ may independently be Br, I, or $CX_3$, and one of $R^3$, $R^4$ and $R^5$ may be a biomolecule or a linking group optionally joined to a biomolecule. In an embodiment, two of $R^3$, $R^4$, and $R^5$ may independently be Br, I, or $CX_3$, and one of $R^3$, $R^4$ and $R^5$ may be a biomolecule. In an embodiment, two of $R^3$, $R^4$, and $R^5$ may independently be F or Br, and one of $R^3$, $R^4$ and $R^5$ may be a biomolecule or a linking group optionally joined to a biomolecule. In an embodiment, two of $R^3$, $R^4$, and $R^5$ may independently be F or Br, and one of $R^3$, $R^4$ and $R^5$ may be a biomolecule. In an embodiment, two of $R^3$, $R^4$, and $R^5$ may independently be F or I, and one of $R^3$, $R^4$ and $R^5$ may be a biomolecule or a linking group optionally joined to a biomolecule. In an embodiment, two of $R^3$, $R^4$, and $R^5$ may independently be F or I, and one of $R^3$, $R^4$ and $R^5$ may be a biomolecule. In an embodiment, two of $R^3$, $R^4$, and $R^5$ may independently be F or $CX_3$, and one of $R^3$, $R^4$ and $R^5$ may be a biomolecule or a linking group optionally joined to a biomolecule. In an embodiment, two of $R^3$, $R^4$, and $R^5$ may independently be F or $CX_3$, and one of $R^3$, $R^4$ and $R^5$ may be a biomolecule. In an embodiment, two of $R^3$, $R^4$, and $R^5$ may independently be Cl or Br, and one of $R^3$, $R^4$ and $R^5$ may be a biomolecule or a linking group optionally joined to a biomolecule. In an embodiment, two of $R^3$, $R^4$, and $R^5$ may independently be Cl or Br, and one of $R^3$, $R^4$ and $R^5$ may be a biomolecule. In an embodiment, two of $R^3$, $R^4$, and $R^5$ may independently be Cl or I, and one of $R^3$, $R^4$ and $R^5$ may be a biomolecule or a linking group optionally joined to a biomolecule. In an embodiment, two of $R^3$, $R^4$, and $R^5$ may independently be Cl or I, and one of $R^3$, $R^4$ and $R^5$ may be a biomolecule. In an embodiment, two of $R^3$, $R^4$, and $R^5$ may independently be Cl or $CX_3$, and one of $R^3$, $R^4$ and $R^5$ may be a biomolecule or a linking group optionally joined to a biomolecule. In an embodiment, two of $R^3$, $R^4$, and $R^5$ may independently be Cl or $CX_3$, and one of $R^3$, $R^4$ and $R^5$ may be a biomolecule. In an embodiment, two of $R^3$, $R^4$, and $R^5$ may independently be Br or I, and one of $R^3$, $R^4$ and $R^5$ may be a biomolecule or a linking group optionally joined to a biomolecule. In an embodiment, two of $R^3$, $R^4$, and $R^5$ may independently be Br or I, and one of $R^3$, $R^4$ and $R^5$ may be a biomolecule. In an embodiment, two of $R^3$, $R^4$, and $R^5$ may independently be Br or $CX_3$, and one of $R^3$, $R^4$ and $R^5$ may be a biomolecule or a linking group optionally joined to a biomolecule. In an embodiment, two of $R^3$, $R^4$, and $R^5$ may independently be Br or $CX_3$, and one of $R^3$, $R^4$ and $R^5$ may be a biomolecule. In an embodiment, two of $R^3$, $R^4$, and $R^5$ may independently be I or $CX_3$, and one of $R^3$, $R^4$ and $R^5$ may be a biomolecule or a linking group optionally joined to a biomolecule. In an embodiment, two of $R^3$, $R^4$, and $R^5$ may independently be I or $CX_3$, and one of $R^3$, $R^4$ and $R^5$ may be a biomolecule. In an embodiment, two of $R^3$, $R^4$, and $R^5$ may be $CX_3$, and one of $R^3$, $R^4$ and $R^5$ may be a biomolecule or a linking group optionally joined to a biomolecule. In an embodiment, two of $R^3$, $R^4$, and $R^5$ may be $CX_3$, and one of $R^3$, $R^4$ and $R^5$ may be a biomolecule. In an embodiment, two of $R^3$, $R^4$, and $R^5$ may be Cl, and one of $R^3$, $R^4$ and $R^5$ may be a biomolecule or a linking group optionally joined to a biomolecule. In an embodiment, two of $R^3$, $R^4$, and $R^5$ may be Cl, and one of $R^3$, $R^4$ and $R^5$ may be a biomolecule. In an embodiment, two of $R^3$, $R^4$, and $R^5$ may be Br, and one of $R^3$, $R^4$ and $R^5$ may be a biomolecule or a linking group optionally joined to a biomolecule. In an embodiment, two of $R^3$, $R^4$, and $R^5$ may be Br, and one of $R^3$, $R^4$ and $R^5$ may be a biomolecule. In an embodiment, two of $R^3$, $R^4$, and $R^5$ may be I, and one of $R^3$, $R^4$ and $R^5$ may be a biomolecule or a linking group optionally joined to a biomolecule. In an embodiment, two of $R^3$, $R^4$, and $R^5$ may be I, and one of $R^3$, $R^4$ and $R^5$ may be a biomolecule. In various embodiments, two of $R^3$, $R^4$, and $R^5$ may independently be F, Cl, Br, or I, and one of $R^3$, $R^4$ and $R^5$ may be a biomolecule or a linking group optionally joined to a biomolecule. In various embodiments, two of $R^3$, $R^4$, and $R^5$ may independently be F, Cl, Br, or I, and one of $R^3$, $R^4$ and $R^5$ may be a biomolecule. In an embodiment, two of $R^3$, $R^4$, and $R^5$ may independently be F, Cl, or Br, and one of $R^3$, $R^4$ and $R^5$ may be a biomolecule or a linking group optionally joined to a biomolecule. In an embodiment, two of $R^3$, $R^4$, and $R^5$ may independently be F, Cl, or Br, and one of $R^3$, $R^4$ and $R^5$ may be a biomolecule. In an embodiment, two of $R^3$, $R^4$, and $R^5$ may independently be F or Cl, and one of $R^3$, $R^4$ and $R^5$ may be a biomolecule or a linking group optionally joined to a biomolecule. In an embodiment, two of $R^3$, $R^4$, and $R^5$ may independently be F or Cl, and one of $R^3$, $R^4$ and $R^5$ may be a biomolecule. In an embodiment, two of $R^3$, $R^4$, and $R^5$ may be F, and one of $R^3$, $R^4$ and $R^5$ may be a biomolecule or a linking group optionally joined to a biomolecule. In an embodiment, two of $R^3$, $R^4$, and $R^5$ may be F, and one of $R^3$, $R^4$ and $R^5$ may be a biomolecule. In an embodiment, each X may be the same or different and may be F, Cl, Br, or I. In various embodiments, each X may be the same or different and may be F, Cl, or I. In various embodiments, each X may be the same or different and may be F, Br, or I. In an embodiment, each X may be the same or different and may be Cl, Br, or I. In an embodiment, each X may be the same or different and may be F or Br. In an embodiment, each X may be the same or different and may be F or I. In an embodiment, each X may be the same or different and may be Cl or Br. In an embodiment, each X may be the same or different and may be Cl or I. In an embodiment, each X may be the same or different and may be Br or I. In an embodiment, each X may be Cl. In an embodiment, each X may be Br. In an embodiment, each X may be I. In various embodiments, each X may be the same or different and may be F, Cl, Br. In an embodiment, each X may be the same or different and may be F or Cl. In an embodiment, each X may be F.

In various embodiments, the compound may be of the formula (IV):

(IV)

wherein $Q^1$ may be $-CR^3R^4R^5$; and each of $R^3$, $R^4$, and $R^5$ may independently be H, D, $-N^+R^{15}R^{16}R^{17}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of $-CR^3R^4R^5$ through a carbon atom; each of $R^{15}$, $R^{16}$ and $R^{17}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P, each of the $C_1$-$C_{15}$ alkyl group and the $C_3$-$C_{18}$ cycloalkyl group may be joined to the nitrogen atom of —$N^+R^{15}R^{16}R^{17}$ through a carbon atom, or $R^{15}$ may be absent and $R^{16}$ and $R^{17}$ may be joined so that —$N^+R^{15}R^{16}R^{17}$ forms a positively charged nitrogen containing heterocyclic group which may be substituted or unsubstituted; at least one of $R^3$, $R^4$ and $R^5$ may be —$N^+R^{15}R^{16}R^{17}$; and at least one of $R^3$, $R^4$, $R^5$, $R^{15}$, $R^{16}$, and $R^{17}$ may be a biomolecule, a linking group optionally joined to a biomolecule, or a group that may be substituted with at least one substituent that may be a biomolecule, or forms a group that is substituted with at least one substituent that is a biomolecule. In various embodiments, $R^3$ may be —$N^+R^{15}R^{16}R^{17}$; each of each of $R^4$ and $R^5$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{15}$, $R^{16}$ and $R^{17}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P, each of the $C_1$-$C_{15}$ alkyl group and the $C_3$-$C_{18}$ cycloalkyl group may be joined to the nitrogen atom of —$N^+R^{15}R^{16}R^{17}$ through a carbon atom, or $R^{15}$ may be absent and $R^{16}$ and $R^{17}$ may be joined so that —$N^+R^{15}R^{16}R^{17}$ forms a positively charged nitrogen containing heterocyclic group which may be substituted or unsubstituted; and at least one of $R^4$, $R^5$, $R^{15}$, $R^{16}$ and $R^{17}$ may be a biomolecule, a linking group optionally joined to a biomolecule, or a group that may be substituted with at least one substituent that may be a biomolecule, or forms a group that is substituted with at least one substituent that is a biomolecule. In an embodiment, each of $R^{15}$, $R^{16}$ and $R^{17}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P, and each of the $C_1$-$C_{15}$ alkyl group and the $C_3$-$C_{18}$ cycloalkyl group may be joined to the nitrogen atom of —$N^+R^{15}R^{16}R^{17}$ through a carbon atom. In various embodiments, $R^{15}$ may be absent and $R^{16}$ and $R^{17}$ may be joined so that —$N^+R^{15}R^{16}R^{17}$ forms a positively charged nitrogen containing heterocyclic group which may be substituted or unsubstituted. In various embodiments, $R^{15}$ may be absent and $R^{16}$ and $R^{17}$ may be joined so that —$N^+R^{15}R^{16}R^{17}$ forms a positively charged 4 to 6-membered nitrogen containing heterocyclic group which may be substituted or unsubstituted. In an embodiment, the positively charged 4 to 6-membered nitrogen containing heterocyclic group may be a pyridinium group, an imidazolium group, a pyrazinium group, a pyrimidinium group or a pyridazinium group, each of which may be substituted or unsubstituted. In various embodiments, the positively charged nitrogen containing heterocyclic group may be unsubstituted. In various embodiments, the positively charged nitrogen containing heterocyclic group which may be substituted with one or more substituents that are selected from the group consisting of a $C_1$-$C_{15}$ alkyl group, a biomolecule, a linking group optionally joined to a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, the compound may be of the formula (IV):

(IV)

wherein $Q^1$ may be —$CR^3R^4R^5$; and each of $R^3$, $R^4$, and $R^5$ may independently be H, D, —$P^+R^{18}R^{19}R^{20}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{18}$, $R^{19}$, and $R^{20}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the phosphorus atom of —$P^+R^{18}R^{19}R^{20}$ through a carbon atom; at least one of $R^3$, $R^4$ and $R^5$ may be —$P^+R^{18}R^{19}R^{20}$; and at least one of $R^3$, $R^4$, $R^5$, $R^{18}$, $R^{19}$, and $R^{20}$ may be a biomolecule, a linking group optionally joined to a biomolecule, or a group that may be substituted with at least one substituent that may be a biomolecule. In various embodiments, $R^3$ may be —$P^+R^{18}R^{19}R^{20}$; each of $R^4$ and $R^5$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{18}$, $R^{19}$, and $R^{20}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the phosphorus atom of —$P^+R^{18}R^{19}R^{20}$ through a carbon atom; and at least one of $R^4$, $R^5$, $R^{18}$, $R^{19}$, and $R^{20}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, the compound may be of the formula (IV):

(IV)

wherein $Q^1$ may be $CR^3R^4R^5$; and each of $R^3$, $R^4$, and $R^5$ may independently be H, D, —$S^+R^{21}R^{22}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{21}$ and $R^{22}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the sulfur atom of —$S^+R^{21}R^{22}$ through a carbon atom; at least one of $R^3$, $R^4$ and $R^5$ may be —$S^+R^{21}R^{22}$; and at least one of $R^3$, $R^4$, $R^5$, $R^{21}$, and $R^{22}$ may be a biomolecule, a linking group optionally joined to a biomolecule, or a group that may be substituted with at least one substituent that may be a biomolecule. In various embodiments, $R^3$ may be —$S^+R^{21}R^{22}$; each of $R^4$ and $R^5$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{21}$ and $R^{22}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the sulfur atom of —$S^-R^{21}R^{22}$ through a carbon atom; and at least one of $R^4$, $R^5$, $R^{21}$, and $R^{22}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, the compound may be of the formula (IV):

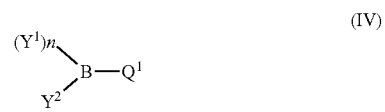

(IV)

wherein $Q^1$ may be —$CR^3R^4R^5$; and each of $R^3$, $R^4$, and $R^5$ may independently be H, D, —$NR^{23}R^{24}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{23}$ and $R^{24}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the nitrogen atom of —$NR^{23}R^{24}$ through a carbon atom; at least one of $R^3$, $R^4$ and $R^5$ may be —$NR^{23}R^{24}$; and at least one of $R^3$, $R^4$, $R^5$, $R^{23}$, and $R^{24}$ may be a biomolecule, a linking group optionally joined to a biomolecule, or a group that may be substituted with at least one substituent that may be a biomolecule. In various embodiments, $R^3$ may be —$NR^{23}R^{24}$; each of $R^4$ and $R^5$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —$CR^3R^4R^5$ through a carbon atom; each of $R^{23}$ and $R^{24}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the nitrogen atom of —$NR^{23}R^{24}$ through a carbon atom; and at least one of $R^4$, $R^5$, $R^{23}$, and $R^{24}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, the compound may be of the formula (IV):

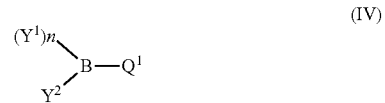

(IV)

wherein $Q^1$ may be —C≡CR$^8$; and R$^8$ may be as defined anywhere herein.

In an embodiment, R$^8$ may be —N$^+$R$^{25}$R$^{26}$R$^{27}$, —P$^+$R$^{28}$R$^{29}$R$^{30}$, —S$^+$R$^{31}$R$^{32}$, —NR$^{33}$R$^{34}$,

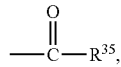

a biomolecule, a linking group optionally joined to a biomolecule, a linear or branched $C_1$-$C_{15}$ alkyl group or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of —C≡CR$^8$ through a carbon atom; each of R$^{25}$, R$^{26}$, R$^{27}$, R$^{28}$, R$^{29}$, R$^{30}$, R$^{31}$, R$^{32}$, R$^{33}$, R$^{34}$, and R$^{35}$ may be as defined anywhere herein; and at least one of R$^8$, R$^{25}$, R$^{26}$, R$^{27}$, R$^{28}$, R$^{29}$, R$^{30}$, R$^{31}$, R$^{32}$, R$^{33}$, R$^{34}$, and R$^{35}$ may be a biomolecule, a linking group optionally joined to a biomolecule, or a group that may be substituted with at least one substituent that may be a biomolecule, or forms a group that is substituted with at least one substituent that is a biomolecule.

In various embodiments, R$^8$ may be —N$^+$R$^{25}$R$^{26}$R$^{27}$; each of R$^{25}$, R$^{26}$ and R$^{27}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the nitrogen atom of —N$^+$R$^{25}$R$^{26}$R$^{27}$ through a carbon atom, or R$^{25}$ may be absent and R$^{26}$ and R$^{27}$ may be joined so that —N$^+$R$^{25}$R$^{26}$R$^{27}$ forms a positively charged nitrogen containing heterocyclic group which may be unsubstituted or substituted; and at least one of R$^{25}$, R$^{26}$ and R$^{27}$ may be a biomolecule, a linking group optionally joined to a biomolecule, or a group that may be substituted with at least one substituent that may be a biomolecule, or forms a group that is substituted with at least one substituent that is a biomolecule. In an embodiment, the positively charged 4 to 6-membered nitrogen containing heterocyclic group may be a pyridinium group, an imidazolium group, a pyrazinium group, a pyrimidinium group or a pyridazinium group, each of which may be substituted or unsubstituted. In various embodiments, the positively charged nitrogen containing heterocyclic group may be unsubstituted. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, R$^8$ may be —P$^+$R$^{28}$R$^{29}$R$^{30}$; each of R$^{28}$, R$^{29}$, and R$^{30}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the phosphorus atom of —P$^+$R$^{28}$R$^{29}$R$^{30}$ through a carbon atom; and at least one of R$^{28}$, R$^{29}$ and R$^{30}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, R$^8$ may be —S$^+$R$^{31}$R$^{32}$; each of R$^{31}$ and R$^{32}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the sulfur atom of —S$^+$R$^{31}$R$^{32}$ through a carbon atom; and at least one of R$^{31}$ and R$^{32}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In an embodiment, R$^8$ may be —NR$^{33}$R$^{34}$; each of R$^{33}$ and R$^{34}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the nitrogen atom of —NR$^{33}$R$^{34}$ through a carbon atom; and at least one of R$^{33}$ and R$^{34}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In an embodiment, R$^8$ may be

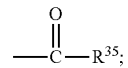

and R$^{35}$ may be a biomolecule, a linking group optionally joined to a biomolecule, a linear or branched $C_1$-$C_{15}$ alkyl group or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of

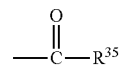

through a carbon atom. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, $R^8$ may be a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of —C≡$CR^8$ through a carbon atom. In various embodiments, $R^8$ may be a linear or branched $C_1$-$C_{15}$ alkyl group or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of —C≡$CR^8$ through a carbon atom. In various embodiments, $R^8$ may be a biomolecule or a linking group optionally joined to a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In an embodiment, the compound may be of the formula (IV):

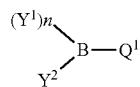

(IV)

wherein $Q^1$ may be

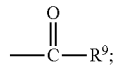

and $R^9$ may be as defined anywhere herein.

In various embodiments, $R^9$ may be —$NR^{38}R^{39}$,

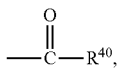

a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; each of the $C_1$-$C_{15}$ alkyl group and the $C_3$-$C_{18}$ cycloalkyl group may be joined to the carbon atom of

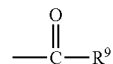

through a carbon atom; each of $R^{38}$, $R^{39}$, and $R^{40}$ may be as defined anywhere herein; and at least one of $R^9$, $R^{38}$, $R^{39}$, and $R^{40}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, $R^9$ may be —$NR^{38}R^{39}$; each of $R^{38}$ and $R^{39}$ may independently be H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be unsubstituted or substituted and may be optionally intercepted with at least one heteroatom selected from the group consisting of O, S, N and P; each of the $C_1$-$C_{15}$ alkyl group and the $C_3$-$C_{18}$ cycloalkyl group may be joined to the nitrogen atom of —$NR^{38}R^{39}$ through a carbon atom; and at least one of $R^{38}$ and $R^{39}$ may be a biomolecule, a linking group optionally joined to a biomolecule, or a group that may be substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In an embodiment, $R^9$ may be

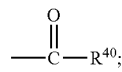

and $R^{40}$ may be a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of

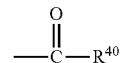

through a carbon atom. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, $R^9$ may be a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of

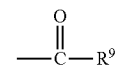

through a carbon atom. In an embodiment, $R^9$ may be a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group may be substituted with at least one substituent that may be a biomolecule and may be optionally intercepted with at least one heteroatom selected from the group consisting of O, S, N and P; and each of the $C_1$-$C_{15}$ alkyl group and the $C_3$-$C_{18}$ cycloalkyl group may be joined to the carbon atom of

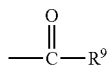

through a carbon atom. In an embodiment, $R^9$ may be a biomolecule or a linking group optionally joined to a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, the compound may be of the formula (IV):

wherein $Q^1$ may be —$R^{10}C$=$CR^{11}R^{12}$; and each of $R^{10}$, $R^{11}$, and $R^{12}$ may be as defined anywhere herein.

In various embodiments, each of $R^{10}$, $R^{11}$, and $R^{12}$ may independently be H, D, F, Cl, Br, I, $CX_3$, —$N^+R^{41}R^{42}R^{43}$, —$P^+R^{44}R^{45}R^{46}$, —$S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; each of $R^{41}$, $R^{42}$, $R^{43}$, $R^{44}$, $R^{45}$, $R^{46}$, $R^{47}$, and $R^{48}$ may be as defined anywhere herein; at least one of $R^{10}$, $R^{11}$, and $R^{12}$ may independently be F, Cl, Br, I, $CX_3$, —$N^+R^{41}R^{42}R^{43}$, —$P^+R^{44}R^{45}R^{46}$, or —$S^+R^{47}R^{48}$; and at least one of $R^{10}$, $R^{11}$, $R^{12}$, $R^{41}$, $R^{42}$, $R^{43}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be —$N^+R^{41}R^{42}R^{43}$, —$P^+R^{44}R^{45}R^{46}$, or —$S^+R^{47}R^{48}$; and at least one of $R^{10}$, $R^{11}$, $R^{12}$, $R^{41}$, $R^{42}$, $R^{43}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, —$N^+R^{41}R^{42}R^{43}$, —$P^+R^{44}R^{45}R^{46}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; each of $R^{41}$, $R^{42}$, $R^{43}$, $R^{44}$, $R^{45}$, $R^{46}$, $R^{47}$, and $R^{48}$ may be as defined anywhere herein; at least one of $R^{10}$, $R^{11}$, and $R^{12}$ may independently be F, Cl, Br, I, $CX_3$, —$N^+R^{41}R^{42}R^{43}$, or —$P^+R^{44}R^{45}R^{46}$; and at least one of $R^{10}$, $R^{11}$, $R^{12}$, $R^{41}$, $R^{42}$, $R^{43}$, $R^{44}$, $R^{45}$, and $R^{46}$ may be a biomolecule, a linking group optionally joined to a biomolecule, or a group that is substituted with at least one substituent that may be a biomolecule, or forms a group that is substituted with at least one substituent that is a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be —$N^+R^{41}R^{42}R^{43}$, or —$P^+R^{44}R^{45}R^{46}$; and at least one of $R^{10}$, $R^{11}$, $R^{12}$, $R^{41}$, $R^{42}$, $R^{43}$, $R^{44}$, $R^{45}$, and $R^{46}$ may be a biomolecule, a linking group optionally joined to a biomolecule, or a group that is substituted with at least one substituent that may be a biomolecule, or forms a group that is substituted with at least one substituent that is a biomolecule. In various embodiments, two of $R^{10}$, $R^{11}$, and $R^{12}$ may independently be F, Cl, Br, I, or $CX_3$, or one of $R^{10}$, $R^{11}$, and $R^{12}$ may be —$N^+R^{41}R^{42}R^{43}$, or —$P^+R^{44}R^{45}R^{46}$; and at least one of $R^{10}$, $R^{11}$, $R^{12}$, $R^{41}$, $R^{42}$, $R^{43}$, $R^{44}$, $R^{45}$, and $R^{46}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, —$N^-R^{41}R^{42}R^{43}$, —$S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; each of $R^{41}$, $R^{42}$, $R^{43}$, $R^{47}$, and $R^{48}$ may be as defined anywhere herein; at least one of $R^{10}$, $R^{11}$, and $R^{12}$ may independently be F, Cl, Br, I, $CX_3$, —$N^+R^{41}R^{42}R^{43}$, or —$S^+R^{47}R^{48}$; and at least one of $R^{10}$, $R^{11}$, $R^{12}$, $R^{41}$, $R^{42}$, $R^{43}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be —$N^+R^{41}R^{42}R^{43}$ or —$S^+R^{47}R^{48}$; and at least one of $R^{10}$, $R^{11}$, $R^{12}$, $R^{41}$, $R^{42}$, $R^{43}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, two of $R^{10}$, $R^{11}$, and $R^{12}$ may independently be F, Cl, Br, I, or $CX_3$, or one of $R^{10}$, $R^{11}$, and $R^{12}$ may be —$N^+R^{41}R^{42}R^{43}$ or —$S^+R^{47}R^{48}$, and at least one of $R^{10}$, $R^{11}$, $R^{12}$, $R^{41}$, $R^{42}$, $R^{43}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, —$P^+R^{44}R^{45}R^{46}$, —$S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; each of $R^{44}$, $R^{45}$, $R^{46}$, $R^{47}$, and $R^{48}$ may be as defined anywhere herein; at least one of $R^{10}$, $R^{11}$, and $R^{12}$ may independently be F, Cl, Br, I, $CX_3$, —$P^+R^{44}R^{45}R^{46}$, or —$S^+R^{47}R^{48}$; and at least one of $R^{10}$, $R^{11}$, $R^{12}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be —$P^+R^{44}R^{45}R^{46}$ or —$S^+R^{47}R^{48}$; and at least one of $R^{10}$, $R^{11}$, $R^{12}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, two of $R^{10}$, $R^{11}$, and $R^{12}$ may independently be F, Cl, Br, I, or $CX_3$, or one of $R^{10}$, $R^{11}$ and $R^{12}$ may be —$P^+R^{44}R^{45}R^{46}$ or —$S^+R^{47}R^{48}$; and at least one of $R^{10}$, $R^{11}$, $R^{12}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{15}$ cycloalkyl group may be a $C_4$-$C_8$ cycloalkyl group.

In various embodiments, each of $R^{10}$, $R^{11}$, and $R^{12}$ may independently be H, D, —$N^+R^{41}R^{42}R^{43}$, —$P^+R^{44}R^{45}R^{46}$, —$S^+R^{47}R^{48}$; a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom; each of $R^{41}$, $R^{42}$, $R^{43}$, $R^{44}$, $R^{45}$, $R^{46}$, $R^{47}$, and $R^{48}$ may be as defined anywhere herein; at least one of $R^{10}$, $R^{11}$, and $R^{12}$ may independently be —$N^+R^{41}R^{42}R^{43}$, —$P^+R^{44}R^{45}R^{46}$, or —$S^+R^{47}R^{48}$; and at least one of $R^{10}$, $R^{11}$, $R^{12}$, $R^{41}$, $R^{42}$, $R^{43}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, one of $R^{10}$, $R^{11}$, and $R^{12}$ may be —$N^+R^{41}R^{42}R^{43}$, —$P^+R^{44}R^{45}R^{46}$, or —$S^+R^{47}R^{48}$; and at least one of $R^{10}$, $R^{11}$, $R^{12}$, $R^{41}$, $R^{42}$, $R^{43}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, —$N^-R^{41}R^{42}R^{43}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; each of $R^{41}$, $R^{42}$, and $R^{43}$ may be as defined anywhere herein; at least one of $R^{10}$, $R^{11}$, and $R^{12}$ may independently be F, Cl, Br, I, $CX_3$, or —$N^+R^{41}R^{42}R^{43}$; and at least one of $R^{10}$, $R^{11}$, $R^{12}$, $R^{41}$, $R^{42}$, and $R^{43}$ may be a biomolecule, a linking group optionally joined to a biomolecule, or a group that is substituted with at least one substituent that may be a biomolecule, or forms a group that is substituted with at least one substituent that is a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be —$N^+R^{41}R^{42}R^{43}$; and at least one of $R^{10}$, $R^{11}$, $R^{12}$, $R^{41}$, $R^{42}$, and $R^{43}$ may be a biomolecule, a linking group optionally joined to a biomolecule, or a group that is substituted with at least one substituent that may be a biomolecule, or forms a group that is substituted with at least one substituent that is a biomolecule. In various embodiments, two of $R^{10}$, $R^{11}$, and $R^{12}$ may independently be F, Cl, Br, I, or $CX_3$, or one of $R^{10}$, $R^{11}$, and $R^{12}$ may be —$N^-R^{41}R^{42}R^{43}$; and at least one of $R^{10}$, $R^{11}$, $R^{12}$, $R^{41}$, $R^{42}$, and $R^{43}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_1$-$C_8$ cycloalkyl group.

In various embodiments, each of $R^{10}$, $R^{11}$, and $R^{12}$ may independently be H, D, F, Cl, Br, I, $CX_3$, —$P^+R^{44}R^{45}R^{46}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{15}$ cycloalkyl group is joined to the carbon atom of —$R^{10}C$=$CR^{11}R^{12}$ through a carbon atom, and each X is the same or different and is F, Cl, Br, or I; each of $R^{44}$, $R^{45}$, and $R^{46}$ may be as defined anywhere herein; at least one of $R^{10}$, $R^{11}$, and $R^{12}$ may independently be F, Cl, Br, I, $CX_3$, or $-P^+R^{44}R^{45}R^{46}$; and at least one of $R^{10}$, $R^{11}$, $R^{12}$, $R^{44}$, $R^{45}$, and $R^{46}$ may be a biomolecule, a linking group optionally joined to a biomolecule, or a group that is substituted with at least one substituent that may be a biomolecule. In various embodiments, at least two of $R^{10}$, $R^{11}$, and $R^{12}$ may independently be F, Cl, Br, I, or $CX_3$, or at least one of $R^{10}$, $R^{11}$, and $R^{12}$ may be $-P^+R^{44}R^{45}R^{46}$; and at least one of $R^{10}$, $R^{11}$, $R^{12}$, $R^{44}$, $R^{45}$, and $R^{46}$ may be a biomolecule, a linking group optionally joined to a biomolecule, or a group that is substituted with at least one substituent that may be a biomolecule. In various embodiments, two of $R^{10}$, $R^{11}$, and $R^{12}$ may independently be F, Cl, Br, I, or $CX_3$, or one of $R^{10}$, $R^{11}$, and $R^{12}$ may be $-P^+R^{44}R^{45}R^{46}$; and at least one of $R^{10}$, $R^{11}$, $R^{12}$, $R^{44}$, $R^{45}$, and $R^{46}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, $-S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of $-R^{10}C=CR^{11}R^{12}$ through a carbon atom, and each X is the same or different and is F, Cl, Br, or I; each of $R^{47}$ and $R^{48}$ may be as defined anywhere herein; at least one of $R^{10}$, $R^{11}$, and $R^{12}$ may independently be F, Cl, Br, I, $CX_3$, or $-S^+R^{47}R^{48}$; and at least one of $R^{10}$, $R^{11}$, $R^{12}$, $R^{47}$, and $R^{48}$ may be a biomolecule, a linking group optionally joined to a biomolecule, or a group that is substituted with at least one substituent that may be a biomolecule. In various embodiments, at least two of $R^{10}$, $R^{11}$ and $R^{12}$ may independently be F, Cl, Br, I, or $CX_3$, or at least one of $R^{10}$, $R^{11}$, and $R^{12}$ may be $-S^+R^{47}R^{48}$; and at least one of $R^{10}$, $R^{11}$, $R^{12}$, $R^{47}$, and $R^{48}$ may be a biomolecule, a linking group optionally joined to a biomolecule, or a group that is substituted with at least one substituent that may be a biomolecule. In various embodiments, at two of $R^{10}$, $R^{11}$, and $R^{12}$ may independently be F, Cl, Br, I, or $CX_3$, or one of $R^{10}$, $R^{11}$, and $R^{12}$ may be $-S^+R^{47}R^{48}$; and at least one of $R^{10}$, $R^{11}$, $R^{12}$, $R^{47}$, and $R^{48}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, $-N^+R^{41}R^{42}R^{43}$, $-P^+R^{44}R^{45}R^{46}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of $-R^{10}C=CR^{11}R^{12}$ through a carbon atom; each of $R^{41}$, $R^{42}$, $R^{43}$, $R^{44}$, $R^{45}$, and $R^{46}$ may be as defined anywhere herein; at least one of $R^{10}$, $R^{11}$, and $R^{12}$ may independently be $-N^+R^{41}R^{42}R^{43}$ or $-P^+R^{44}R^{45}R^{46}$; and at least one of $R^{10}$, $R^{11}$, $R^{12}$, $R^{41}$, $R^{42}$, $R^{43}$, $R^{44}$, $R^{45}$, and $R^{46}$ may be a biomolecule, a linking group optionally joined to a biomolecule, or a group that is substituted with at least one substituent that may be a biomolecule, or forms a group that is substituted with at least one substituent that is a biomolecule. In various embodiments, one of $R^{10}$, $R^{11}$, and $R^{12}$ may be $-N^+R^{41}R^{42}R^{43}$ or $-P^+R^{44}R^{45}R^{46}$; and at least one of $R^{10}$, $R^{11}$, $R^{12}$, $R^{41}$, $R^{42}$, $R^{43}$, $R^{44}$, $R^{45}$, and $R^{46}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, $-N^+R^{41}R^{42}R^{43}$, $-S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of $-R^{10}C=CR^{11}R^{12}$ through a carbon atom; each of $R^{41}$, $R^{42}$, $R^{43}$, $R^{47}$, and $R^{48}$ may be as defined anywhere herein; at least one of $R^{10}$, $R^{11}$, and $R^{12}$ may independently be $-N^+R^{41}R^{42}R^{43}$ or $-S^+R^{47}R^{48}$; and at least one of $R^{10}$, $R^{11}$, $R^{12}$, $R^{41}$, $R^{42}$, $R^{43}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, one of $R^{10}$, $R^{11}$, and $R^{12}$ may be $-N^+R^{41}R^{42}R^{43}$ or $-S^+R^{47}R^{48}$; and at least one of $R^{10}$, $R^{11}$, $R^{12}$, $R^{41}$, $R^{42}$, $R^{43}$, $R^{47}$, and $R^{48}$ may be a biomolecule, a linking group optionally joined to a biomolecule, or a group that is substituted with at least one substituent that may be a biomolecule, or forms a group that is substituted with at least one substituent that is a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, $-P^+R^{44}R^{45}R^{46}$, $-S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of $-R^{10}C=CR^{11}R^{12}$ through a carbon atom; each of $R^{44}$, $R^{45}$, $R^{46}$, $R^{47}$, and $R^{48}$ may be as defined anywhere herein; at least one of $R^{10}$, $R^{11}$, and $R^{12}$ may independently be $-P^+R^{44}R^{45}R^{46}$ or $-S^+R^{47}R^{48}$; and at least one of $R^{10}$, $R^{11}$, $R^{12}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule. In various embodiments, one of $R^{10}$, $R^{11}$, and $R^{12}$ may be $-P^+R^{44}R^{45}R^{46}$ or $-S^+R^{47}R^{48}$; and at least one of $R^{10}$, $R^{11}$, $R^{12}$, $R^{44}$, $R^{45}$, $R^{46}$, $R^{47}$, and $R^{48}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, F, Cl, Br, I, $CX_3$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I; at least one of $R^{10}$, $R^{11}$, and $R^{12}$ may independently be F, Cl, Br, I, or $CX_3$; and at least one of $R^{10}$, $R^{11}$, and $R^{12}$ may be a biomolecule, a linking group optionally joined to a biomolecule, or a group that is substituted with at least one substituent that may be a biomolecule. In various embodiments, two of $R^{10}$, $R^{11}$, and $R^{12}$ may independently be F, Cl, Br, I, or $CX_3$; and one of $R^{10}$, $R^{11}$, and $R^{12}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, —$N^+R^{41}R^{42}R^{43}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom; each of $R^{41}$, $R^{42}$, and $R^{43}$ may be as defined anywhere herein; at least one of $R^{10}$, $R^{11}$, and $R^{12}$ may independently be —$N^+R^{41}R^{42}R^{43}$; and at least one of $R^{10}$, $R^{11}$, $R^{12}$, $R^{41}$, $R^{42}$, and $R^{43}$ may be a biomolecule, a linking group optionally joined to a biomolecule, or a group that is substituted with at least one substituent that may be a biomolecule, or forms a group that is substituted with at least one substituent that is a biomolecule. In various embodiments, one of $R^{10}$, $R^{11}$, and $R^{12}$ may be —$N^+R^{41}R^{42}R^{43}$; and at least one of $R^{10}$, $R^{11}$, $R^{12}$, $R^{41}$, $R^{42}$, and $R^{43}$ may be a biomolecule, a linking group optionally joined to a biomolecule, or a group that is substituted with at least one substituent that may be a biomolecule, or forms a group that is substituted with at least one substituent that is a biomolecule. In an embodiment, the positively charged 4 to 6-membered nitrogen containing heterocyclic group may be a pyridinium group, an imidazolium group, a pyrazinium group, a pyrimidinium group or a pyridazinium group, each of which may be substituted or unsubstituted. In various embodiments, the positively charged nitrogen containing heterocyclic group may be unsubstituted. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, —$P^+R^{44}R^{45}R^{46}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom; each of $R^{44}$, $R^{45}$, and $R^{46}$ may be as defined anywhere herein; at least one of $R^{10}$, $R^{11}$, and $R^{12}$ may independently be —$P^+R^{44}R^{45}R^{46}$; and at least one of $R^{10}$, $R^{11}$, $R^{12}$, $R^{44}$, $R^{45}$, and $R^{46}$ may be a biomolecule, a linking group optionally joined to a biomolecule, or a group that is substituted with at least one substituent that may be a biomolecule. In various embodiments, one of $R^{10}$, $R^{11}$, and $R^{12}$ may be —$P^+R^{44}R^{45}R^{46}$; and at least one of $R^{10}$, $R^{11}$, $R^{12}$, $R^{44}$, $R^{45}$, and $R^{46}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

In various embodiments, each of $R^{10}$, $R^{11}$, and $R^{12}$ may independently be H, D, —$S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and is optionally intercepted with at least one heteroatom selected from the group consisting of O, S, N and P; each of the $C_1$-$C_{15}$ alkyl group and the $C_3$-$C_{18}$ cycloalkyl group is joined to the carbon atom of —$R^{10}C$=$CR^{11}R^{12}$ through a carbon atom; each of $R^{47}$ and $R^{48}$ may be as defined anywhere herein; at least one of $R^{10}$, $R^{11}$, and $R^{12}$ may independently be —$S^+R^{47}R^{48}$; and at least one of $R^{10}$, $R^{11}$, $R^{12}$, $R^{47}$, and $R^{48}$ may be a biomolecule, a linking group optionally joined to a biomolecule, or a group that is substituted with at least one substituent that may be a biomolecule. In various embodiments, one of $R^{10}$, $R^{11}$, and $R^{12}$ may be —$S^+R^{47}R^{48}$; and at least one of $R^{10}$, $R^{11}$, $R^{12}$, $R^{47}$, and $R^{48}$ may be a biomolecule, a linking group optionally joined to a biomolecule, or a group that is substituted with at least one substituent that may be a biomolecule. In various embodiments, the $C_1$-$C_{15}$ alkyl group may be a $C_1$-$C_6$ alkyl group. In various embodiments, the $C_3$-$C_{18}$ cycloalkyl group may be a $C_4$-$C_8$ cycloalkyl group.

The term 'biomolecule' as used herein refers to a biomolecule, or analog or derivative of a biomolecule, or other molecule that may be delivered into a human or animal in order to track or image distribution of the biomolecule within a human or animal body or tissue via positron emission tomography. Examples are disclosed in WO 2005/077967. In some embodiments, a 'biomolecule' refers to any molecule of medical, physiological or scientific significance, analog or derivative thereof that may be compatible with a biological system or which possesses biological activity. Biomolecules may be delivered into a human or animal and include biomolecules that become localized at particular places in the organism. Examples include sugars, amino acids, nucleic acids, nucleotides, nucleosides, peptide hormones (steroid and nonsteroid), antibodies, aptamers and oligonucleotides, proteins, peptides, oligonucleotides, lipids, hormones, drugs (synthetic drugs and natural products), polysaccharides, liposomes, micelles, microsomes, magnetic particles, metal chelators, oligoribonucleotides, oligonucleotides and related analogs bearing modifications in the backbone, nucleobase, or phosphate linker regions that enhance stability or modulate specificity, peptidomimetics, dendrimers, drug delivery agents, nanotubes, fullerenes, virus particles, and other targeting molecules (e.g. cancer targeting molecules). Specific examples include, but are not limited to, biotin, matrix mettaloprotease inhibitors such as marimastat, insulin, somatostatin, somatotropin, somatomedin, adrenocorticotropic hormone, parathormone, follicle stimulating hormone, luteinizing hormone, epidermal growth factor, thyroid stimulating hormone, thyroid stimulating hormone releasing hormone, luteinizing hormone releasing hormone, vasopressin, bombesin, endothelin, gonadotropins, gonadotropin releasing hormone, antiflamin I&II, NLE-antiflamin II, brain natriureitic peptide, calcitonin, corticotropin releasing peptide, oxytocin, calpain inhibitor peptide, alpha-CGRP, corticotropin releasing factor, galanin, growth hormone releasing factor, guanylin, alpha-helical corticotropin releasing factor, laminin, alpha-melanocyte stimulating hormone, platelet derived growth factor, neuromedin, neurotensin, pancreatic polypeptide, pentagastrin, peptide-YY, pituitary adenylate cyclase activating peptide, secretin, thyrotropin releasing hormone, urocortin, vasoactive intestinal peptide, vasopressin, vascular endothelial growth factor, apamin, bungarotoxin, calciceptin, charybdotoxin, cobrotoxin, conotoxin, dendrotoxin, melittin, neuropeptide-Y, imperatoxin, taycatoxin, annexin, inhibin, insulin-like growth factor, prolactin, melanin stimulating hormone, melanin concentrating hormone, substance-P, tachykinin, angiotensin, antibodies of general structural classes of IgG, IgM, IgE, IgA, as well as single-chain, monoclonal, and recombinant forms used for current and anticipated imaging, diagnostic, and therapeutic applications. Specific targets that can be recognized by antibodies comprise without limitation: melanoma cell, melanoma specific antigen, myelin basic protein, breast cancer specific tumor markers such as Her2-Neu and Brc-Abl, alpha-fetoprotein, human chorionic gonadotropin, prostate specific antigen, prostate specific membrane antigen, epidermal growth factor receptors, fibroblast growth factor receptor, insulin receptor. Other examples are antibodies approved for use in therapy such as Herceptin™ (Amgen), Erbitux™ (Imclone). Polymers containing nucleobases and nucleotides including RNA, DNA, and PNAs and various synthetic derivatives thereof that reflect modification of the sugar, internucleoside linkage (backbone) and nucleobase portions are also contemplated. Oligonucleotides that can be used for imaging, for example: antisense oligonucleotides that target mRNA of genes implicated in the disease state, siRNA or RNAi molecules that target mRNA via RNA silencing, and aptamer structures which represent a diverse class of folded nucleic acid structures that target protein or glycoforms of proteins or both, or folded RNA structures. Further examples are aptamers approved for clinical use or those intended for clinical and diagnostic use such as Macugen™ (Eyetech) and aptamers that are used in the context of surface arrayed aptamers for diagnostic purposes, oligosaccharides of both synthetic and natural origin that are found on the surface of cellular receptors or can mimic the glycoforms of cellular receptors and proteins. Other saccharide components in synthetic glycoforms are sialic acid, mannose, fucose, N-acetyl-glucosamine, N-acetyl-mannosamine, maltose, galactose and N-acetyl-galactosamine, small to mid-size molecular weight ligands for proteins comprise various classes of compounds, for example: porphyrins, lectins, lipids, steroids, barbiturates, taxanes, terpenes, terpenoids, canabinoids, opioids, nucleosides, purines, pyrimidines, heteroaromatics, quinolines, biogenic amines, amino acids, indole-alkaloids, topane alkaloids, statins, enzyme inhibitors, nonsteroidal anti-inflammatory agents, monosaccharides, folates, derivatives of folate, methotrexate, derivatives of methotrexate, trexates, vitamins, growth hormone, VEGF, EGF, an antibody, a breast cancer antigen specific antibody, a prostate cancer antigen specific antibody, a melanoma antigen specific antibody, a ligand, a RGD-motif ligand recognizing a matrix metalloprotease, an aptamer, an aptamer recognizing a cell surface protein, folic acid, a folic acid derivative and a methotrexate. Tracer molecules used in this invention may be conjugated to a ligand such as a biomolecule that preferentially interacts with a tissue type or cell type of interest. In some embodiments, a precursor substituted alkyl-boronic acid may be pre-conjugated to a biomolecule of interest and subsequently fluoridated when needed in a one-step aqueous fluoridation reaction. A typical reaction may occur in a buffered solution of $KHF_2$ where the $^{18}F$ may be generated in carrier free form and supplemented with carrier $^{19}F$ either at the time of fluoridation or during a chase reaction, while in another typical reaction the $^{18}F$ will be used in an isotope exchange reaction. In various embodiments, the biomolecule may be a sugar, a peptide, a nucleic acid, a lipid, a steroid, a biogenic amine or derivative or analog thereof. In various embodiments, the biomolecule may be a hormone, a drug, insulin, somatostatin, growth hormone, VEGF, EGF, bombesin, a gonadotropin, gonadotropin releasing hormone, corticotropin releasing peptide, oxytocin, corticotropin releasing factor, growth hormone releasing factor, platelet derived growth factor, neurotensin, urocortin, vasoactive intestinal peptide, inhibin, insulin-like growth factor, an antisense oligonucleotide that targets mRNA of a gene implicated in the disease state, a siRNA or RNAi molecule that targets mRNA via RNA silencing, an antibody, a breast cancer antigen specific antibody, a prostate cancer antigen specific antibody, a melanoma antigen specific antibody, a ligand, a RGD-motif ligand recognizing a matrix metalloprotease, an aptamer, an aptamer recognizing a cell surface protein, folic acid, a folic acid derivative and a methotrexate or a derivative or analog thereof.

Linking groups may include aliphatic or aromatic moieties designed to insulate the biomolecule from the boron atom by an appropriate distance or to ensure that appropriate atoms are adjacent the boron atom to facilitate the fluoridation process. Groups which facilitate subsequent addition of a biomolecule are well known in the art and may include moieties which readily form a bond to a selected biomolecule, a variety of such groups being known in the art. These include thiol and amine reactive groups and other such groups which may be useful for joining a compound of this invention to functionalities on biomolecules including hydroxide, carboxylic acid, amine, sulfhydryl groups, etc. Further contemplated herein may be the joining of a compound of this invention to a biomolecule through other linkages involving what is known as "click chemistry" with examples that include reactions of tetrazines with either strained alkenes or alkynes, or alkynes with azides either by metal-mediated catalysis or strain promotion. Alternatively, bonds other than covalent bonds are contemplated. Thus, groups, which provide for ionic, hydrophobic and other non-covalent linkages to a biomolecule are contemplated. Exemplary linker groups for facilitating conjugation to a biomolecule include:

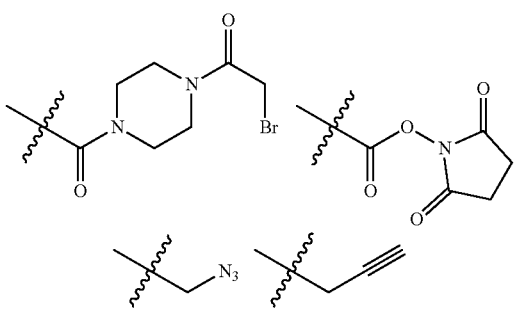

In various embodiments, n may be 1 or 2; and each $Y^1$ may independently be selected from the group consisting of $R^1$, $^{18}F$, and $^{19}F$. In various embodiments, n may be 1 or 2. Each $Y^1$ may independently be selected from the group consisting of $R^1$, $^{18}F$, and $^{19}F$. In various embodiments, n may be 2 and each $Y^1$ may independently be selected from the group consisting of $R^1$, $^{18}$ and $^{19}F$. In various embodiments, n may be 2, and each $Y^1$ may independently be $R^1$ or $^{18}F$, each $Y^1$ may independently be $R^1$ or $^{19}F$, or each $Y^1$ may independently be $^{18}F$ or $^{19}F$. In various embodiments, n may be 2, and each $Y^1$ may be $R^1$, each $Y^1$ may be $^{18}F$, or each $Y^1$ may be $^{19}F$. In various embodiments, n may be 1, and $Y^1$ may be $R^1$, $^{18}F$, or $^{19}F$.

In various embodiments, $R^1$ may be absent or present. In an embodiment, when $R^1$ is present, $R^1$ may be any non-interfering group with regard to fluoridation of B. In an embodiment, $R^1$ may be a linear or branched $C_1$-$C_{15}$ alkyl group or a non-aromatic $C_3$-$C_{18}$ cycloalkyl group, wherein each of the $C_1$-$C_{15}$ alkyl group and the non-aromatic $C_3$-$C_{18}$ cycloalkyl group is unsubstituted or substituted and is optionally intercepted with at least one heteroatom selected from the group consisting of O, S, N and P. In an embodiment, the $C_1$-$C_{15}$ alkyl group or non-aromatic $C_3$-$C_{18}$ cycloalkyl group may be intercepted with at least one heteroatom at or near the attachment point to B. In particular embodiments, $R^1$ may be a linear or branched $C_1$-$C_6$ alkyl group or a non-aromatic $C_3$-$C_8$ cycloalkyl group. In various embodiments, the $C_1$-$C_{15}$ alkyl group may be a $C_1$-$C_6$ alkyl group. In various embodiments, the non-aromatic $C_3$-$C_{18}$ cycloalkyl group may be a $C_4$-$C_8$ cycloalkyl group.

In various embodiments, $Y^2$ may independently be selected from the group consisting of $R^2$, $^{18}F$, and $^{19}F$. In an embodiment, $Y^2$ may independently be selected from the group consisting of $R^2$ and $^{18}F$. In an embodiment, $Y^2$ may independently be selected from the group consisting of $R^2$ and $^{19}F$. In an embodiment, $Y^2$ may independently be selected from the group consisting of $^{18}F$ and $^{19}F$. In various embodiments, $Y^2$ may be $R^2$. In various embodiments, $Y^2$ may be $^{18}F$. In various embodiments, $Y^2$ may be $^{19}F$.

In various embodiments, $R^2$ may be absent or present. In an embodiment, when $R^2$ is present, $R^2$ may be any non-interfering group with regard to fluoridation of B. In an embodiment, $R^2$ may be a linear or branched $C_1$-$C_{15}$ alkyl group or a non-aromatic $C_3$-$C_{18}$ cycloalkyl group, wherein each of the $C_1$-$C_{15}$ alkyl group and the non-aromatic $C_3$-$C_{18}$ cycloalkyl group is unsubstituted or substituted and is optionally intercepted with at least one heteroatom selected from the group consisting of O, S, N and P. In an embodiment, the $C_1$-$C_{15}$ alkyl group or non-aromatic $C_3$-$C_{18}$ cycloalkyl group may be intercepted with at least one heteroatom at or near the attachment point to B. In particular embodiments, $R^2$ may be a linear or branched $C_1$-$C_6$ alkyl group or a non-aromatic $C_3$-$C_8$ cycloalkyl group. In various embodiments, the $C_1$-$C_{15}$ alkyl group may be a $C_1$-$C_6$ alkyl group. In various embodiments, the non-aromatic $C_3$-$C_{18}$ cycloalkyl group may be a $C_4$-$C_8$ cycloalkyl group.

In various embodiments, each of $R^1$ and $R^2$ may independently be a linear or branched $C_1$-$C_{15}$ alkyl group or a non-aromatic $C_3$-$C_{18}$ cycloalkyl group, wherein each of the $C_1$-$C_{15}$ alkyl group and the non-aromatic $C_3$-$C_{18}$ cycloalkyl group is unsubstituted or substituted and is optionally intercepted with at least one heteroatom selected from the group consisting of O, S, N and P. In various embodiments, the $C_1$-$C_{15}$ alkyl group may be a $C_1$-$C_6$ alkyl group. In various embodiments, the non-aromatic $C_3$-$C_{18}$ cycloalkyl group may be a $C_4$-$C_8$ cycloalkyl group.

In various embodiments, n may be 2; each $Y^1$ may independently be $^{18}F$ or $^{19}F$; $Y^2$ may be $^{18}F$ or $^{19}F$; and at least one of $(Y^1)_n$ and $Y^2$ may be $^{18}F$.

In various embodiments, the a linear or branched $C_1$-$C_{15}$ alkyl group may be a linear or branched saturated $C_1$-$C_2$ alkyl group, or a linear or branched saturated $C_1$-$C_3$ alkyl group, or a linear or branched saturated $C_1$-$C_4$ alkyl group, or a linear or branched saturated $C_1$-$C_5$ alkyl group, or a linear or branched saturated $C_1$-$C_6$ alkyl group, or a linear or branched saturated $C_1$-$C_7$ alkyl group, or a linear or branched saturated $C_1$-$C_8$ alkyl group, or a linear or branched saturated $C_1$-$C_9$ alkyl group, or a linear or branched saturated $C_1$-$C_{10}$ alkyl group, or a linear or branched saturated $C_1$-$C_{11}$ alkyl group, or a linear or branched saturated $C_1$-$C_{12}$ alkyl group, or a linear or branched saturated $C_1$-$C_{13}$ alkyl group, or a linear or branched saturated $C_1$-$C_{14}$ alkyl group, or a linear or branched saturated $C_1$-$C_{15}$ alkyl group, or a linear or branched saturated $C_1$ alkyl group, or a linear or branched saturated $C_2$ alkyl group, or a linear or branched saturated $C_3$ alkyl group, or a linear or branched saturated $C_4$ alkyl group, or a linear or branched saturated $C_5$ alkyl group, or a linear or branched saturated $C_6$ alkyl group, or a linear or branched saturated $C_7$ alkyl group, or a linear or branched saturated $C_8$ alkyl group, or a linear or branched saturated $C_9$ alkyl group, or a linear or branched saturated $C_{10}$ alkyl group, or a linear or branched saturated $C_{11}$ alkyl group, or a linear or branched saturated $C_{12}$ alkyl group, or a linear or branched saturated $C_{13}$ alkyl group, or a linear or branched saturated $C_{14}$ alkyl group, or a linear or branched saturated $C_{15}$ alkyl group.

In various embodiments, the linear or branched $C_1$-$C_{15}$ alkyl group may be a linear or branched $C_2$-$C_3$ alkenyl group, or a linear or branched $C_2$-$C_4$ alkenyl group, or a linear or branched $C_2$-$C_5$ alkenyl group, or a linear or branched $C_2$-$C_6$ alkenyl group, or a linear or branched $C_2$-$C_7$ alkenyl group, or a linear or branched $C_2$-$C_8$ alkenyl group, or a linear or branched $C_2$-$C_9$ alkenyl group, or a linear or branched $C_2$-$C_{10}$ alkenyl group, or a linear or branched $C_2$-$C_{11}$ alkenyl group, or a linear or branched $C_2$-$C_{12}$ alkenyl group, or a linear or branched $C_2$-$C_{13}$ alkenyl group, or a linear or branched $C_2$-$C_{14}$ alkenyl group, or a linear or branched $C_2$-$C_{15}$ alkenyl group, or a linear or branched $C_2$ alkenyl group, or a linear or branched $C_3$ alkenyl group, or a linear or branched $C_4$ alkenyl group, or a linear or branched $C_5$ alkenyl group, or a linear or branched $C_6$ alkenyl group, or a linear or branched $C_7$ alkenyl group, or a linear or branched $C_8$ alkenyl group, or a linear or branched $C_9$ alkenyl group, or a linear or branched $C_{10}$ alkenyl group, or a linear or branched $C_{11}$ alkenyl group, or a linear or branched $C_{12}$ alkenyl group, or a linear or branched $C_{13}$ alkenyl group, or a linear or branched $C_{14}$ alkenyl group, or a linear or branched $C_{15}$ alkenyl group.

In various embodiments, the linear or branched $C_1$-$C_{15}$ alkyl group may be a linear or branched $C_2$-$C_3$ alkynyl group, or a linear or branched $C_2$-$C_4$ alkynyl group, or a linear or branched $C_2$-$C_5$ alkynyl group, or a linear or branched $C_2$-$C_6$ alkynyl group, or a linear or branched $C_2$-$C_7$ alkynyl group, or a linear or branched $C_2$-$C_8$ alkynyl group, or a linear or branched $C_2$-$C_9$ alkynyl group, or a linear or branched $C_2$-$C_{10}$ alkynyl group, or a linear or branched $C_2$-$C_{11}$ alkynyl group, or a linear or branched $C_2$-$C_{12}$ alkynyl group, or a linear or branched $C_2$-$C_{13}$ alkynyl group, or a linear or branched $C_2$-$C_{14}$ alkynyl group, or a linear or branched $C_2$-$C_{15}$ alkynyl group, or a linear or branched $C_2$ alkynyl group, or a linear or branched $C_3$ alkynyl group, or a linear or branched $C_4$ alkynyl group, or a linear or branched $C_5$ alkynyl group, or a linear or branched $C_6$ alkynyl group, or a linear or branched $C_7$ alkynyl group, or a linear or branched $C_8$ alkynyl group, or a linear or branched $C_9$ alkynyl group, or a linear or branched $C_{10}$ alkynyl group, or a linear or branched $C_{11}$ alkynyl group, or a linear or branched $C_{12}$ alkynyl group, or a linear or branched $C_{13}$ alkynyl group, or a linear or branched $C_{14}$ alkynyl group, or a linear or branched $C_{15}$ alkynyl group.

In various embodiments, the $C_3$-$C_{18}$ cycloalkyl group may be a $C_3$-$C_4$ cycloalkyl group, or a $C_3$-$C_5$ cycloalkyl group, or a $C_3$-$C_6$ cycloalkyl group, or a $C_3$-$C_7$ cycloalkyl group, or a $C_3$-$C_8$ cycloalkyl group, or a $C_3$-$C_9$ cycloalkyl group, or a $C_3$-$C_{10}$ cycloalkyl group, or a $C_3$-$C_{11}$ cycloalkyl group, or a $C_3$-$C_{12}$ cycloalkyl group, or a $C_3$-$C_{13}$ cycloalkyl group, or a $C_3$-$C_{14}$ cycloalkyl group, or a $C_3$-$C_{15}$ cycloalkyl group, or a $C_3$-$C_{16}$ cycloalkyl group, or a $C_3$-$C_{17}$ cycloalkyl group, or a $C_3$-$C_{18}$ cycloalkyl group, or a $C_4$-$C_5$ cycloalkyl group, or a $C_4$-$C_6$ cycloalkyl group, or a $C_4$-$C_7$ cycloalkyl group, or a $C_4$-$C_8$ cycloalkyl group, or a $C_4$-$C_9$ cycloalkyl group, or a $C_4$-$C_{10}$ cycloalkyl group, or a $C_4$-$C_{11}$ cycloalkyl group, or a $C_4$-$C_{12}$ cycloalkyl group, or a $C_4$-$C_{13}$ cycloalkyl group, or a $C_4$-$C_{14}$ cycloalkyl group, or a $C_4$-$C_{15}$ cycloalkyl group, or a $C_4$-$C_{16}$ cycloalkyl group, or a $C_4$-$C_{17}$ cycloalkyl group, or a $C_4$-$C_{18}$ cycloalkyl group, or a $C_3$ cycloalkyl group, or a $C_4$ cycloalkyl group, or a $C_5$ cycloalkyl group, or a $C_6$ cycloalkyl group, or a $C_7$ cycloalkyl group, or a $C_8$ cycloalkyl group, or a $C_9$ cycloalkyl group, or a $C_{10}$ cycloalkyl group, or a $C_{11}$ cycloalkyl group, or a $C_{12}$ cycloalkyl group, or a $C_{13}$ cycloalkyl group, or a $C_{14}$ cycloalkyl group, or a $C_{15}$ cycloalkyl group, or a $C_{16}$ cycloalkyl group, or a $C_{17}$ cycloalkyl group, or a $C_{18}$ cycloalkyl group.

In various embodiments, the $C_3$-$C_{18}$ cycloalkyl group may be a $C_3$-$C_4$ cycloalkenyl group, or a $C_3$-$C_5$ cycloalkenyl group, or a $C_3$-$C_6$ cycloalkenyl group, or a $C_3$-$C_7$ cycloalkenyl group, or a $C_3$-$C_8$ cycloalkenyl group, or a $C_3$-$C_9$ cycloalkenyl group, or a $C_3$-$C_{10}$ cycloalkenyl group, or a $C_3$-$C_{11}$ cycloalkenyl group, or a $C_3$-$C_{12}$ cycloalkenyl group, or a $C_3$-$C_{13}$ cycloalkenyl group, or a $C_3$-$C_{14}$ cycloalkenyl group, or a $C_3$-$C_{15}$ cycloalkenyl group, or a $C_3$-$C_{16}$ cycloalkenyl group, or a $C_3$-$C_{17}$ cycloalkenyl group, or a $C_3$-$C_{18}$ cycloalkenyl group, or a $C_4$-$C_5$ cycloalkenyl group, or a $C_4$-$C_6$ cycloalkenyl group, or a $C_4$-$C_7$ cycloalkenyl group, or a $C_4$-$C_8$ cycloalkenyl group, or a $C_4$-$C_9$ cycloalkenyl group, or a $C_4$-$C_{10}$ cycloalkenyl group, or a $C_4$-$C_{11}$ cycloalkenyl group, or a $C_4$-$C_{12}$ cycloalkenyl group, or a $C_4$-$C_{13}$ cycloalkenyl group, or a $C_4$-$C_{14}$ cycloalkenyl group, or a $C_4$-$C_{15}$ cycloalkenyl group, or a $C_4$-$C_{16}$ cycloalkenyl group, or a $C_4$-$C_{17}$ cycloalkenyl group, or a $C_4$-$C_{18}$ cycloalkenyl group, or a $C_3$ cycloalkenyl group, or a $C_4$ cycloalkenyl group, or a $C_5$ cycloalkenyl group, or a $C_6$ cycloalkenyl group, or a $C_7$ cycloalkenyl group, or a $C_8$ cycloalkenyl group, or a $C_9$ cycloalkenyl group, or a $C_{10}$ cycloalkenyl group, or a $C_{11}$ cycloalkenyl group, or a $C_{12}$ cycloalkenyl group, or a $C_{13}$ cycloalkenyl group, or a $C_{14}$ cycloalkenyl group, or a $C_{15}$ cycloalkenyl group, or a $C_{16}$ cycloalkenyl group, or a $C_{17}$ cycloalkenyl group, or a $C_{18}$ cycloalkenyl group.

In various embodiments, the $C_3$-$C_{18}$ cycloalkyl group may be a $C_3$-$C_4$ cycloalkynyl group, or a $C_3$-$C_5$ cycloalkynyl group, or a $C_3$-$C_6$ cycloalkynyl group, or a $C_3$-$C_7$ cycloalkynyl group, or a $C_3$-$C_8$ cycloalkynyl group, or a $C_3$-$C_9$ cycloalkynyl group, or a $C_3$-$C_{10}$ cycloalkynyl group, or a $C_3$-$C_{11}$ cycloalkynyl group, or a $C_3$-$C_{12}$ cycloalkynyl group, or a $C_3$-$C_{13}$ cycloalkynyl group, or a $C_3$-$C_{14}$ cycloalkynyl group, or a $C_3$-$C_{15}$ cycloalkynyl group, or a $C_3$-$C_{16}$ cycloalkynyl group, or a $C_3$-$C_{17}$ cycloalkynyl group, or a $C_3$-$C_{18}$ cycloalkynyl group, or a $C_4$-$C_5$ cycloalkynyl group, or a $C_4$-$C_6$ cycloalkynyl group, or a $C_4$-$C_7$ cycloalkynyl group, or a $C_4$-$C_8$ cycloalkynyl group, or a $C_4$-$C_9$ cycloalkynyl group, or a $C_4$-$C_{10}$ cycloalkynyl group, or a $C_4$-$C_{11}$ cycloalkynyl group, or a $C_4$-$C_{12}$ cycloalkynyl group, or a $C_4$-$C_{13}$ cycloalkynyl group, or a $C_4$-$C_{14}$ cycloalkynyl group, or a $C_4$-$C_{15}$ cycloalkynyl group, or a $C_4$-$C_{16}$ cycloalkynyl group, or a $C_4$-$C_{17}$ cycloalkynyl group, or a $C_4$-$C_{18}$ cycloalkynyl group, or a $C_3$ cycloalkynyl group, or a $C_4$ cycloalkynyl group, or a $C_5$ cycloalkynyl group, or a $C_6$ cycloalkynyl group, or a $C_7$ cycloalkynyl group, or a $C_8$ cycloalkynyl group, or a $C_9$ cycloalkynyl group, or a $C_{10}$ cycloalkynyl group, or a $C_{11}$ cycloalkynyl group, or a $C_{12}$ cycloalkynyl group, or a $C_{13}$ cycloalkynyl group, or a $C_{14}$ cycloalkynyl group, or a $C_{15}$ cycloalkynyl group, or a $C_{16}$ cycloalkynyl group, or a $C_{17}$ cycloalkynyl group, or a $C_{18}$ cycloalkynyl group.

In various embodiments, the linear or branched $C_1$-$C_{15}$ alkyl group or the $C_3$-$C_{18}$ cycloalkyl group may be intercepted with at least one heteroatom that may independently be O, S, N or P; or S, N or P; or O, N or P; or O, S, or P; or O, S, or N; or N or P; or S or P; or S or N; or O or P; or O or N; or O or S; or P; or N; or S; or O.

In various embodiment, the $C_1$-$C_{15}$ alkyl group or the $C_3$-$C_{15}$ cycloalkyl group may be substituted with one or more substituents selected from the group consisting of F, Cl, Br, I, —N$^+$($C_{1-15}$alkyl)$_3$, —N$^+$($C_{2-15}$alkenyl)$_3$, —N$^-$($C_{2-15}$alkynyl)$_3$, —N$^+$H($C_{1-15}$alkyl)$_2$, —N$^+$H($C_{2-15}$alkenyl)$_2$, —N$^+$H($C_{2-15}$alkynyl)$_2$, —P$^+$($C_{1-15}$alkyl)$_3$, P$^+$($C_{2-15}$alkenyl)$_3$, P$^-$($C_{2-15}$alkynyl)$_3$, S$^+$($C_{1-15}$alkyl)$_2$, S$^+$($C_{2-15}$alkenyl)$_2$, S$^+$($C_{2-15}$alkynyl)$_2$, oxo (i.e., =O), —O$C_{1-15}$alkyl, unsubstituted or substituted aromatic $C_3$-$C_{18}$ cycloalkyl, unsubstituted or substituted non-aromatic $C_3$-$C_{18}$ heterocyclic group, unsubstituted or substituted aromatic $C_3$-$C_{18}$ heterocyclic group, =NH, —$C_1$-$C_{15}$alkyl, non-aromatic $C_3$-$C_{18}$ cycloalkyl, —N($C_{1-15}$alkyl)$_2$, —N($C_{2-15}$alkenyl)$_2$, —N($C_{2-15}$alkynyl)$_2$, —COOH, —NH$_2$, —SH, a biomolecule, and a linking group optionally joined to a biomolecule. In various embodiments, the $C_1$-$C_{15}$ alkyl group or the $C_3$-$C_{18}$ cycloalkyl group may be substituted with one or more substituents selected from the group consisting of F, Cl, Br, I, —N$^+$($C_{1-15}$alkyl)$_3$, —N$^+$($C_{2-15}$alkenyl)$_3$, —N$^+$($C_{2-15}$alkynyl)$_3$, —N$^+$H($C_{1-15}$alkyl)$_2$, —N$^+$H($C_{2-15}$alkenyl)$_2$, —N$^+$H($C_{2-15}$alkynyl)$_2$, P$^+$($C_{1-15}$alkyl)$_3$, P$^+$($C_{2-15}$alkenyl)$_3$, P$^-$($C_{2-15}$alkynyl)$_3$, S$^+$($C_{1-15}$alkyl)$_2$, S$^+$($C_{2-15}$alkenyl)$_2$, S$^+$($C_{2-15}$alkynyl)$_2$, oxo (i.e., =O), —O$C_{1-15}$alkyl, unsubstituted or substituted aromatic $C_3$-$C_{18}$ cycloalkyl, unsubstituted or substituted non-aromatic $C_3$-$C_{18}$ heterocyclic group, unsubstituted or substituted aromatic $C_3$-$C_{18}$ heterocyclic group, —$C_1$-$C_{15}$alkyl, non-aromatic $C_3$-$C_{18}$ cycloalkyl, —N($C_{1-15}$alkyl)$_2$, —N($C_{2-15}$alkenyl)$_2$, —N($C_{2-15}$alkynyl)$_2$, —COOH, —NH$_2$, —SH, a biomolecule, and a linking group optionally joined to a biomolecule. In various embodiments, the $C_1$-$C_{15}$ alkyl group or the $C_3$-$C_{18}$ cycloalkyl group may be substituted with one or more substituents selected from the group consisting of a biomolecule and a linking group optionally joined to a biomolecule.

The compounds may also include base-free forms, prodrugs, or pharmaceutically acceptable salts thereof. The compounds described herein are meant to include all racemic mixtures and all individual enantiomers or combinations thereof, whether or not they are represented herein.

Various embodiments of the invention provide a method of making a precursor compound which comprises converting a corresponding alkylboronic acid variant of any of the aforementioned compounds to an alkylboronic ester, wherein one, two or three of $Y^1$ and $Y^2$ may be a leaving group displaceable by fluoride. This invention also provides a method of making a $^{18}F$ containing compound which comprises replacing at least one of said leaving group or groups of the aforesaid alkylboronic ester with $^{B}F$. Methods of this invention make use of substituted alkyl-boronic compounds, wherein $Y^1$ or $Y^2$ may be a moiety that can be displaced by reaction with fluoride. These may be used as precursor molecules to the above-described $^{18}F$ labeled alkyfluoroborate compounds by reaction with a suitable source of $^{18}F$. In this aspect of the invention, $Y^1$ or $Y^2$ may (for example) be an alkoxy, halide, amine (e.g. alkyl, aryl), or thiol (alkyl, aryl) moiety. Other examples of leaving groups that can be displaced by fluoride are known. Particular examples are described in WO 2005/077967.

Alkylfluoroborate compounds according to a formula described herein may be made by a variety of synthetic methods, ranging in complexity from de novo synthesis to a 'wash-in' of the fluorine on a previously prepared boronate (see, for example, Molander et al., J. Org. Chem. 2010, 75, 4304-4306; Lennox et al. JACS, 2012, 134, 7431-7441; Dumas et al., Organic Letters, 2012, 14, 2138-2141; and Molander et al., Organic Letters, 2006, 8, 2031-2034).

A 'wash-in' preparative method may include preparation of a solution of a substituted alkylboronic acid or ester in an appropriate solvent, to which aqueous fluoride is added. The pH may be at a suitable range (e.g. about 2.5 to about 3.5) or according to what is suitable for the solvents and the substituted alkylboronic acid or ester. The solvent may be DMF or another solvent that is miscible with an aqueous fluoride solution, and solubilizes the substituted alkylboronic acid or ester of interest. Examples of such solvents may include aqueous mixtures comprising DMSO, DMF, MeOH, THF, MeCN, DMA, and NMP. Selection of a particular solvent may vary with the particular substituted alkylboronic acid or ester and in particular with regards to preserving the bioactivity of the biomolecule, and is within the skill of one versed in the art. Aqueous fluoride may be at any suitable concentration. For example, the substituted alkylboronic acid may be present at a concentration of about 1-4 mM, and the $KH^{18/19}F_2$ may be present in 3 or 4 equivalents i.e. 3-12 mM or 4-16 mM, where the minimal concentrations are selected to increase the specific activity of the labeling, and the maximal concentrations determined by the maximal solubility of the bioconjugate.

Clinical preparations of a substituted alkylboronic acid or ester may involve use of about 800 mCi $^{18}F$ in no carrier added form, which, barring environmental contamination with $^{19}F$, represents about 0.46 nmol of $^{18}F$, or 3.8% of the total fluoride used in a 10 μL reaction at 12 mM total fluoride. Microreactor and microfluidic techniques, (which provide reaction volumes of about 50 nL) can reduce the quantity of carrier $^{19}F$ needed. For instance in a 50 nL reaction at 10 mM fluoride, one needs only 500 pmol of total fluoride. Thus, a no carrier added reaction is readily contemplated for labeling alkylboronic acids.

Reaction temperature may be increased above room temperature, but below a temperature that may destabilize or denature the selected biomolecule. For example, some nucleic acids or oligonucleotides may be suitable for use in labeling reactions at temperatures of about 60° C., while some proteins may require lower temperatures. Peptides are known to withstand temperatures as high as about 110° C. Antibodies are known in the art to have limited thermostability compared to most other proteins however thermostable antibodies and enzymes may also be suitable for use in labeling reactions at temperatures above room temperature. Alternatively, some biomolecules may be preferentially suitable for labeling reactions at reduced temperatures, i.e. below room temperature.

General approaches and methods for direct chemical modification of biomolecules for addition and/or substitution of modifying groups are known. As an example, chemical modification of proteins is described by Means and Feeney *Bioconjugate Chemistry* 1990 1: 2-12). Chemical modification of nucleic acids such as DNA and RNA is described in, for example, Boutourine et al. *Bioconjugate Chemistry* 1990 1:350-56. Chemical modification of sugars and oligosaccharides is described in, for example Wood et al. *Bioconjugate Chemistry* 1992 3: 391-6 and more recently in click reactions In various embodiments, there is provided a method for selections or screening substituted organotrifluoroborate compounds, for their ability to resist defluoridation as an indicator of their longevity as a radio imaging agent for PET. Various methods may be employed such as described below.

Chromatographic methods for separation of a fluoridated compound from the free $^{18}F$ are useful for qualitative or semi-quantitative assessment of the resistance to defluoridation of the fluoridated compound. Such methods generally involve a stationary phase, which may be a column matrix having qualities such as hydrophobicity, porosity or size-exclusion capabilities, charge, hydrophilicity or the like. Alternately, the stationary phase may provide structural support only, and be largely inert to interactions with a mobile phase or the solutes in the mobile phase. The stationary phase may be further supported in, for example, a column, or for thin-layer chromatography, on a glass plate. Paper used in paper chromatography may provide both the stationary phase and physical support of the stationary phase. Alternatively a diol column can be used to remove unlabelled boronic acid that may be present as unreacted starting material or following competing solvolysis of the organotrifluoroborate during labeling. The mobile phase is frequently a solvent, which may be hydrophobic or hydrophilic, aqueous or non-aqueous, and may be formulated to provide a fixed pH or a selected pH range, or a particular salt or other solute concentration. In various embodiments, the molecules or compounds of interest, such as the fluoridated compounds above are soluble in the mobile phase, as is the free fluorine that is to be separated from the fluoridated compound. Choice of a particular chromatographic method may be influenced by the molecule to be separated. For example, separation of a labeled biomolecule, such as an antibody, gel-permeation or affinity chromatography may be suitable. In another example, separation of a labeled oligonucleotide or peptide, anion exchange chromatography may be suitable. In another example, separation of labeled biotin complexed with an avidin-conjugate may involve gel-permeation chromatography. In another example, separation of labeled free biotin, folate or methotrexate or other small molecules, such as peptides may involve chromatographic separation through a silica column or plug, or HPLC/FPLC.

General principles, methods and background relating to chromatography are known, and may be found in, for example, Jonsson, J. A. Chromatographic Theory and Basic Principles. 1987. Marcel Dekker, or Ahuja S. Chromatography and Separation Science. 2003. Elsevier Press; Cox, G. B. Preparative Enantioselective Chromatography. 2005. Blackwell Publishing; Wall, P. E. Thin-layer chromatography: a modern practical approach 205. Royal Society of Chemistry; Sherma, J. and Fried, B. Handbook of Thin-layer chromatography. 2003. Marcel Dekker.

$^{19}$F-NMR may be also used to monitor defluoridation (e.g. see Ting et. al. (2008) J. Org. Chem. 73:4662-70; Hartwig et. al. (2008) Tetrahedron Letters 49:3152-56; and, Ting et. al. (2008) Journal of Fluorine Chemistry 129:349-58).

Isotopic wash-out or pulse-chase methods may also be used for screening labeled trifluoroborates in order to identify compositions that are suitably stable for use as imaging agents.

It is recognized that stable organotrifluoroborates (no $^{18}$F incorporated) may be useful as radiochemically stable precursors that will find use in labeling whereby they are treated under acidic conditions to promote the exchange of an atom of $^{19}$F for an atom of $^{18}$F. Following labeling, at least one of F may be $^{18}$F. It may be recognized that in the preparation of compounds of this invention, that there may be a fraction of molecules that will not be complexed with any $^{18}$F when carrier $^{19}$F may be used. It may be recognized that the addition of carrier $^{19}$F may be advantageous in certain cases. A final/overall specific activity suitable for imaging purposes can be achieved even if a particular trifluoroborate molecule in a mixture contains no $^{18}$F, provided that at least some of the trifluoroborates prepared contain at least one 18F.

Other aspects and features of the present invention will become apparent to those ordinarily skilled in the art upon review of the following description of specific embodiments of the invention in conjunction with the accompanying figures.

EXAMPLES

Aryltrifluoroborates undergo solvolysis (i.e., B—F bond scission) at a nearly pH-independent rate above pH 3. The electronic nature of the ring substituents is the main factor affecting the rate of solvolysis. Groups on aryl rings impart their effects on rates by both inductive and resonance effects whereby the electron density in the pi-bonds is increased or diminished. Increased pi electron density can delocalize from the ring into the sp2 orbital on boron to promote loss of one fluoride ion whereupon the other two are lost rapidly. Increasing the electron density results in an enhancement of the rate of B—F bond scission, whereas decreasing the electron density reduces the rate. The inductive effects are difficult to separate from those related to resonance, and both effects are further nuanced by whether the substituents are in the meta vs ortho/para positions. Moreover, it is critical to understand the magnitude of these effects in order to understand how to create aryltrifluoroborates with sufficient stability.

The magnitude of these effects may be given by the ρ value in a quantitative linear free energy relationship. The effects of substitution by several (at least two) electron withdrawing group may be estimated by summing their known σ values. The rate at which such a composition reacts can be related to the rate of an unsubstituted aryl-BF$_3$ by the following equation (log(k/k0)=σρ where k is the solvolysis rate constant for a certain aryl-BF$_3$ under consideration and k0 is the solvolysis rate constant for an unsubstituted aryl-BF$_3$ Thus, for aryl-BF$_3$ solvolysis, the relationship between the rate of B—F bond scission and the number and position of various electron withdrawing groups may be understood in terms of known σ values and a value of p~−1. Furthermore, owing to the change in the hybridization of boron from sp3 to sp2 upon loss of a first fluoride ion, which places the remaining two fluorine atoms co-planar with the aryl ring, it has been recognized that bulky ortho substituents may exert steric effects to retard solvolysis.

While aryl-trifluoroborate solvolysis can be understood in terms of delocalization of electron density from the arene pi-system into the empty p-orbital on boron with concomitant expulsion of a fluoride atom whose rate is correlated by the Hammett relationship of (log(k/k0)=σρ where ρ~−1, this understanding based on a combination of inductive effects and pi-delocalization effects, as expressed in the pKa of (aryl) benzoic acids, and cannot be extended to substituted nonaromatic organotrifluoroborates. Electron withdrawing groups can greatly affect the rate of a reaction in some cases, but not in others, and thus the application of linear free energy relationships that hold well for aryl systems do not necessarily apply to nonaromatic compositions. It was unclear to what extent such relationships could be extended to the rate of B—F bond scission in systems where the carbon atom to which the boron is attached is not in an aromatic state, and of what magnitude these effects would be.

Example 1: Fluoridation of a Organoboronic Acid or Ester 22.4 mg (0.10 mmol) of N,N,-dimethyl-N-propargylammoniomethylborate pinacol ester was dissolved with 80 μL of DMF, then 2.4 equiv. 120 μL of 3 M KHF$_2$ (aqueous solution) and 80 μL of 4 M HCl (aqueous solution) were added as the fluoridation reagents. This reaction was incubated at 37° C. for two hours, then it was concentrated with a vacuum concentrator (Speedvac). A yellowish white powder was achieved and was ready for further purification.

Example 2: Evaluation of Rates of Solvolytic Defluoridation of Fluoridated Organotrifluoroborates by $^{19}$F-Nuclear Magnetic Resonance ($^{19}$F-NMR) Spectroscopy The following is are representative examples of testing of solvolytic defluoridation of fluoridated organoborates as shown in FIG. 1A to FIG. 1FF and Table 1. Solutions of the fluoridated organotrifluoroborates were made by dissolving 30 mg of the fluoridated organotrifluoroborate into 1 mL of 20% ethanol/acetonitrile.

Figure 1B:
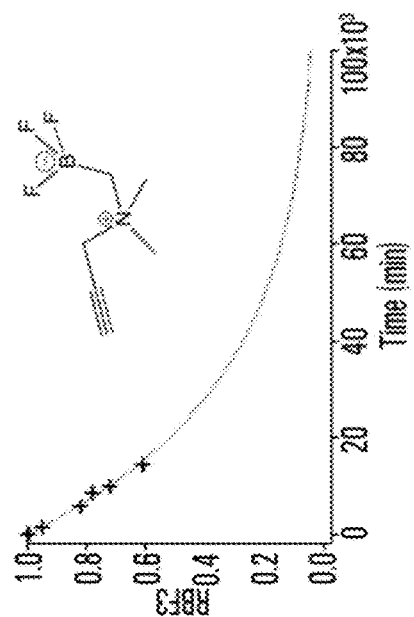

As the fluoridated organotrifluoroborate salts were often contaminated with a significant amount of free fluoride, a silica column was used to remove the free fluoride from the organotrifluoroborate solution. After loading the crude reaction onto the silica column, the fractions containing the desired organotrifluoroborate were eluted and combined to form a combined solution. In view of the strong stability of the fluoridated organotrifluoroborate in organic solvent, 20% of the combined solution was stored in an NMR tube and this sample served as the "zero" minute time point. A purified organotrifluoroborate salt was isolated from the remaining portion of the combined solution (remaining 80% of the combined solution) by removing the organic solvent from the combined solution by vacuum. Removal of the organic solvent from the combined solution gave the purified fluoridated alkylbornate salt in the form of a white solid. The dry and purified fluoridated organotrifluoroborate salt was re-dissolved into 3 mL of 200 mM phosphate buffer. Solvolytic defluoridation started immediately upon dissolution of the fluoridated organotrifluoroborate salt into phosphate buffer, and accordingly, the time was recorded at the moment of dissolution. The progress of solvolytic defluoridation of the fluoridated organotrifluoroborate salt was monitored using $^{19}$F NMR spectroscopy. General principles, methods and background relating to the use of $^{19}$F NMR spectroscopy for monitoring defluoridation are known, and may be found in, for example, Ting et al. (2008, J. Org. Chem. 73; 4662-70; Harwig et al. (2008) Tetrahedron Letters 49:3152-56; and Ting et al. (2008) Journal of Fluorine Chemistry 129:349-58. For each time point, solvolytic defluoridation data was collected using a 300 MHz $^{19}$F NMR spectrometer (Bruker). $^{19}$F NMR spectroscopic tracers for the fluoridated organotrifluoroborate salt at different times are shown in FIG. 1A. Use of $^{19}$F-NMR to measure solvolytic defluoridation provides a useful model for measuring solvolytic 18F-defluoridation because if one F is lost, all are lost. Moreover, it is understood that the kinetic isotope effect in terms of B—F bond solvolysis is negligible. Hence whereas for PET scanning purposes solvolytic 18F-defluoridation is of consideration, $^{19}$F-NMR provides a reliable measure of the rate of 18F-defluoridation since both $^{18}$F and $^{19}$F rates are the same in practice because there should be no measureable isotopic difference. The degree of solvolytic defluoridation of the fluoridated organotrifluoroborate salt was plotted as a function of time, for example, as shown in FIG. 1B for Compound 6 of Table 1. $^{19}$F NMR spectroscopic tracers for the fluoridated organotrifluoroborate salts of compounds listed in Table 1 at different times are shown in FIGS. 1A, 1C, 1E, 1G, 1I, 1K, 1M, 1O, 1Q, 1S, 1U, 1W, 1Y, 1AA, 1CC, and 1EE, and the degree of solvolytic defluoridation of the compounds as a function of time is shown in FIGS. 1B, 1D, 1F, 1H, 1J, 1L, 1N, 1P, 1R, 1T, 1V, 1X, 1ZZ, 1BB, 1DD, and 1FF. As can be seen from FIGS. 1B, 1D, 1F, 1H, 1J, 1L, 1N, 1P, 1R, 1T, 1V, 1X, 1ZZ, 1BB, 1DD, and 1FF, solvolytic defluoridation of the fluoridated organoborate salts shows pseudo first-order reaction kinetics.

Example 3: Rate Constant for Solvolytic Defluoridation

Figure 1D:
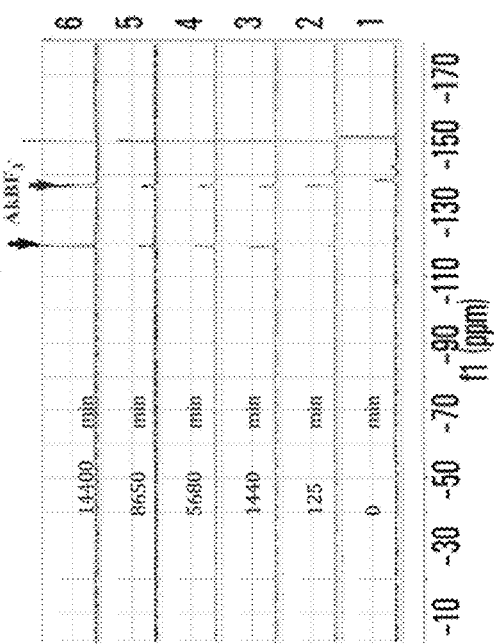

The time curves shown in FIGS. 1B and 1D were fitted and a rate constant, $k_{solvolysis}$, for each time curve was calculated. As a measure of the stability of the fluoridated organoborate to solvolytic defluoridation, $pk_{B-F}$ values were calculated using the equation $pk_{B-F}=-\log(k_{solvolysis})$. In addition to $pk_{B-F}$ values, observed solvolytic defluoridation half-life, $t_{1/2}$, values and rate constants, $k_{solvolysis}$, for a number of different fluoridated organoborates are listed in Table 1. As can be seen from Table 1, the larger the $pk_{B-F}$ value, the more stable the fluoridated organoborate was observed to be to solvolytic defluoridation.

TABLE 1

Rate Constant Data for Solvolytic Defluoridation of Fluoridated Organoborate Compounds

| Compound No. | Structure | pKa of Corresponding COOH† | pk (solvolysis) = −log k(solvolysis) | k(solvolysis) in units of min − 1 | half-life, t1/2 (min.) |
|---|---|---|---|---|---|
| 1 | 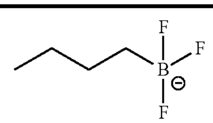 | 4.81 | 0.52 | 0.3 | 2.3-3 |
| 2 | 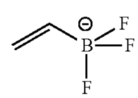 | 4.25 | 1.01 | 0.099 | 7 |
| 3 | 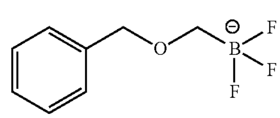 [SMILES: F[B-](F)(F)COCc1ccccc1] | 3.53 | 2.32 | 0.00476 | 145 |
| 4 | 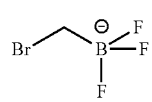 | 2.86 | 2.98 | 0.000768 | 658 |
| 5 | 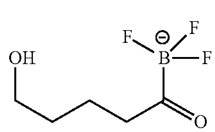 [SMILES: O=C(CCCCO)[B-](F)(F)F] | 2.5 | 3.5249 | 0.000298 | 2311 |
| 6 | 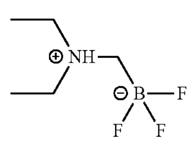 | 2.34 | 3.7554 | 0.000175 | 3929 |

TABLE 1-continued

Rate Constant Data for Solvolytic Defluoridation of Fluoridated Organoborate Compounds

| Compound No. | Structure | pKa of Corresponding COOH† | pk (solvolysis) = −log k(solvolysis) | k(solvolysis) in units of min − 1 | half-life, t1/2 (min.) |
|---|---|---|---|---|---|
| 7 | 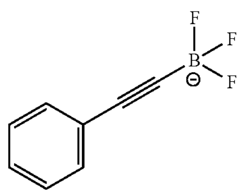 [SMILES: F[B-](F)(F)C#Cc1ccccc1] | 2.45 | 3.7409 | 0.000181 | 3800 |
| 8 | 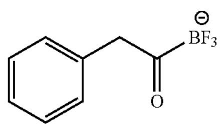 | 2.35 | 4.0700 | $8.52 \times 10{-5}$ | 8100 |
| 9 | 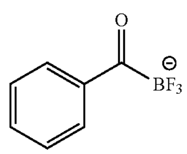 | 2.15 | 4.1823 | $6.57 \times 10^{-5}$ | 10500 |
| 10 | 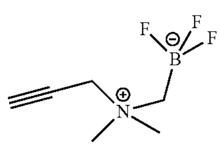 | 1.83 | 4.5036 | $3.14 \times 10^{-5}$ | 22000 |
| 11 | 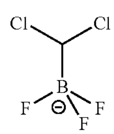 | 1.29 | 5.3372 | $4.6 \times 10^{-5}$ | 150000 |
| 12 | 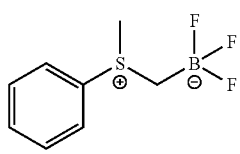 | 0.93* | 5.82 | $1.5 \times 10^{-5}$ | 460000 |
| 13 | 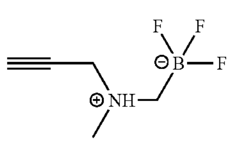 | 2.34 | 3.77 | 0.000170 | 4053 |
| 14 | 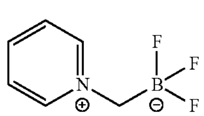 [SMILES: F[B-](F)(F)C[n+]1ccccc1] | 2.14 | 4.19 | $6.45 \times 10^{-5}$ | 10700 |
| 15 | 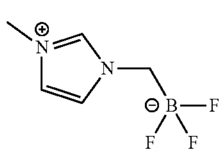 | 3.2* | 2.59 | 0.00259 | 266 |

TABLE 1-continued

Rate Constant Data for Solvolytic Defluoridation of Fluoridated Organoborate Compounds

| Compound No. | Structure | pKa of Corresponding COOH† | pk (solvolysis) = −log k(solvolysis) | k(solvolysis) in units of min − 1 | half-life, t1/2 (min.) |
|---|---|---|---|---|---|
| 16 | 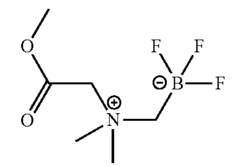 | 2.1* | 4.17 | 0.0000673 | 10300 |
| 17 | 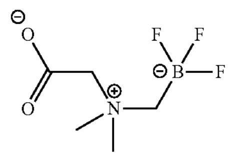 | 3.15* | 2.70 | 0.0020 | 346 |
| 18 | 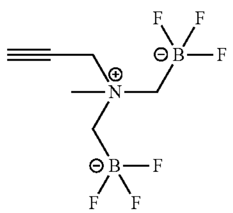 | 2.5* | 3.61 | 0.0002460 | 2818 |

†For example, pKa of the corresponding COOH to Compound 1 would be the pKa of the corresponding carboxylic acid

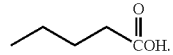COH.

* = predicted by calculation

It has been reported that aryltrifluoroborates can be considerably stabilized by an electron-poor environment (see, for example, Ting et al. (2008, J. Org. Chem. 73; 4662-70). It has also been reported that EWGs (electron withdrawing group) on the benzene ring can significantly slow down hydrolysis, resulting in longer solvolytic half-lives. A similar correlation with such substituent effects is seen with regards to the nitration of benzene or the solvolysis of substituted benzyl tosylates. Without being bound by theory, a possible mechanistic reason for this effect was that pi-electrons in the aryl ring could delocalize into the empty p-orbital on boron thus promoting B—F bond dissociation. As such, a group that weakened this effect could result in greater B—F bond stability. However, in contrast to aryltrifluoroborates, for organotrifluoroborates, there may or may not be pi-overlap by an electron withdrawing group and hence there is no reason a priori to have thought that electron withdrawing groups would have any effects on the B—F bond stability or to what extent they might have retarded solvolysis.

The existance of any relationship between $pk_{B-F}$ observed for a particular alkyl moiety of the fluoridated organotrifluoroborate compound and the pKa of a carboxylic acid conjugated to the same alkyl moiety was also investigated. The pKa values for the carboxylic acids conjugated to the same alkyl moieties of the fluoridated organotrifluoroborates tabulated in Table 1 are also included in the same table. For example, for comparison purposes with $pk_{B-F}$ for Compound 1 of Table 1, the pKa of the carboxylic acid

Figure 2:
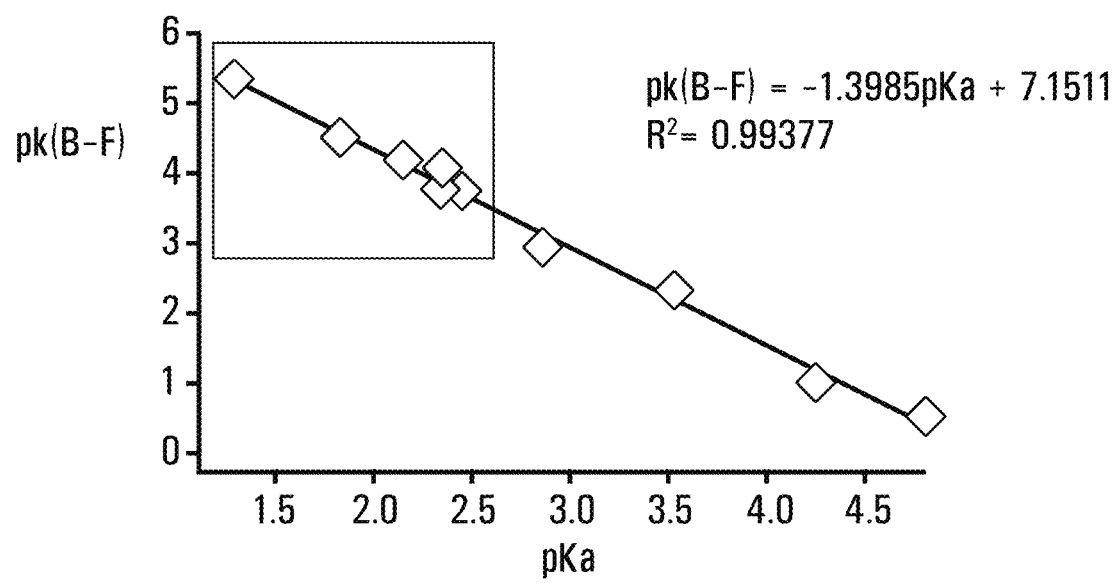
FIG. 2 shows $pk_{B-F}$ values ($pk_{B-F}$=-log $k_{solvolysis}$) of a number of fluoridated organotrifluoroborates i.e. $RBF_3^-$ compositions plotted as a function of the pKa values for the corresponding carboxylic acid RCOOH. The slope of the graph may be represented as pk(B—F)=-1.40 pKa+7.12 ($R^2$=0.994).

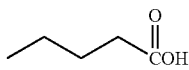

is also listed in Table 1. $pk_{B-F}$ values for a number of fluoridated organotrifluoroborates were plotted as a function of the pKa values for the corresponding carboxylic acids as shown in FIG. 2. Unexpectedly, a simple yet previously unknown relationship was observed between pKa and $pk_{B-F}$ as seen in FIG. 2, i.e. that the log of the pseudo-first order solvolytic rate constant, log $k_{solv.}$(B—F), of $RBF_3$ is correlated to the pKa of the corresponding carboxylic acid RCOOH (R=0.99) with a slope of ~1.4. Without being bound by theory, one possible explanation for this relationship could involve consideration of the impact of various substituents on the electronic environment experienced by the carboxylic acid and in turn, the impact of the various substituent groups on the dissociability of the carboxylic acid proton. The observation of a relationship between the pKa and $pk_{B-F}$ values also provides, in turn, an unexpected relationship between the pKa values and the stability or half-life of the fluoridated organotrifluoroborate compounds in terms of solvolytic defluoridation. A pKa of 2.85 or lower for the corresponding COOH may inform the design of organotrifluoroborate compositions with solvolytic half-lives of about 1000 min or longer. The box provides an approximate range that is indicative, although not determinative, of preferred utility.

This discovery now permits the stability of such organotrifluoroborate structures to be predicted, such that candidates for organoorganotrifluoroborates that will be useful in imaging may be selected and tested. A person skilled in the art of synthesis may consider the pKa of any carboxylic acid (with whatever modifications) by measurement or which is known (e.g. Jencks, Bordwell, CRC Handbook) or predicted by computer simulation, and use this knowledge to contemplate and design alkyltrifluoroborate structures that would have sufficiently long half-lives for use in the production of radiotracers.

Accordingly, a person skilled in the art may exploit this newly discovered relationship to identify candidate organotrifluoroborate compounds that are most likely to be useful as imaging agents. However, the invention is in no way limited to compounds that follow this relationship. Even though certain useful nonaromatic substituted oragnotrifluoroborate structures may deviate from this relationship when considered based solely on the pKa of a corresponding carboxylic acid, a person skilled in the art will understand that certain second order effects may dampen or accentuate the impact of various substituents on the electronic environment. Such deviations may easily be understood in terms of second-order effects related to steric interactions, to the presence of a second ionizable or charged group, or to other constraints that become clear in light of this relationship. Moreover, this relationship may guide the person skilled in the art when considering compounds that have no corresponding carboxylic acid.

This relationship also allows an electron withdrawing group to be placed as close to the boron as the carbon to which the boron is attached, whereas the geometry of an aryl ring requires that any electron withdrawing group be placed at least two carbon atoms away from the boron.

Example 4: Evaluation of Stability of $^{18}$F-Radiolabeled Fluoridated Organotrifluoroborates by Thin Layer Chromatography (TLC)

Figure 3:
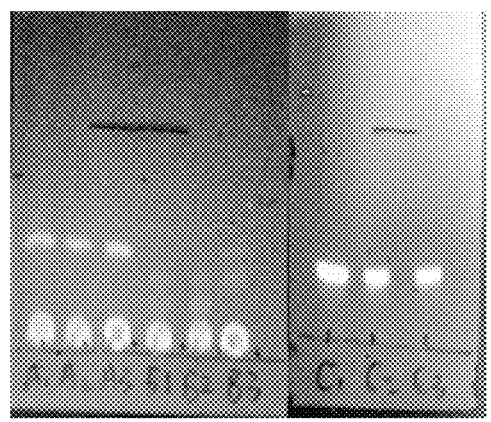
FIG. 3 shows TLC chromatograms for Rhodamine-$ArBF_3$, Rhodamine-$PyrBF_3$, and Rhodamine-Compound 9 of Table 1. The symbols A, B, C represent Rhodamine-$ArBF_3$, Rhodamine-$PyrBF_3$, and Rhodamine-Compound 9 of Table 1, respectively. The subscript numbers 1, 2, 3 represent different test conditions: Plasma 1, Plasma 2 and PBS buffer (Plasma 1 and Plasma 2 were acquired from different mice).

The following is a representative example of testing of solvolytic defluoridation of a fluoridated organotrifluoroborate as shown in FIG. 3. 2 nmol Rhodamine-BF$_3$ was added into 100 µL plasma, and then incubated at 37° C. After 2 hours, 200 µL acetonitrile (ACN) was added to precipitate the protein from the solution. The crude was filtered with 40 µm filter paper, and then a reddish purple solution was achieved. 1 µL of this solution was loaded on the TLC plate. The TLC plate was developed by 15% methanol/DCM. The TLC chromatograms for an aryltrifluoroborate (Rhodamine-ArBF$_3$), Rhodamine-PyrBF$_3$, and a quaternary ammoniomethyltrifluoroborate (Rhodamine-Compound 10 of Table 1) are shown as FIG. 3.

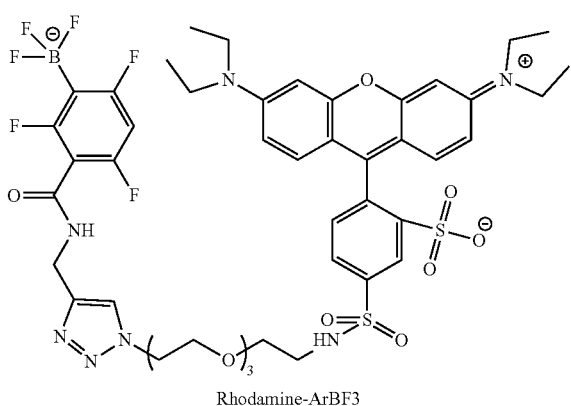

Rhodamine-ArBF3

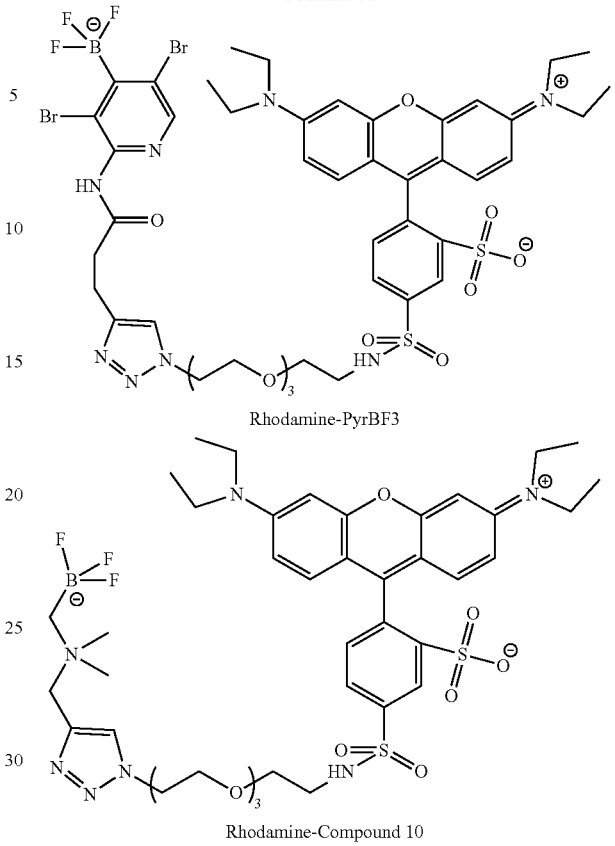

Rhodamine-PyrBF3

Rhodamine-Compound 10

In the TLC chromatograms, Rhodamine B was conjugated with the trifluoroborate to trace the decomposition. The hydrolyzed product lost the negative charge, and therefore migrated much more rapidly than the precursor. Based on the TLC chromatograms the ArBF$_3$ showed decomposition after incubation in plasma for two hours. PyrBF$_3$ exhibited greater stability than ArBF$_3$ because less decomposition was detected on the TLC chromatogram. Moreover, for Compound 10 of Table 1, almost no hydrolyzed product was detected based on the fluorescence analysis. The lack of detection of hydrolyzed product for Compound 10 of Table 1 suggests that Compound 10 has extraordinary stability in plasma and may also show excellent stability in animal models.

Example 4. Evaluation of Stability of $^{18}$F-Radiolabeled Fluoridated Organotrifluoroborates by High-Performance Liquid Chromatography (HPLC)

1.1 mCi of $^{18}$F-Compound 10 ($^{18}$F-ammoniomethyltrifluoroborate) was mixed with 100 µL of plasma to form a $^{18}$F-Compound 10-plasma mixture, and then incubated at 37° C. for two hours. 200 uL of acetonitrile (ACN) was then added to the $^{18}$F-Compound 10-plasma mixture to precipitate the protein from the mixture. The precipitated protein portion was separated from the mixture by filtration with 40 µm filter paper, and the clear filtrate was injected into an HPLC for stability analysis. Chromatograms for independent HPLC tests of Rhodamine-Compound 10 of Table 1 at 0 minutes (A), 80 minutes (B), 150 minutes (C), 0 minutes (D), 150 minutes (E), and 150 minutes (F) are shown in FIG.

Figure 4A:
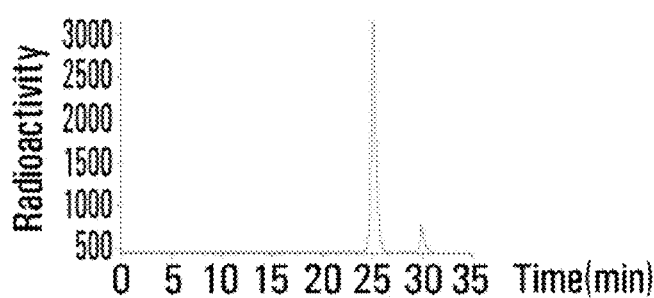
FIG. 4A shows an HPLC chromatogram for investigating the serum stability of Rhodamine-Compound 10 of Table 1 at 0 minutes.
Figure 4B:
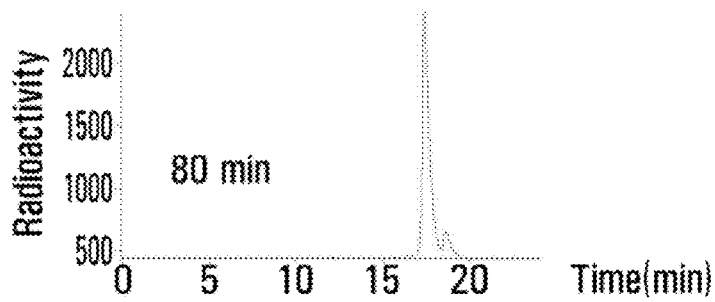
FIG. 4B shows an HPLC chromatogram for investigating the serum stability of Rhodamine-Compound 10 of Table 1 at 80 minutes.
Figure 4C:
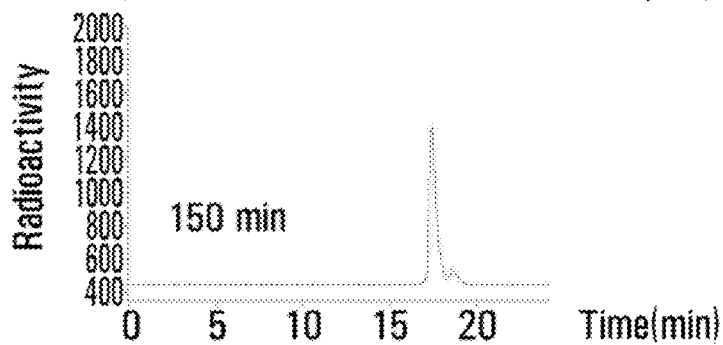
FIG. 4C shows an HPLC chromatogram for investigating the serum stability of Rhodamine-Compound 10 of Table 1 at 150 minutes.
Figure 4D:
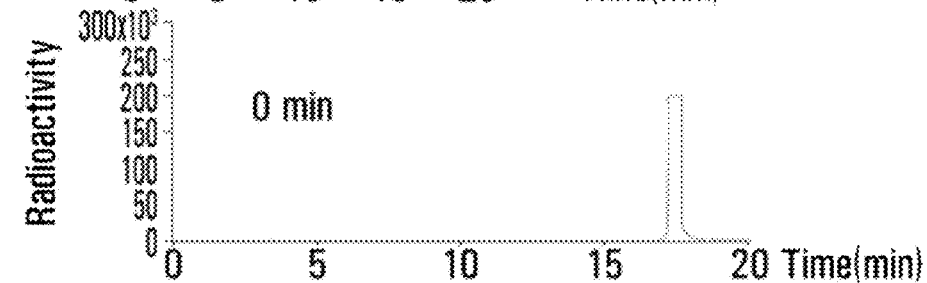
FIG. 4D shows an HPLC chromatogram for investigating the serum stability of Rhodamine-Compound 10 of Table 1 at 0 minutes.
Figure 4E:
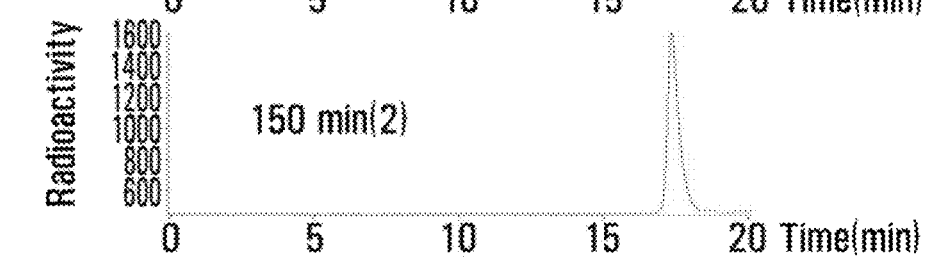
FIG. 4E shows an HPLC chromatogram for investigating the serum stability of Rhodamine-Compound 10 of Table 1 at 150 minutes.
Figure 4F:
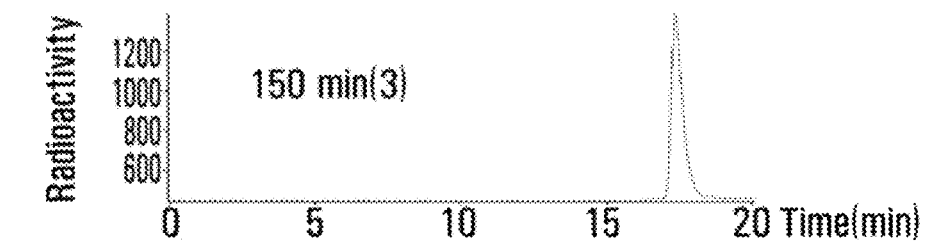
FIG. 4F shows an HPLC chromatogram for investigating the serum stability of Rhodamine-Compound 10 of Table 1 at 150 minutes.

4A through FIG. 4F. Based on the in vitro test (n=3), almost no decomposition was observed in 150 mins, which proved that Compound 10 has excellent stability in plasma. The observed excellent stability of Compound 10 in plasma suggest that it should present good stability under in vivo conditions.

Example 5. Radiolabeling and Animal Study with Rhodamine(B)-AMBF₃

The following compound, wherein Rhodamine(B) is conjugated to Compound 10, was synthesized and injected into mice.

Compound 18

Compound 18 was synthesized according to the method outlined below:

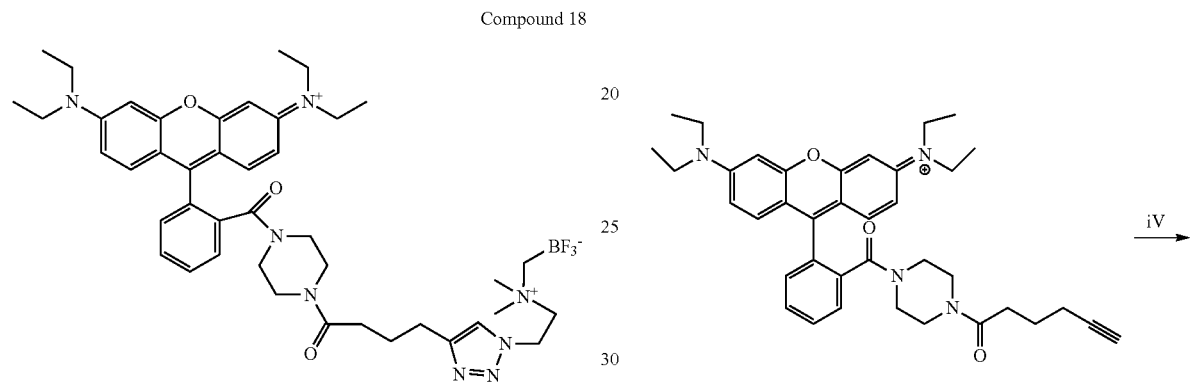

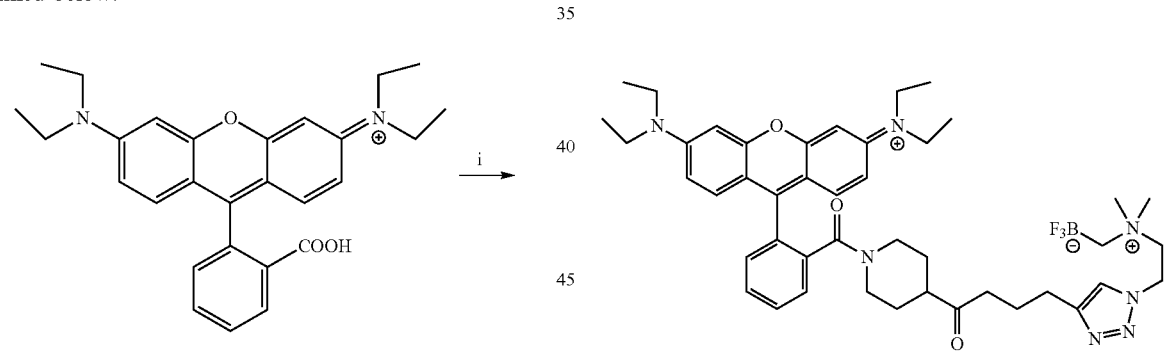

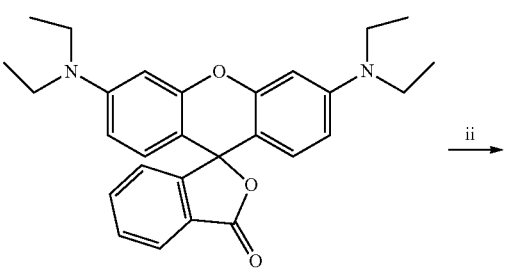

(i. NaOH, EtOAc/water, R.T., 90%; ii. 2.0 equiv. trimethyl aluminum, 4.0 equiv. piperazine, DCM, R.T., work up, 45%; iii. 2.0 equiv. 5-Hexynoic acid NHS ester, DMF/DCM, R.T., 65%; IV. One-pot two steps copper-catalyzed click reaction, purified by HPLC, 80%).

Figure 5B:
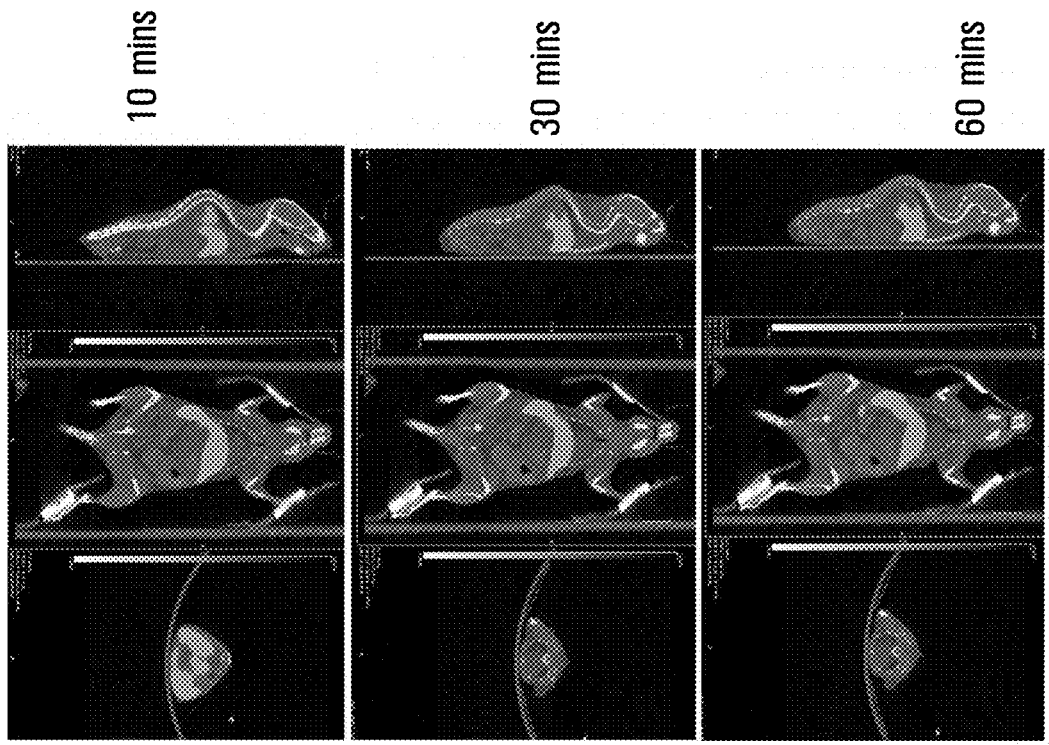
FIG. 5B shows PET-CT images of a mouse at 10, 30, and 60 min post injection with Compound 18.
Figure 5A:
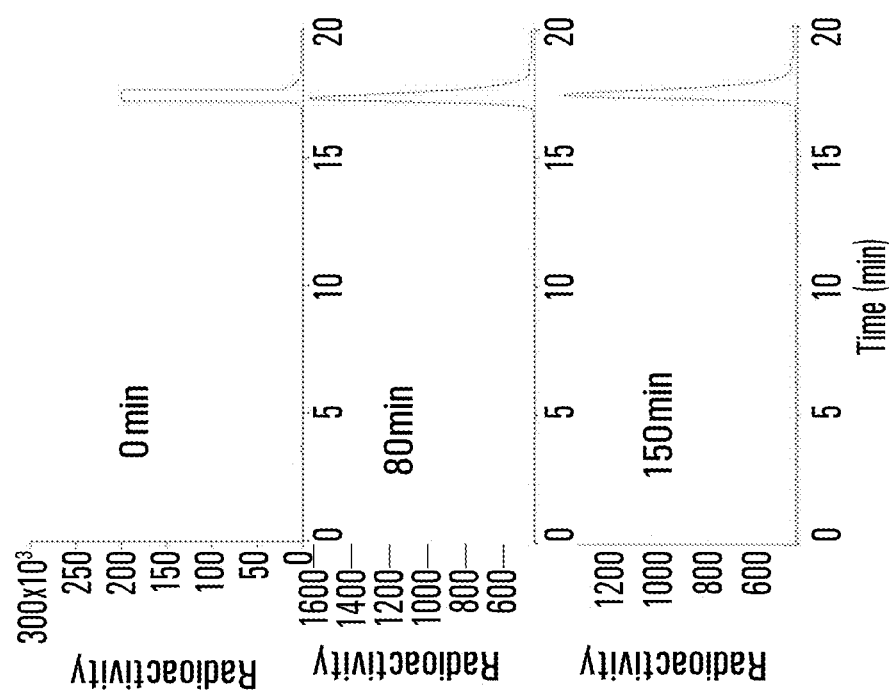
FIG. 5A shows HPLC traces of radioactivity in the plasma of a mouse injected with Compound 18 at 0, 80 and 150 min post injection.

FIG. 5A shows HPLC traces of radioactivity in the plasma of a rat injected with Compound 18 at 0, 80 and 150 min post injection. FIG. 5B shows PET/CT images of the mouse at 10, 30, and 60 min post injection.

Example 7. Radiolabeling and Animal Study with bissulfo-rhodamine(B)-AMBF₃

The following compound, wherein sulforhodamine(B) is conjugated to Compound 13, was synthesized and injected into mice.

Compound 19

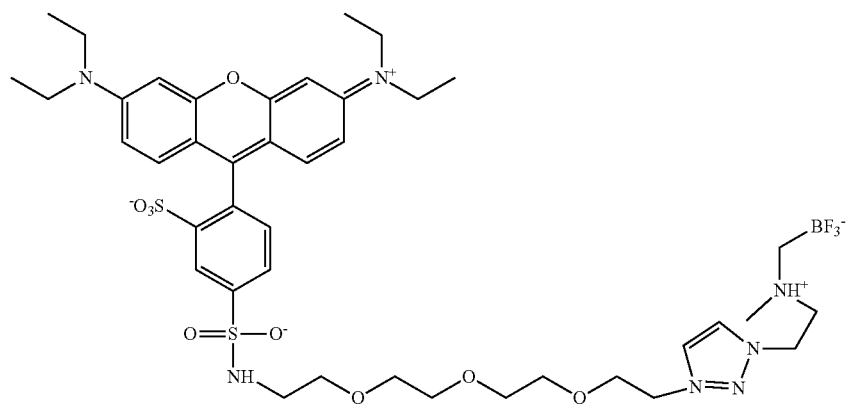

FIG. 6A show the uptake value of different organs for Rhodamine-Compound 10 at 60 min post injection into a mouse. FIG. 6B is a PET/CT image of a mouse injected with Rhodamine-Compound 10 at 60 min post injection.

Example 7. Folate-ammoniomethylamino-BF$_3$

The following compound, Compound 10 conjugated to folic acid, has been synthesized.

Compound 20

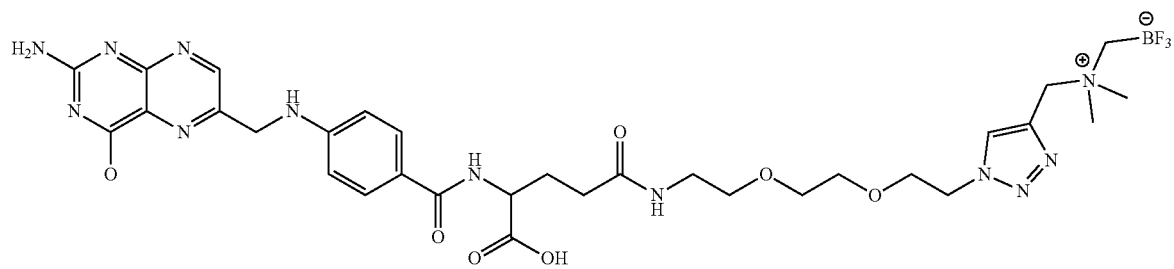

Compound 20 was synthesized according to the method outlined below:

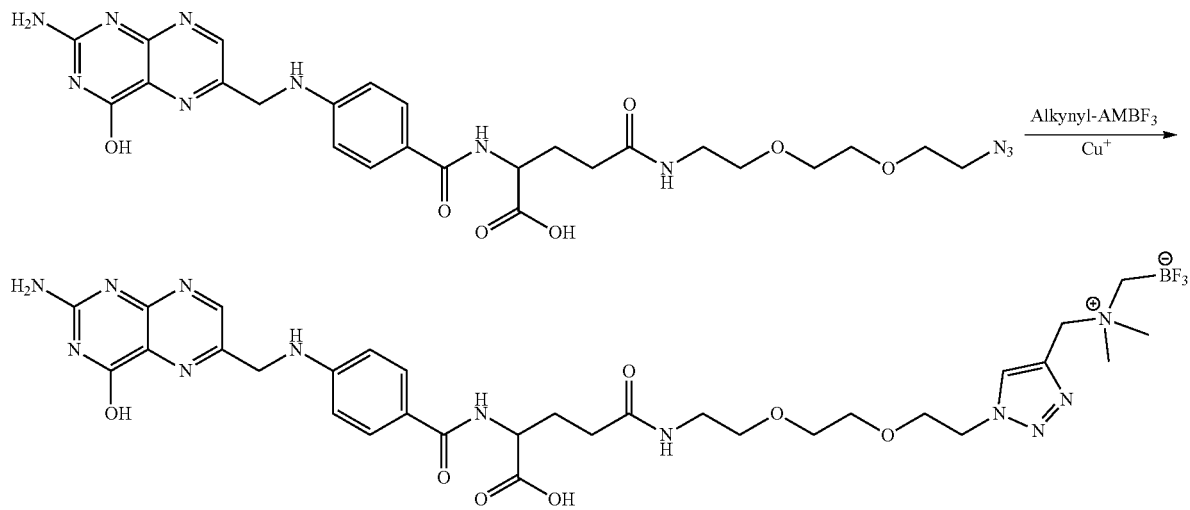

Example 8. BisRGD-rho-AMBF3

Various embodiments of the invention provide peptides or neurotracers conjugated to the positron-emitting organofluoroborate compounds described herein. A person skilled in the art will understand that the positron-emitting organofluoroborate compounds described herein can be conjugated to a ligand (e.g. a peptide or a neurotracer) with affinity and specificity for a biomolecule of interest, provided that a suitable linker is chosen such that the affinity of the ligand for the biomolecule of interest is not reduced by not more than a factor of 100. Such compounds may serve as useful tracers.

For example, BisRGD-rho-AMBF$_3$ (Compound 21) has been synthesized according to the methods described in Zhibo Liu et al. *Med Chem Comm* 2014 5: 171-179 and Liu et al. *Nucl. Med. and Biology* 2013 40: 841-849. Methods for conjugation may include use of an alkyne- or azide-linked tri-substituted ammonium methyl-BF3 or disubstituted protonated ammonium-methyl-BF3 that is linked to the peptide by copper-catalyzed or strain promoted cycloaddition reactions. A person skilled in the art will understand that rhodamine is used for the purposes of screening various RBF3 on TLC and for easily measuring the specific activity of a tracer, and has also been used specifically to direct tracers for cardiac imaging. However, those skilled in the art will further understand that the rhodamine can be replaced with a peptide or other ligand to be imaged.

open-ended term, substantially equivalent to the phrase 'including, but not limited to', and the word 'comprises' has a corresponding meaning. As used herein, the singular forms 'a', 'an' and 'the' include plural referents unless the context clearly dictates otherwise. Thus, for example, reference to 'a thing' includes more than one such thing. Citation of references herein may be not an admission that such references are prior art to the present invention. Publications, including patents and patent applications, cited in this specification are incorporated herein by reference as if each individual publication were specifically and individually indicated to be incorporated by reference herein and as though fully set forth herein. The invention includes all embodiments and variations substantially as hereinbefore described and with reference to the examples and drawings.

The invention claimed is:

1. A positron emitting compound or salt thereof having a half-life with respect to solvolytic de-$^{18}$F-fluoridation at physiological pH of about 1000 minutes or more, wherein the compound is of the formula (IV):

Compound 21

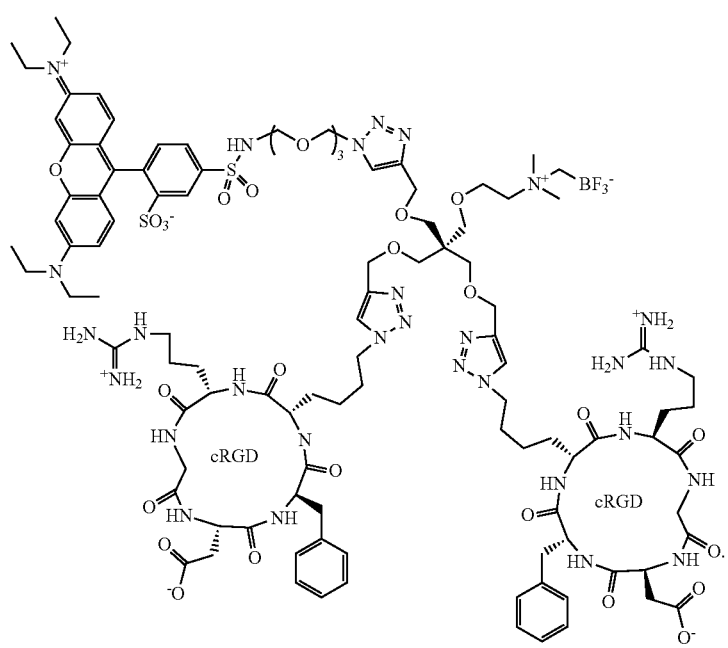

Figure 7:
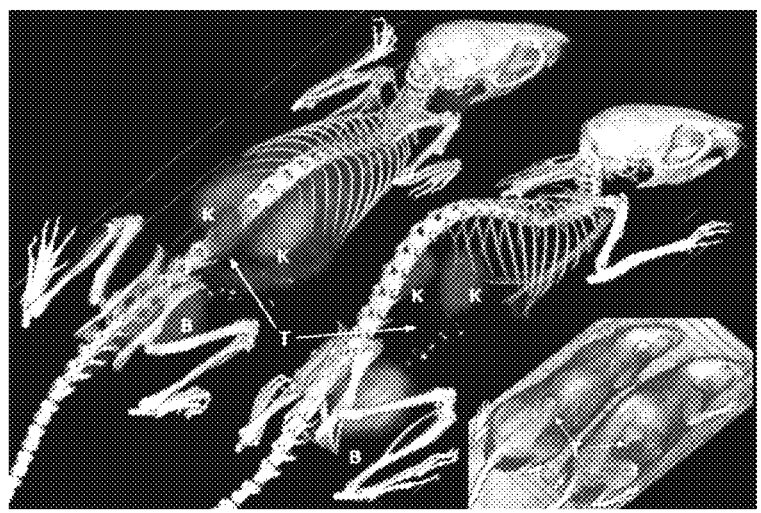
FIG. 7 shows PET-CT images of mice injected with Compound 20. T=tumor, K=kidney, B=bladder. The mouse on the left was imaged with Compound 20 at 3 Ci/µmol, whereas the mouse on the right was imaged with Compound 20 at 0.01 Ci/µmol. The bottom shows a pure CT showing tumors.

FIG. 7 shows PET-CT images of mice injected with Compound 21.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word 'comprising' may be used herein as an wherein:

B is boron;

each Y$^1$ is independently selected from the group consisting of R$^1$, $^{18}$F and $^{19}$F;

n=1 or 2;

Y$^2$ is selected from the group consisting of R$^2$, $^{18}$F and $^{19}$F;

R$^1$ is a non-interfering substituent with regard to fluoridation of B;

$R^2$ is a non-interfering substituent with regard to fluoridation of B;

at least one of $(Y^1)_n$ and $Y^2$ is $^{18}F$;

$Q^1$ is —C≡CR$^8$,

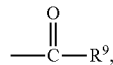

or —R$^{10}$C═CR$^{11}$R$^{12}$;

$R^8$ is —N$^+$R$^{25}$R$^{26}$R$^{27}$, P$^+$R$^{28}$R$^{29}$R$^{30}$, —S$^+$R$^{31}$R$^{32}$, —NR$^{33}$R$^{34}$,

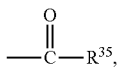

a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is substituted with at least one substituent that is a biomolecule and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the carbon atom of —C≡CR$^8$ through a carbon atom;

each of R$^{25}$, R$^{26}$ and R$^{27}$ is independently a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the nitrogen atom of —N$^+$R$^{25}$R$^{26}$R$^{27}$ through a carbon atom, or R$^{25}$ is absent and R$^{26}$ and R$^{27}$ are joined so that —N$^+$R$^{25}$R$^{26}$R$^{27}$ forms a positively charged nitrogen containing heterocyclic group which is unsubstituted or substituted;

each of R$^{28}$, R$^{29}$, and R$^{30}$ is independently a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the phosphorus atom of —P$^+$R$^{28}$R$^{29}$R$^{30}$ through a carbon atom;

each of R$^{31}$ and R$^{32}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the sulfur atom of —S$^+$R$^{31}$R$^{32}$ through a carbon atom;

each of R$^{33}$ and R$^{34}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the nitrogen atom of —NR$^{33}$R$^{34}$ through a carbon atom;

R$^{35}$ is a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is substituted with at least one substituent that is a biomolecule and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the carbon atom of

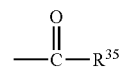

through a carbon atom;

R$^9$ is —NR$^{38}$R$^{39}$,

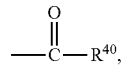

a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is substituted with at least one substituent that is a biomolecule and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the carbon atom of

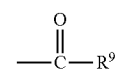

through a carbon atom;

each of R$^{38}$ and R$^{39}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the nitrogen atom of —$NR^{38}R^{39}$ through a carbon atom;

$R^{40}$ is a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is substituted with at least one substituent that is a biomolecule and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the carbon atom of

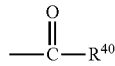

through a carbon atom;

each of $R^{10}$, $R^{11}$, and $R^{12}$ is independently H, D, F, Cl, Br, I, $CX_3$, —$N^+R^{41}R^{42}R^{43}$, —$P^+R^{44}R^{45}R^{46}$, —$S^+R^{47}R^{48}$, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, each of the $C_1$-$C_{15}$ alkyl group and the $C_3$-$C_{18}$ cycloalkyl group is joined to the carbon atom of —$R^{10}C$=$CR^{11}R^{12}$ through a carbon atom, and each X is the same or different and is F, Cl, Br, or I;

each of $R^{41}$, $R^{42}$ and $R^{43}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the nitrogen atom of —$N^+R^{41}R^{42}R^{43}$ through a carbon atom, or $R^{41}$ is absent and $R^{42}$ and $R^{43}$ are joined so that —$N^+R^{41}R^{42}R^{43}$ forms a positively charged nitrogen containing heterocyclic group which is substituted or unsubstituted;

each of $R^{44}$, $R^{45}$, and $R^{46}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the phosphorus atom of —$P^+R^{44}R^{45}R^{46}$ through a carbon atom; and each of $R^{47}$ and $R^{48}$ is independently H, D, a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is unsubstituted or substituted and optionally includes at least one heteroatom interposed between two carbon atoms of the carbon chain of the group, wherein each of the at least one heteroatom is independently selected from the group consisting of O, S, N and P, and each of the $C_1$-$C_{15}$ alkyl group and the $C_3$-$C_{18}$ cycloalkyl group is joined to the sulfur atom of —$S^+R^{47}R^{48}$ through a carbon atom;

providing that $Q^1$ is selected such that the $pK_a$ of Ha of an acid of the formula:

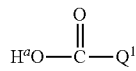

is less than or equal to about 2.8.

2. The positron emitting compound or salt of claim 1, wherein when $Q^1$ is substituted at the carbon alpha to the

group with a group that has a dissociable proton, the dissociable proton has a pKa greater than about 9 and contributes to a net positive charge on the group that has the dissociable proton.

3. The positron emitting compound or salt of claim 1, wherein $Q^1$ is selected such that the $pK_a$ of $H^a$ of the acid of the formula

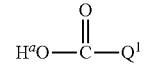

is less than or equal to about 2.4, less than or equal to about 2.0, less than or equal to about 1.5 or less than or equal to about 1.0.

4. The positron emitting compound or salt as defined in claim 1, wherein at least one of $R^8$, $R^9$, $R^{10}$, $R^{11}$, $R^{12}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{38}$, $R^{39}$, $R^{40}$, $R^{41}$, $R^{42}$, $R^{43}$, $R^{44}$, $R^{45}$, $R^{46}$, $R^{47}$, and $R^{48}$ is a biomolecule, a linking group optionally joined to a biomolecule, or a group that is substituted with at least one substituent that is a biomolecule, or forms a group that is substituted with at least one substituent that is a biomolecule.

5. The positron emitting compound or salt of claim 1, wherein $Q^1$ is —C≡$CR^8$, or

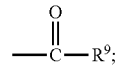

and each $R^8$ and $R^9$ is as defined in claim 1.

6. The positron emitting compound or salt of claim 1, wherein:

$Q^1$ is —C≡$CR^8$;

wherein $R^8$ is a biomolecule, a linking group optionally joined to a biomolecule, a linear or branched $C_1$-$C_{15}$ alkyl group, or a $C_3$-$C_{18}$ cycloalkyl group, wherein each of the $C_1$-$C_{15}$ alkyl group and the $C_3$-$C_{18}$ cycloalkyl group is substituted with at least one substituent that is a biomolecule and is optionally intercepted with at least one heteroatom selected from the group consisting of O, S, N and P, and each of the $C_1$-$C_{15}$ alkyl group and the $C_3$-$C_{18}$ cycloalkyl group is joined to the carbon atom of —C≡$CR^8$ through a carbon atom.

7. The positron emitting compound or salt of claim 1, wherein each of $R^1$ and $R^2$ is independently a linear or branched $C_1$-$C_{15}$ alkyl group or a non-aromatic $C_3$-$C_{18}$ cycloalkyl group, wherein each of the $C_1$-$C_{15}$ alkyl group and the non-aromatic $C_3$-$C_{18}$ cycloalkyl group is unsubstituted or substituted and is optionally intercepted with at least one heteroatom selected from the group consisting of O, S, N and P.

8. The positron emitting compound or salt of claim 1, wherein n is 2, each $Y^1$ is F and $Y^2$ is F.

9. The positron emitting compound or salt as defined in claim 1, wherein at least two of $(Y^1)_n$ and $Y^2$ are $^{18}F$.

10. The positron emitting compound or salt of claim 1, conjugated to a biomolecule.

11. The positron emitting compound or salt of claim 10, wherein the biomolecule is a peptide.

12. The positron emitting compound or salt of claim 1, wherein $Q^1$ is —C≡$CR^8$; and $R^8$ is as defined in claim 1.

13. The positron emitting compound or salt of claim 1, wherein $Q^1$ is

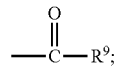

and $R^9$ is as defined in claim 1.

14. The positron emitting compound or salt of claim 1, wherein $Q^1$ is —$R^{10}$C=$CR^{11}R^{12}$; and each of $R^{10}$, $R^{11}$, and $R^{12}$ is as defined in claim 1.

15. The positron emitting compound or salt as defined in claim 1, having a solvolytic de-$^{18}$F-fluoridation half-life at physiological pH of about 5000 minutes or more.

* * * * *